(12) United States Patent
Traynelis et al.

(10) Patent No.: US 9,737,522 B2
(45) Date of Patent: Aug. 22, 2017

(54) NMDA RECEPTOR MODULATORS AND USES RELATED THERETO

(71) Applicant: EMORY UNIVERSITY, Atlanta, GA (US)

(72) Inventors: Stephen F. Traynelis, Decatur, GA (US); Praseeda Mullasseril, Rockville, MD (US); Ethel C Garnier, Tucker, GA (US); Dennis C. Liotta, Atlanta, GA (US); Sommer Zimmerman, Clarkston, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/419,084

(22) PCT Filed: Aug. 7, 2013

(86) PCT No.: PCT/US2013/054031
§ 371 (c)(1),
(2) Date: Feb. 2, 2015

(87) PCT Pub. No.: WO2014/025942
PCT Pub. Date: Feb. 13, 2014

(65) Prior Publication Data
US 2015/0196540 A1 Jul. 16, 2015

Related U.S. Application Data

(60) Provisional application No. 61/681,223, filed on Aug. 9, 2012, provisional application No. 61/776,822, filed on Mar. 12, 2013.

(51) Int. Cl.
| | |
|---|---|
| *C07D 401/14* | (2006.01) |
| *A61K 31/444* | (2006.01) |
| *A61K 31/404* | (2006.01) |
| *A61K 31/4015* | (2006.01) |
| *A61K 31/4439* | (2006.01) |
| *A61K 45/06* | (2006.01) |
| *C07D 207/38* | (2006.01) |
| *C07D 401/06* | (2006.01) |
| *C07D 403/06* | (2006.01) |
| *C07D 409/14* | (2006.01) |

(52) U.S. Cl.
CPC .......... *A61K 31/444* (2013.01); *A61K 31/404* (2013.01); *A61K 31/4015* (2013.01); *A61K 31/4439* (2013.01); *A61K 45/06* (2013.01); *C07D 207/38* (2013.01); *C07D 401/06* (2013.01); *C07D 401/14* (2013.01); *C07D 403/06* (2013.01); *C07D 409/14* (2013.01)

(58) Field of Classification Search
CPC .................................................. C07D 401/14
USPC ...................................... 546/277.4; 514/339
See application file for complete search history.

(56) References Cited

U.S. PATENT DOCUMENTS

| | | |
|---|---|---|
| 2010/0210632 A1 | 8/2010 | Kai |
| 2011/0130397 A1* | 6/2011 | Choi .................... C07D 413/14 514/234.2 |
| 2011/0183939 A1 | 7/2011 | Kai |

FOREIGN PATENT DOCUMENTS

| | | |
|---|---|---|
| WO | 03030897 | 4/2003 |
| WO | 2004000227 | 12/2003 |
| WO | 2008055945 | 5/2008 |
| WO | 2008120725 | 9/2008 |
| WO | 2010081783 | 7/2010 |
| WO | 2012098172 | 7/2012 |

OTHER PUBLICATIONS

Dorwald, Side Reactions in Organic Synthesis, 2005, Wiley: VCH Weinheim Preface, pp. 1-15 & Chapter 8, pp. 279-308.*
AMR "Anticonvulsant and Antiparkinsonian Evaluation of Some Synthesized Chiral Peptide Derivatives Using 3-benzoyl-4, 5-dioxo-2-phenyl-pyrrolidin-1-y1) Acetic Acid" World Journal of Chemistry, 2010; 5(1): 01-06.
Gein et al. "Synthesis and biological activity of 5-aryl-4-acyl-3-hydroxy-1-morpholinoalkyl-3-pyrrolin-2-ones" Pharmaceutical Chemistry Journal, 2007; 41(5): 256-263.
Gein et al. "Synthesis and Pharmacological Activity of 1-Alkoxyaryl-5-Aryl-4-Acyl-3-Hydroxy-3-Pyrrolin-2-Ones" Pharmaceutical Chemistry Journal, Sep. 2011; 45(6): 355-358.
Khatri et al. "Determinants and Mechanism of Action of a GIuN2C-selective NMDA Receptor Positive Allosteric Modulator" Mol Pharmacol., 2014; 86(5): 548-560.
Mosley et al. "Quinazolin-4-one derivatives as a novel class of noncompetitive NR2C/D subunit-selective NMDA receptor antagonists" J Med Chem, 2010; 53(15): 5476-5490.
Mullasseril et al. "A NR2C/D-selective class of NMDA receptor potentiators" Nat Commun., 2010; 1: 90.
Nicholls et al. "Transgenic Mice Lacking NMDAR-Dependent LTD Exhibit Deficits in Behavioral Flexibility" Neuron, 2008; 58: 104-117.
Strong et al. "NMDA receptor modulators: an updated patent review (2013-2014)" Expert Opin. Ther. Patents, 2014; 24(12): 1349-1366.

(Continued)

*Primary Examiner* — Patricia L Morris
(74) *Attorney, Agent, or Firm* — Emory Patent Group

(57) ABSTRACT

This disclosure relates to NMDA modulators and used related thereto such as for treatment of central nervous system disorders. In certain embodiments, compounds disclosed herein are NR2C subunit-selective NMDA potentiators. In certain embodiments, the disclosure contemplates compounds and pharmaceutical compositions. In certain embodiments, the disclosure contemplates compounds disclosed herein as prodrugs, optionally substituted with one or more substituents, derivatives, or salts thereof. In certain embodiments, the disclosure relates to methods of treating or preventing nervous system disorders comprising administering an effective amount of a composition comprising compound disclosed herein to a subject in need thereof.

6 Claims, 1 Drawing Sheet

(56) References Cited

OTHER PUBLICATIONS

Zimmerman et al. "Design, synthesis, and structure-activity relationship of a novel series of GluN2C-selective potentiators" J Med Chem, 2014; 57(6): 2334-2356.

* cited by examiner

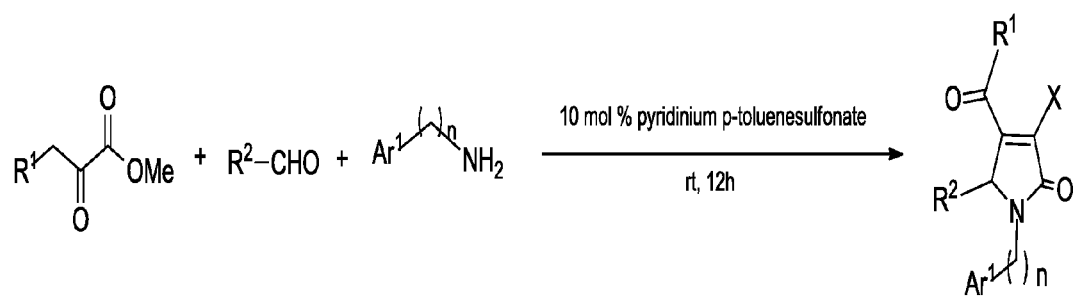

NMDA RECEPTOR MODULATORS AND USES RELATED THERETO

CROSS REFERENCE TO RELATED APPLICATIONS

This Application is a 371 USC filing of International Application PCT/US2013/054031 filed Aug. 7, 2013, which claims the benefit of priority to U.S. Provisional Application No. 61/681,223 filed Aug. 9, 2012, and U.S. Provisional Application No. 61/776,822 filed Mar. 12, 2013, which applications are hereby incorporated by reference in their entireties.

BACKGROUND

NMDA (N-methyl-D-aspartate) is the defining agonist of a subclass of ionotropic glutamate receptors. Activation of NMDA receptors results in the opening of an ion channel that depolarizes the cell and increases the concentration of $Ca^{2+}$ in the cell, which is a secondary messenger in various signaling pathways. NMDA receptors play a role in physiological process such as memory and depression. See e.g., Nicholls et al., Neuron, 2008, 58(1):104-17.

Agents that modulate NMDA receptors are known for a variety of therapeutic applications. For example, memantine is used to treat Alzheimer's disease and dementia with Lewy bodies. Amantadine is an anti-Parkinsonian drug. Ketamine is used for the induction and maintenance of general anesthesia, and has recently been shown to be effective in clinical trials against treatment-resistant depression. Common side effects of NMDA modulators are sedation and hallucinations. Thus, there is a need to identify improved agents.

Mosley et al. reported quinazolin-4-one derivatives as a novel class of noncompetitive NR2C/D subunit-selective NMDA receptor antagonists. See J Med Chem, 2010, 53(15), 5476-5490. Mullasseril et al. reported on a NR2C/D-selective class of NMDA receptor potentiators. See Nat Commun. 2010, 1:90. See also WO 2010/088414, WO 2010/114636, WO 2010/081783, WO 2012/098172, WO 2004/000227, WO 2008/120725, and CN 102603717.

SUMMARY

This disclosure relates to NMDA modulators and uses related thereto such as for treatment of central nervous system disorders. In certain embodiments, compounds disclosed herein are NR2C subunit-selective NMDA potentiators. In certain embodiments, the disclosure contemplates compounds and pharmaceutical compositions. In certain embodiments, the disclosure contemplates compounds disclosed herein as prodrugs, optionally substituted with one or more substituents, derivatives, or salts thereof. In certain embodiments, the disclosure relates to methods of treating or preventing nervous system disorders comprising administering an effective amount of a composition comprising a compound disclosed herein to a subject in need thereof.

In certain embodiments, the disclosure relates to compounds of the Formula I

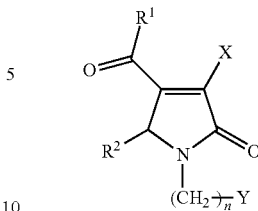

Formula I or salts thereof, wherein

X is OH or $NH_2$, wherein X optionally substituted with J;

Y is a bicyclic carbocyclyl or $Ar^1$ is aryl, heterocyclyl, bicyclic heterocyclyl, bicyclic heterocycle comprising one five-membered ring and one six-membered ring, bicyclic heterocycle comprising one five-membered heterocyclic ring and one six-membered aryl ring, bicyclic heterocycle comprising one five-membered heterocyclic ring and one six-membered heterocyclic ring, a bicyclic heterocycle comprising two six-membered rings; a bicyclic heterocycle comprising two six-membered aryl rings, a bicyclic heterocycle comprising two six-membered hetercyclic rings, a bicyclic heterocycle comprising one heterocyclic six-membered ring and one aromatic six-membered ring, or an bicyclic aryl, wherein Y or $Ar^1$ is optionally substituted with one or more, the same or different, J;

n is 0, 1, 2, 3, 4, or 5;

$R^1$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, J;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, J; and J is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein J is optionally substituted with one or more, the same or different, K;

K is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is OH.

In certain embodiments, the disclosure contemplates compounds disclosed herein comprising one or more, the same or different substituents and salts thereof.

In certain embodiments, the disclosure contemplates pharmaceutical compositions comprising compounds disclosed herein or a pharmaceutically acceptable salt and a pharmaceutically acceptable excipient. In certain embodiments, the disclosure relates to pharmaceutical compositions comprising a compound disclosed herein and a second active agent. In certain embodiments, the second active agent is an antipsychotic.

In certain embodiments, the disclosure contemplates methods of treating or preventing central nervous system impairments. In some embodiments, the central nervous system impairments are selected from cognitive impairment, a neurodegenerative disease, pain, depression, attention deficit hyperactivity disorder, motor disorders, or addiction.

In certain embodiments, the disclosure relates to methods of treating or preventing a cognitive, psychiatric, or neurodegenerative disease or condition by administering to a person in need of such treatment an effective amount of a pharmaceutical composition as described herein In certain embodiments, the disease or condition is cognitive impairment, a neurodegenerative disease, pain, depression, attention deficit hyperactivity disorder, or addiction.

In certain embodiments, the neurodegenerative disease is Alzheimer's disease or mild cognitive impairment.

In certain embodiments, the pharmaceutical composition is administered in combination with a second active agent.

In certain embodiments, the second active agent is an antidepressant or antipsychotic.

In certain embodiments, the disclosure contemplates methods of making compounds disclosed herein by mixing starting material under condition to form the products.

BRIEF DESCRIPTION OF THE FIGURES

FIG. 1 shows a scheme for preparing certain embodiments of the disclosure.

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, physiology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

Unless specifically designated by a specific structural character, chemical formulas as provided herein that have chiral centers are intended to encompass racemic, enantiomeric, and diastereomeric forms.

As used herein, "alkyl" means a noncyclic straight chain or branched, unsaturated or saturated hydrocarbon such as those containing from 1 to 22 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 8 to 22 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butyryl, 2-butyryl, 1-pentynyl, 2-pentynyl, 3-methyl-1-butyryl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, indolizinyl, indazolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH3).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, and t-butoxy.

"Alkylamino" refers an alkyl group as defined above attached through an amino bridge. An example of an alkylamino is methylamino, (i.e., —NH—CH3).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)2alkyl) such as mesyl and the like, and "Arylsulfonyl" refers to an aryl attached through a sulfonyl bridge (i.e., —S(=O)2aryl).

"Alkylsulfinyl" refers to an alkyl as defined above attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In typical embodiments, the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, rodent, monkey or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted with one or more substituents, a salt, in different hydration/oxidation states, e.g., substituting a single or double bond, substituting a hydroxy group for a ketone, or because one or more atoms within the molecule are switched, such as, but not limited to, replacing an oxygen atom with a sulfur or nitrogen atom or replacing an amino group with a hydroxyl group or vice versa. Replacing a carbon with nitrogen in an aromatic ring is a contemplated derivative. The derivative may be a prodrug. Derivatives may be prepared by any variety of synthetic methods or appropriate adaptations presented in the chemical literature or as in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

NMDA Receptor Modulators

NMDA receptors are multimeric complexes comprised of a glycine binding NR1 subunit and two of the various glutamate binding NR2 subunits (NR2A, B, C, D). The four distinct NR2 subunits control receptor properties, and show different spatial and temporal expression patterns, along with differing functional properties. NR2C-selective NMDA receptor potentiators are expected to have many uses as new therapeutic agents. In particular, NMDA receptor potentiators have been linked to cognition enhancing processes. NMDA receptor modulators have also been considered potentially useful compounds for schizophrenia, based on the working hypothesis that NMDA receptor hypofunction is one underlying cause of schizophrenia. In addition, NMDA receptor potentiators may enhance interneuron function, and act as an anticonvulsant. NMDA receptor modulators have also been explored for applications to treat or prevent pain, depression, dementia or cognitive impairments, depression, attention deficit hyperactivity disorder, eating disorders, addiction, and neurodegenerative diseases including Alzheimer's disease, Parkinson's disease, amyotrophic lateral sclerosis (ALS), and disorders of the motor system. NR2C has prominent expression in the cerebellum, interneurons, and elsewhere that suggests selective potentiation of NR2C containing NMDA receptors will have important and useful effects. It is thus an object of this disclosure to describe a class of compounds which may be used as treatments to various central nervous system disorders by modulating NMDA activity.

Compounds

In certain embodiments, the disclosure relates to compounds of the Formula I

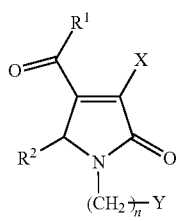

Formula I or salts thereof, wherein

X is OH or $NH_2$, wherein X is optionally substituted with J;

Y is bicyclic carbocyclyl or $Ar^1$ is aryl, heterocyclyl, bicyclic heterocyclyl, bicyclic heterocycle comprising one five-membered ring and one six-membered ring, bicyclic heterocycle comprising one five-membered heterocyclic ring and one six-membered aryl ring, bicyclic heterocycle comprising one five-membered heterocyclic ring and one six-membered heterocyclic ring, a bicyclic heterocycle comprising two six-membered rings; a bicyclic heterocycle comprising two six-membered aryl rings, a bicyclic heterocycle comprising two six-membered hetercyclic rings, a bicyclic heterocycle comprising one heterocyclic six-membered ring and one aromatic six-membered ring, or an bicyclic aryl, wherein Y or $Ar^1$ is optionally substituted with one or more, the same or different, J;

n is 0, 1, 2, 3, 4, or 5;

$R^1$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, J;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, J; and J is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein J is optionally substituted with one or more, the same or different, K;

K is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $Ar^1$ is a naphyl, indolyl, isoindolyl, indolizinyl, indazolyl, quinazolinyl, benimidazolyl, benzofuranyl, benzothiophenyl, benzopyranyl, pyrido[4,3-d]pyrimidinyl, pyrido[3,2-d]pyrimidinyl, pyrido[3,4-d]pyrimidinyl, pyrido[2,3-d]pyrimidinyl thieno[2,3-d]pyrimidinyl, or oxazolo[5,4-d]pyrimidine optionally substituted with one or more of the same or different J; or

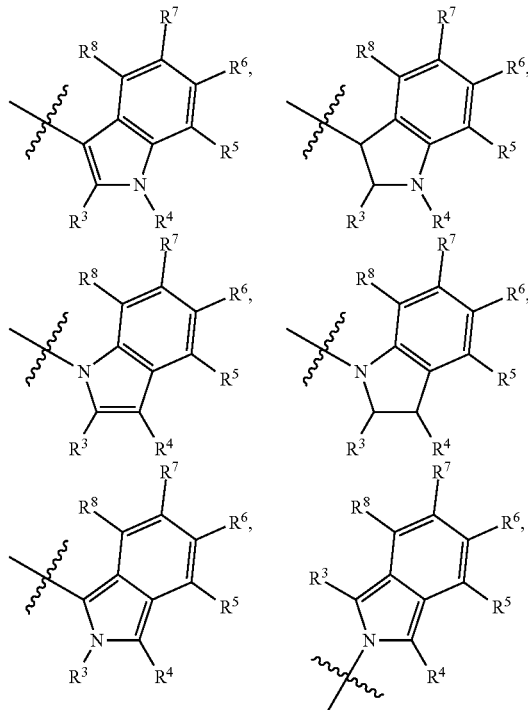

-continued

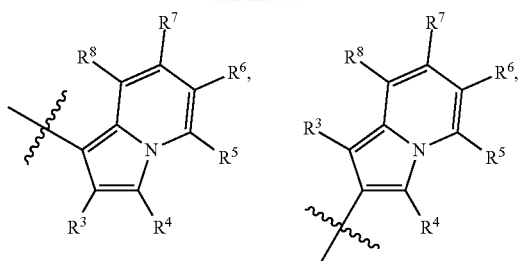

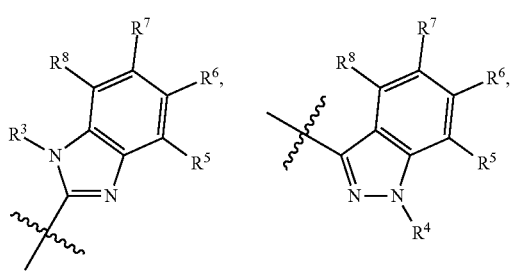

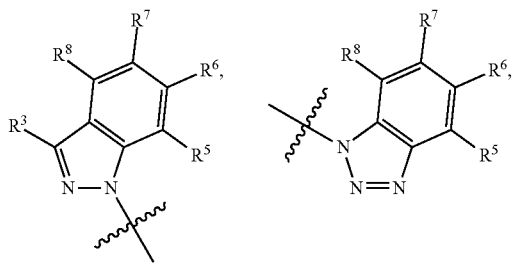

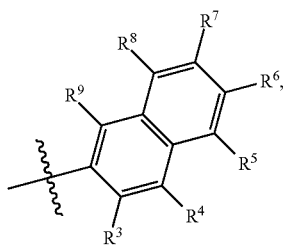

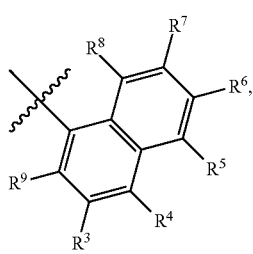

-continued

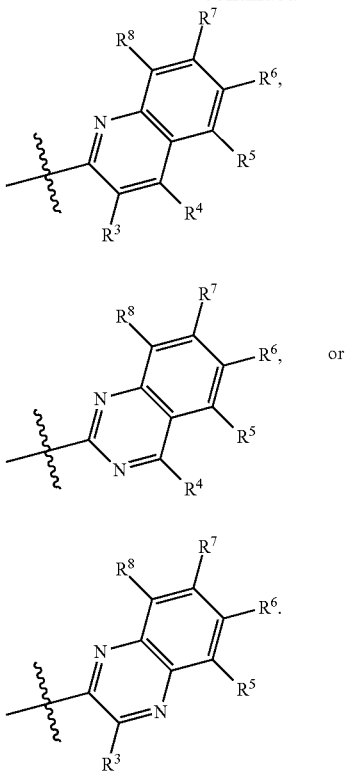

wherein, $R^3$, $R^4$, $R^5$, $R^6$, $R^7$, $R^8$, and $R^9$ are each, the same or different alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, and $R^9$ are each optionally substituted with one or more, the same or different, J; or wherein, $R^3$, $R^4$, $R^5$, $R^6$, $R^7$, and $R^8$ are each, the same or different alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, and $R^8$ are each optionally substituted with one or more, the same or different, J; or $R^4$, $R^5$, $R^6$, $R^7$, and $R^8$ are each, the same or different alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$, $R^5$, $R^6$, $R^7$, and $R^8$ are each optionally substituted with one or more, the same or different, J; or $R^4$, $R^6$, $R^7$, and $R^8$ are each, the same or different alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$, $R^6$, $R^7$, and $R^8$ are each optionally substituted with one or more, the same or different, J.

In certain embodiments, X is OH.

In certain embodiments, $Ar^1$ is a indazolyl, or indolizinyl optionally substituted with one or more of the same or different J; or

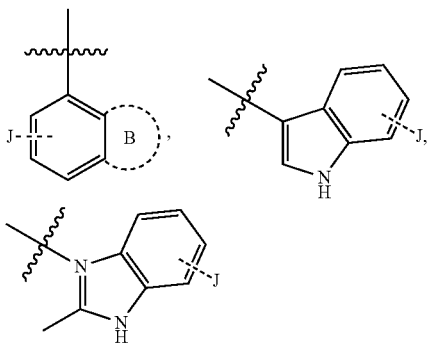

wherein B is an aryl or heterocyclyl.

In certain embodiments, $R^2$ is phenyl substituted with carboxy optionally substituted with J.

In certain embodiments, $R^1$ is alkyl, phenyl, thiophenyl, pyridinyl, 3-pyridinyl, 4-pyridinyl, or heterocyclyl optionally substituted with one or more, the same or different, J.

In certain embodiments, n is 0, 1, or 2.

In certain embodiments, $R^2$ is thiophenyl, para-carbomethoxyphenyl or para-carboethoxyphenyl.

In certain embodiments, Formula I is Formula IA.

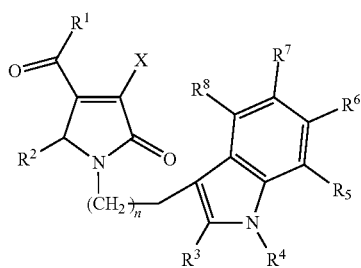

Formula IA or salts thereof, wherein

X is OH, optionally substituted with J;

n is 0, 1, 2, 3, 4, or 5;

$R^1$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, J;

$R^2$ is hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, J; and $R^3$, $R^4$, $R^5$, $R^6$, $R^7$, and $R^8$ are each, the same or different alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, and $R^8$ are each optionally substituted with one or more, the same or different, J;

J is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein J is optionally substituted with one or more, the same or different, K;

K is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^1$ is alkyl, phenyl, thiophenyl, pyridinyl, 3-pyridinyl, 4-pyridinyl, or heterocyclyl optionally substituted with one or more, the same or different, J.

In certain embodiments, $R^2$ is phenyl substituted with carboxy optionally substituted with J.

In certain embodiments, $R^1$ is alkyl, phenyl, or heterocyclyl optionally substituted with one or more, the same or different, J.

In certain embodiments, n is 0 or 1.

In certain embodiments, $R^1$ is selected from: methyl; para-chlorophenyl; para-methoxyphenyl; or para-fluorophenyl.

In certain embodiments, $R^2$ is para-carboalkyloxyphenyl optionally substituted with one or more, the same or different, J.

In certain embodiments, Formula I is Formula IB.

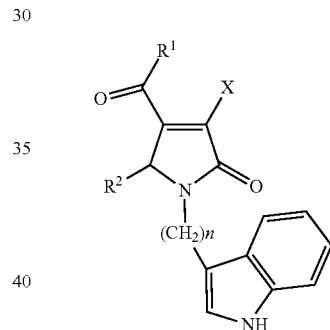

Formula IB or salts thereof, wherein n is 1 or 2;

indolyl is optionally substituted with one or more the same or different, J;

X is OH optionally substituted with J;

$R^1$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, J;

$R^2$ is phenyl, aryl, or heterocyclyl optionally substituted with one or more, the same or different J;

J is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein J is optionally substituted with one or more, the same or different, K;

K is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, Formula I is Formula IC.

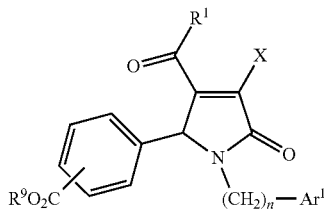

Formula IC or salts thereof, wherein
X is OH optionally substituted with J;
n is 1, 2, 3, 4, or 5;
$Ar^1$ is a pyridinyl, thiophenyl, furanyl, imidazolyl, indolyl, isoindolyl, indolizinyl, indazolyl, pyridyl, or heterocyclyl optionally substituted with one or more of the same or different J; or
$Ar^1$ is aryl, heterocyclyl, bicyclic heterocyclyl, bicyclic heterocycle comprising one five-membered ring and one six-membered ring, bicyclic heterocycle comprising one five-membered heterocyclic ring and one six-membered aryl ring, bicyclic heterocycle comprising one five-membered heterocyclic ring and one six-membered heterocyclic ring, a bicyclic heterocycle comprising two six-membered rings; a bicyclic heterocycle comprising two six-membered aryl rings, a bicyclic heterocycle comprising two six-membered hetercyclic rings, a bicyclic heterocycle comprising one heterocyclic six-membered ring and one aromatic six-membered ring, or an bicyclic aryl, wherein Y or $Ar^1$ is optionally substituted with one or more, the same or different, J; or
$Ar^1$ is a naphyl, indolyl, isoindolyl, indolizinyl, indazolyl, quinazolinyl, benimidazolyl, benzofuranyl, benzothiophenyl, benzopyranyl, pyrido[4,3-d]pyrimidinyl, pyrido[3,2-d]pyrimidinyl, pyrido[3,4-d]pyrimidinyl, pyrido[2,3-d]pyrimidinyl thieno[2,3-d]pyrimidinyl, or oxazolo[5,4-d]pyrimidine optionally substituted with one or more of the same or different J; or

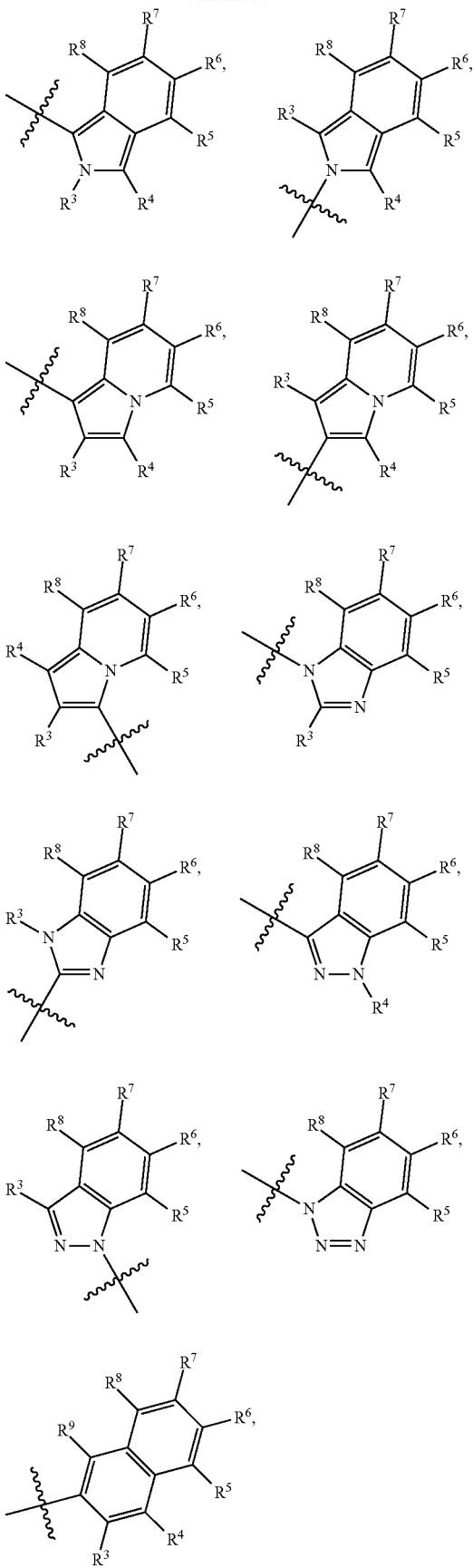

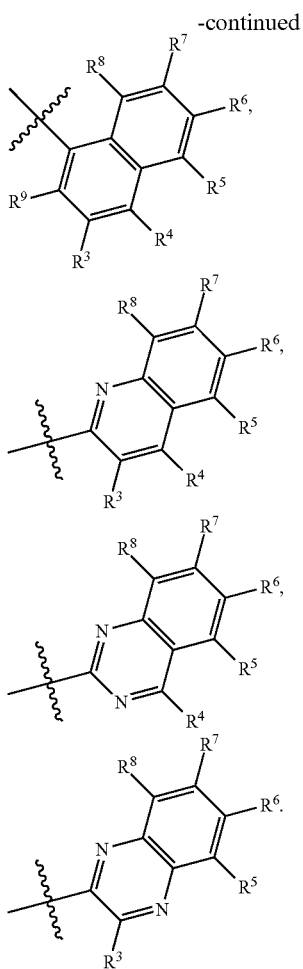

wherein, $R^3$, $R^4$, $R^5$, $R^6$, $R^7$, $R^8$, and $R^9$ are each, the same or different alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, $R^8$, and $R^9$ are each optionally substituted with one or more, the same or different, J; or wherein, $R^3$, $R^4$, $R^5$, $R^6$, $R^7$, and $R^8$ are each, the same or different alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^3$, $R^4$, $R^5$, $R^6$, $R^7$, and $R^8$ are each optionally substituted with one or more, the same or different, J; or $R^4$, $R^5$, $R^6$, $R^7$, and $R^8$ are each, the same or different alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^4$, $R^5$, $R^6$, $R^7$, and $R^8$ are each optionally substituted with one or more, the same or different, J; or $R^4$, $R^6$, $R^7$, and $R^8$ are each, the same or different alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^5$, $R^6$, $R^7$, and $R^8$ are each optionally substituted with one or more, the same or different, J;

$R^1$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, J;

$R^9$ is alkyl, hydroxy, amino, mercapto, alkoxy, alkylthio, alkylamino, (alkyl)$_2$amino, carbocyclyl, aryl, or heterocyclyl, wherein $R^9$ is optionally substituted with one or more, the same or different, J;

J is alkyl, halogen, nitro, cyano, hydroxy, amino, mercapto, formyl, carboxy, alkanoyl, carbamoyl, alkoxy, alkylthio, alkylamino, (alkyl)2amino, alkylsulfinyl, alkylsulfonyl, arylsulfonyl, carbocyclyl, aryl, or heterocyclyl, wherein J is optionally substituted with one or more, the same or different, K;

K is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $Ar^1$ is a pyridine, thiophene, furan, or imidazole optionally substituted with one or more of the same or different J; or

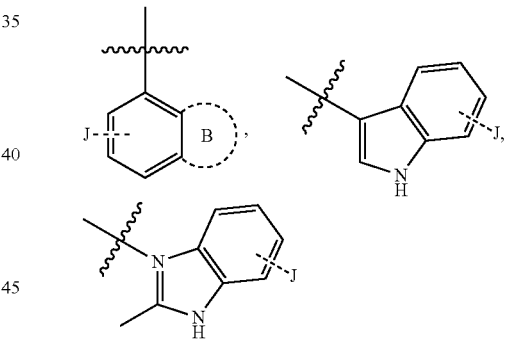

wherein B is an aryl or heterocyclyl.

In certain embodiments, $R^9$ is H or alkyl optionally substituted with J and $Ar^1$ is aryl optionally substituted with J.

In certain embodiments, Formula I is ID,

Formula ID

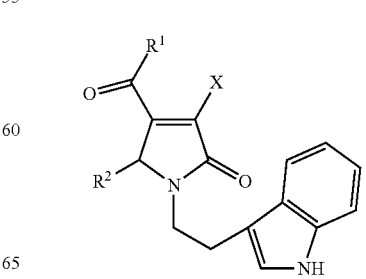

or salts thereof, wherein
indolyl is optionally substituted with one or more the same or different, J;

X is OH optionally substituted with J;

$R^1$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, J;

$R^2$ is phenyl, aryl, or heterocyclyl optionally substituted with one or more, the same or different J;

J is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein J is optionally substituted with one or more, the same or different, K;

K is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrugs can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxyl group. It is well known that ester prodrugs are readily degraded in the body to release the corresponding alcohol. See e.g., Imai, Drug Metab Pharmacokinet (2006) 21(3): 173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. No. 6,372,778, U.S. Pat. No. 6,369,086, U.S. Pat. No. 6,369,087 and U.S. Pat. No. 6,372,733 and the further references mentioned above, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyoptehilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of formula I with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethyl cellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol)

to proteins (PEGylation) to increase the in vivo half-life of circulating therapeutic proteins and decrease the chance of an immune response.

Methods of Treating CNS Diseases

In certain embodiments, the disclosure relates to the method of treating or preventing a disease or condition by administering to a person in need of such treatment an effective amount of a compound of formula I, wherein the disease or condition is cognitive impairment, a neurodegenerative disease, pain, depression, attention deficit hyperactivity disorder, or addiction.

In certain embodiments, the disclosure relates to the method of treating or preventing a disease or condition by administering to a person in need of such treatment an effective amount of a compound of formula I, wherein the disease or condition is neurodegenerative disease such as Alzheimer's, Parkinson's, dementia with Lewy bodies, or mild cognitive impairment.

In certain embodiments, the disclosure relates to the method of treating or preventing a disease or condition by administering to a person in need of such treatment an effective amount of a compound of formula I, wherein the disease or condition is stress, a thought disorder such as hallucinations, delusions, or atatonia or psychiatric disorders such as schizophrenia or a mood disorders such as depression, bipolar disorder, manic depression, post-traumatic stress disorder, obsessive-compulsive disorder, severe sleep deprivation In certain embodiments, the disclosure relates to the method of treating or preventing a disease or condition by administering to a person in need of such treatment an effective amount of a compound of formula I, wherein the disease or condition is stroke, brain tumors, multiple sclerosis, or epilepsy.

In certain embodiments, the disclosure relates to the method of treating or preventing a disease or condition by administering to a person in need of such treatment an effective amount of a compound of formula I, wherein the disease or condition is a motor disorder, dysfunction, or sensory impairment, ataxia, dystonia, or dyskineisa. In certain embodiments, the motor dysfunction is developmental dyspraxia, cerebral palsy, muscular dystrophy, multiple sclerosis, or Parkinson's disease.

In certain embodiments, the disclosure relates to the method of treating or preventing a disease or condition by administering to a person in need of such treatment an effective amount of a compound of formula I, wherein the disease or condition is infectious and postinfectious syndromes, including infections causing delirium, viral encephalitis, HIV, malaria, Lyme disease, or syphilis.

In certain embodiments, the disclosure relates to the method of treating or preventing a disease or condition by administering to a person in need of such treatment an effective amount of a compound of formula I, wherein the disease or condition is endocrine disease, such as hypothyroidism, hyperthyroidism, adrenal failure, Cushing's syndrome, hypoparathyroidism and hyperparathyroidism In certain embodiments, the disclosure relates to the method of treating or preventing a disease or condition by administering to a person in need of such treatment an effective amount of a compound of formula I, wherein the disease or condition is an acquired metabolic disorders, including electrolyte disturbances such as hypocalcemia, hypernatremia, hyponatremia, hypokalemia, hypomagnesemia, hypermagnesemia, hypercalcemia, and hypophosphatemia, but also hypoglycemia, hypoxia, and failure of the liver or kidneys In certain embodiments, the disclosure relates to the method of treating or preventing a disease or condition by administering to a person in need of such treatment an effective amount of a compound of formula I, wherein the disease or condition is autoimmune and related disorders, such as systemic lupus erythematosus (lupus, SLE), sarcoidosis, encephalopathy, and anti-NMDA-receptor encephalitis.

In certain embodiments, the disclosure relates to the method of treating or preventing a disease or condition by administering to a person in need of such treatment an effective amount of a compound of formula I, wherein the disease or condition is poisoning, by therapeutic drugs, recreational drugs, and a range of plants, fungi, metals, organic compounds, and a few animal toxins.

In certain embodiments, the disclosure relates to the method of treating or preventing a disease or condition by administering to a person in need of such treatment an effective amount of a compound of formula I, wherein the disease or condition is some sleep disorders, including hallucinations in narcolepsy (in which REM sleep intrudes into wakefulness).

In certain embodiments, the disclosure relates to a method of treatment, wherein a composition comprised of a compound of formulas I is administered in combination with a second active ingredient, selected from an antidepressant, antipsychotic, or anti-inflammatory agent.

In certain embodiments, the disclosure relates to a method of treatment, wherein a composition comprised of a compound of formulas I is administered in combination with a second active ingredient, selected from acamprosate, amlodipine, argatroban, baclofen, cilostazol, cinacalcet, clopidogrel, dyphylline, fenoldopam, leflunomide, mepacrine, methimazole, phenformin, prilocalne, rifabutin, sulfisoxazole, tadalafil, terbinafine, torasemide, cinnarizine, ciclopirox, eplerenone, carbenoxolone, sulodexide, carbamazine, amobarbital, cefotetan, erythrityl tetranitrate, methyclothiazide, risedronate, enprofylline, oxtriphylline, paramethadione, cefinenoxime, aprindine, etomidate, mitiglinide, benidipine, levosimendan, zonisamide, imipramine, amitriptyline, desipramine, nortriptyline, doxepin, protriptyline, trimipramine, maprotiline, amoxapine, trazodone, bupropion, chlomipramine, fluoxetine, citalopram, sertraline, paroxetine, fluvoxamine, nefazadone, venlafaxine, milnacipran, reboxetine, mirtazapine, phenelzine, tranylcypromine, moclobemide, Kava-Kava, St. John's Wart, s-adenosylmethionine, thyrotropin releasing hormone, neurokinin receptor antagonists and triiodothyronine, or salts thereof.

EXAMPLES

Design of N-Alkyl-N-[(8-R-2,2-dimethyl-2H-chromen-6-yl)methyl]heteroarylsulfonamides Selected compounds were designed as derivatives of a lead compound, 1616 (methyl 4-[3-acetyl-2,5-dihydro-4-hydroxy-1-[2-(1H-indol-3-yl)ethyl]-5-oxo-1H-pyrrol-2-yl] benzoate). Included in these examples are compounds alternatively substituted at the 3-, 4-, and 5-positions of the central dihydropyrrole moiety shown in compounds of Formula I. A scheme showing a general synthetic pathway for certain embodiments is included as FIG. 1.

General Procedures

A: To a stirred solution of aldehyde (1.0 mmol) in dioxane (1.0 M) was added tryptamine (1.0 equiv) and 10 mol % pyridinium 4-methylbenzenesulfonate. Upon the formation of a slurry, methyl acetopyruvate (1.0 equiv) was added. The resulting mixture was allowed to stir at rt for up to 12 hrs. In most instances a precipitate had crashed out of solution, which was collected via filtration and washed with Et$_2$O. The solid was dissolved in an appropriate solvent and washed with saturated ammonium chloride and brine, before being dried over MgSO$_4$, filtered and concentrated in vacuo. Additional purification was achieved via recrystallization with an appropriate solvent system to afford the desired pyrrole. If a precipitate did not form, the mixture was concentrated before being subjected to the work-up as described above. Purification was achieved via flash column chromatography on SiO$_2$ (MeOH/DCM) to afford the desired pyrrole. Additional purification was obtained by HPLC (85% ACN/Water Isocratic) as needed.

B: To a solution of methyl hydroxy-4-iodobenzoate (1.0 mmol) in THF:H2O (4:1, 0.13 M) was added dibutyl vinylboronate (1.5 equiv), sodium carbonate (7.0 equiv) and 5 mol % dichloro-bis(triphenylphosphine)palladium. The reaction mixture was purged with N2 (g) for 5 min before being refluxed for 2 hrs. The resulting mixture was concentrated in vacuo, diluted with EtOAc and washed with water and brine. The combined organic layers were dried over MgSO4, filtered and concentrated in vacuo. Purification was achieved using flash column chromatography on SiO2 (Hexanes/EtOAc: 6/1) to yield the product.

C: Methyl hydroxyl-4-vinylbenzoate (1.0 mmol) was dissolved in DCM (0.4 M) in a flask open to air. The reaction mixture was cooled to −78° C. and a stream of 02 (g) was passed through it for 5 min. At this time, 03 (g) was bubbled into the mixture until the color turned blue. The resulting solution was then purged with 02 (g) for an additional 5 min before being treated with dimethylsulfane (3.0 equiv) and allowed to warm to rt overnight. The mixture was concentrated in vacuo and purified using flash column chromatography on SiO2 (Hexanes/EtOAc: 6/1) to yield the desired product.

D: To a solution of 4-formylbenzoic acid (1.0 mmol) in DMF (0.26 M) was added finely ground potassium carbonate (2.0 equiv) and alkyl halide (2.5 equiv). The reaction stirred at rt until completion was indicated by TLC before being diluted with water and extracted with Et2O (2×). The combined organic layers were then washed with brine, dried over MgSO4, filtered and concentrated in vacuo. Purification was achieved via flash column chromatography on SiO2 (Hexanes/EtOAc: 6/1) to afford the product.

E: To a solution of methyl benzoate (1.0 mmol) in carbon tetrachloride (0.1 M) was added N-bromosuccinimide (2.25 equiv) and benzoic peroxyanhydride (0.04 equiv). The reaction mixture was refluxed for 4 hrs. At this time the resulting solution was cooled to rt and filtered. The filtrate was collected, quenched with water and washed with saturated sodium thiosulfate (2×). The combined organic layers were then dried over MgSO4, filtered and concentrated in vacuo to give the desired methyl 4-(dibromomethyl)benzoate as a yellow oil. The crude material was then dissolved in acetone:water (5:1, 0.35 M) and silver nitrate (2.0 equiv) was added. The flask was covered with foil before being allowed to stir at rt for 3 hrs. The reaction mixture was then filtered through celite, diluted with EtOAc and extracted with saturated sodium bicarbonate (2×). The combined organic layers were washed with water and brine before being dried over MgSO4, filtered and concentrated in vacuo to give the product. Purification was achieved as needed via flash column chromatography on SiO2 (Hexanes/EtOAc: 6/1).

F: To a solution of methyl 4-bromobenzoate (1.0 mmol) in DMF (0.6 M) was added 17 mol % bis(triphenylphosphine)palladium (II) dichloride and sodium formate (1.5 equiv). The reaction mixture was stirred at 110° C. under a steady stream of CO for 2 hrs. At this time, the mixture was cooled to rt, diluted with saturated sodium carbonate and extracted with EtOAc (2×). The combined organic layers were washed with brine, dried over MgSO4, filtered and concentrated in vacuo. Purification was achieved via flash column chromatography on SiO2 (Hexanes/EtOAc: 3/1) to yield the desired product, which was taken on without further purification. The crude material was then dissolved in acetone/water (83/17, 0.35 M) and silver nitrate (2.0 equiv) was added. The flask was covered with foil before being allowed to stir at rt for 3 hrs. The resulting mixture was filtered through celite, diluted with EtOAc and washed with saturated sodium bicarbonate, water and brine. The organic layer was then dried over MgSO4, filtered and concentrated in vacuo. Purification was achieved via flash column chromatography on SiO2 (Hexanes/EtOAc: 6/1) to give the product.

G: To a solution of 4-bromobenzoic acid (1.0 mmol) in THF:MeOH (4:1, 0.3 M) at 0° C. was added (diazomethyl)trimethylsilane (2.4 equiv). The reaction was allowed to warm to rt over the period of 1 hr. At this time the mixture was concentrated in vacuo and 1.0 M HCl was added. The mixture was extracted with EtOAc (2×), dried over MgSO4, filtered and concentrated in vacuo to afford the product.

H: To a solution of sodium ethanolate (1.0 equiv) in EtOH (0.72 M) at 0° C. was added a mixture of diethyl oxalate (1.0 equiv) and ethanone (1.0 mmol) over 20 min. The mixture was allowed to stir at rt for 4 hrs. In most instances a precipitate had formed which was collected via filtration and washed with absolute EtOH. If no precipitate was evident a minimal amount of water was added and the mixture was concentrated in vacuo. The residue was dissolved in water, neutralized with acetic acid and extracted with Et2O (3×). The combined organic layers were dried over MgSO4, filtered and concentrated in vacuo. Purification was achieved as needed via flash column chromatography on SiO2 (Hexanes/EtOAc: 4/1) to obtain the product.

I: To a solution of 4-formylbenzoic acid (1.0 mmol) in DMF (0.61 M) at 0° C. was added DMAP (1.1 equiv) and EDCI (1.0 equiv). The reaction mixture was stirred at 0° C. for 45 minutes. At this time amine (1.0 equiv) was added and the mixture was warmed to room temperature and stirred overnight. The resulting mixture was concentrated in vacuo, partitioned between 1.0 M HCl and EtOAc and extracted with EtOAc (2×). The combined organic layers were washed with brine, dried over MgSO4, filtered and concentrated in vacuo. Purification was achieved via flash column chromatography on SiO2 (Hexanes/EtOAc: 1/1) to afford the product.

J: To a solution of 1-(3-hydroxyphenyl)ethanone (1.0 mmol) in DCM (0.38 M) was added 1H-imidazole (2.0 equiv) and chlorotriisopropylsilane (1.8 equiv). The resulting mixture was stirred at rt for 6 hrs before being diluted with water and extracted with DCM (3×). The combined organic layers were dried over MgSO4, filtered and concentrated in vacuo to give the desired product which was taken on without further attempts at purification.

K: To a solution of (Z)-ethyl 2-hydroxy-4-oxo-4-(oxy)phenyl)but-2-enoate in THF (0.057 M) at 0° C. was added a solution of TBAF (3.0 equiv) in THF. The reaction mixture was stirred for 30 min at 0° C. before being warmed to rt and stirred for an additional 35 min. At this time the resulting solution was diluted with water and extracted with EtOAc (4×). The combined organic layers were washed with brine, dried over MgSO4, filtered and concentrated in vacuo.

Purification was achieved via flash column chromatography on SiO2 (Hexanes/EtOAc: 1/1) to afford the desired product which was taken on without further attempts at purification.

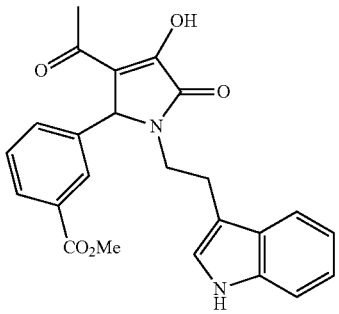 [SMILES: COC(=O)c1cccc(C2C(C(C)=O)=C(O)C(=O)N2CCc2c[nH]c3ccccc23)c1]

Methyl 3-(1-2-(1H-indol-3-yl)ethyl)-3-acetyl-4-hydroxy-5-oxo-2,5-dihydro-1H-pyrrol-2-yl)benzoate (1616-02). Compound 1616-02 was prepared via the general procedure A from methyl 3-formylbenzoate (0.50 g, 3.1 mmol), tryptamine (0.49 g, 3.1 mmol) and methyl acetopyruvate (0.44 g, 3.1 mmol) to yield a pale pink solid (0.77 g, 60%). $^1$H NMR (400 MHz, DMSO-d$^6$) δ 10.82 (s, 1H), 7.87 (d, J=7.6 Hz, 1H), 7.73 (s, 1H), 7.45 (t, J=7.2 Hz, 1H), 7.39-7.26 (mult, 3H), 7.10 (d, J=2.0 Hz, 1H), 7.05 (t, J=7.2 Hz, 1H), 6.89 (t, J=8.0 Hz, 1H), 5.24 (s, 1H), 3.85-3.76 (mult, 4H), 2.98-2.91 (mult, 1H), 2.87-2.80 (mult, 1H), 2.72-2.65 (mult, 1H), 2.72 (s, 3H).

tert-Butyl-4-formylbenzoate (1616-03a)

To a solution of 4-formylbenzoic acid (1.0 g, 6.7 mmol) in refluxing benzene (12.6 mL, 0.50 M) was added 1,1-di-tert-butoxy-N,Ndimethylmethanamine (6.4 mL, 26.6 mmol, 4.0 equiv) over a period of 1 hr. The reaction was then allowed to continue refluxing for 30 min before being cooled to rt and diluted with water. After washing with saturated sodium bicarbonate (2×), the combined organic layers were washed with brine, dried over MgSO4, filtered and concentrated in vacuo. The crude product was then purified using flash column chromatography on SiO2 (Hexanes/EtOAc: 6/1) to yield a white solid (1.1 g, 81%).

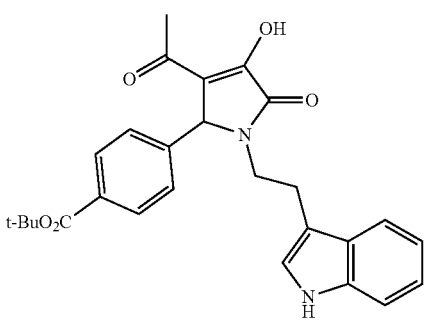

tert-Butyl 4-(1-(2-(1H-indol-3-yl)ethyl)-3-acetyl-4-hydroxy-5-oxo-2,5-dihydro-1H-pyrrol-2-yl)benzoate (1616-03). Compound 1616-03 was prepared via the general procedure A from tert-butyl-4-formylbenzoate (0.50 g, 2.4 mmol), tryptamine (0.39 g, 2.4 mmol) and methyl acetopyruvate (0.35 g, 2.4 mmol) to yield a pale yellow solid (0.92 g, 83%). $^1$H NMR (400 MHz, DMSO-d$^6$) δ 10.83 (s, 1H), 7.81 (d, J=8.4 Hz, 2H), 7.33-7.22 (mult, 4H), 7.10 (d, J=2.0 Hz, 1H), 7.05 (t, J=7.2 Hz, 1H), 6.91 (t, J=7.6 Hz, 1H), 5.17 (s, 1H), 3.83-3.76 (mult, 1H), 2.96-2.89 (mult, 1H), 2.86-2.81 (mult, 1H), 2.79-2.67 (mult, 1H), 2.26 (s, 3H), 1.53 (s, 9H).

Methyl 4-formyl-3-methoxybenzoate (1616-04a)

To a solution of 4-formyl-3-hydroxybenzoic acid (0.5 g, 3.0 mmol) in DMSO (5.2 mL, 0.60 M) was added finely ground potassium carbonate (2.6 g, 19 mmol) and methyl iodide (0.65 mL, 3.0 mmol, 1.0 equiv). The reaction mixture was allowed to stir at rt for 3 hrs before being diluted with water and extracted into EtOAc. The organic layer was washed with water (2×), dried over MgSO4, filtered and concentrated in vacuo. The crude product was then purified using flash column chromatography on SiO2 (5% MeOH/DCM) to yield a white solid (0.34 g, 58%).

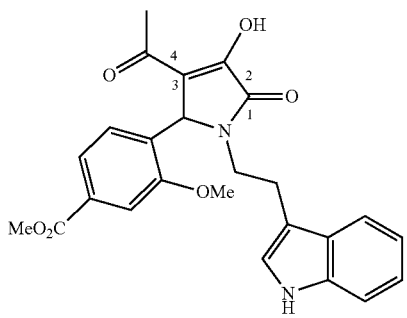 [SMILES: COC(=O)c1ccc(C2C(C(C)=O)=C(O)C(=O)N2CCc2c[nH]c3ccccc23)c(OC)c1]

Methyl 4-(1-(2-(1H-indol-3-yl)ethyl)-3-acetyl-4-hydroxy-5-oxo-2,5-dihydro-1H-pyrrol-2-yl)-3-methoxybenzoate (1616-04). Compound 1616-04 was prepared via the general procedure A from methyl 4-formyl-3-methoxybenzoate (0.20 g, 1.0 mmol), tryptamine (0.17 g, 1.0 mmol) and methyl acetopyruvate (0.15 g, 1.0 mmol) to yield an off-white solid (0.16 g, 36%). $^1$H NMR (600 MHz, DMSO-d$^6$, 56° C.) δ 10.68 (s, 1H), 7.53 (s, 1H), 7.48 (dd, J=1.6 Hz, J=8.0 Hz, 1H), 7.32-7.28 (mult, 2H), 7.06-7.02 (mult, 3H), 6.92 (td, J=7.2 Hz, J=0.8 Hz, 1H), 5.59 (s, 1H), 3.86 (s, 6H), 3.81-3.72 (mult, 1H), 2.97-2.85 (mult, 2H), 2.84-2.69 (mult, 1H), 2.27 (s, 3H).

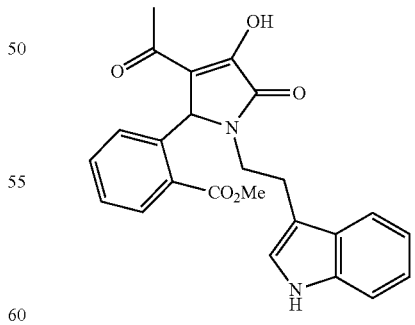

Methyl 2-(1-(2-(1H-indol-3-yl)ethyl)-3-acetyl-4-hydroxy-5-oxo-2,5-dihydro-1H-pyrrol-2-yl)benzoate (1616-05). Compound 1616-05 was prepared via the general procedure A from methyl 2-formylbenzoate (0.10 g, 0.61 mmol), tryptamine (0.098 g, 0.61 mmol) and methyl acetopyruvate (0.088 g, 0.61 mmol) to yield a white solid (0.18 g, 72%). $^1$H NMR (400 MHz, DMSO-d$^6$) δ 10.82 (s, 1H), 7.87 (d, J=7.6 Hz, 1H), 7.72 (s, 1H), 7.46 (t, J=7.6 Hz, 1H), 7.38 (d, J=7.6 Hz, 1H), 7.32-7.25 (mult, 2H), 7.10 (d, J=1.6 Hz, 1H), 7.02 (t, J=7.6 Hz, 1H), 6.89 (t, J=7.6 Hz, 1H), 5.24 (s, 1H), 3.86 (s, 3H), 3.82-3.75 (mult, 1H), 2.97-2.90 (mult, 1H), 2.86-2.79 (mult, 1H), 2.71-2.66 (mult, 1H), 2.27 (s, 3H).

brown solid (0.10 g, 27%). $^1$H NMR (400 MHz, DMSO-d$^6$) δ 10.82 (s, 1H), 10.49 (s, 1H), 7.68 (dd, J=8.0 Hz, J=2.4 Hz, 1H), 7.34-7.30 (mult, 2H), 7.10 (s, 1H), 7.05 (t, J=6.8 Hz, 1H), 6.92 (t, J=6.8 Hz, 1H), 6.84 (s, 1H), 6.64 (d, J=8.0 Hz, 1H), 5.12 (s, 1H), 3.86 (s, 3H), 3.83-3.76 (mult, 1H), 2.98-2.83 (mult, 2H), 2.75-2.68 (mult, 1H), 2.27 (s, 3H).

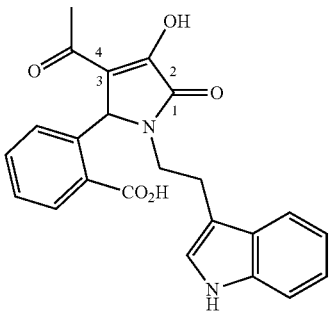 [SMILES: CC(=O)C1=C(O)C(=O)N(CCc2c[nH]c3ccccc23)C1c1ccccc1C(=O)O]

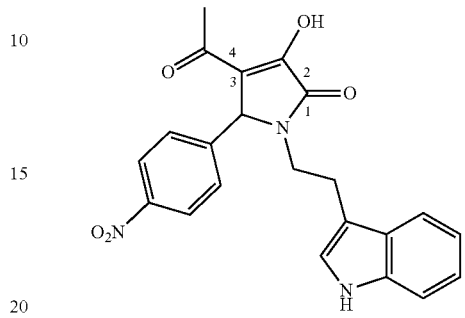

2-(1-(2-(1H-Indol-3-yl)ethyl)-3-acetyl-4-hydroxy-5-oxo-2,5-dihydro-1H-pyrrol-2-yl) benzoic acid (1616-06). Compound 1616-06 was prepared via the general procedure A from methyl 2-formylbenzoate (0.5 g, 3.1 mmol), tryptamine (0.49 g, 3.1 mmol) and methyl acetopyruvate (0.44 g, 3.1 mmol). After stirring at rt for 12 hrs, 2M NaOH was added until an orange solid began to crash out. The solution was filtered and washed with Et$_2$O. Purification was achieved via recrystallization from EtOAc/Hexanes to give an orange solid (0.59 g, 48%). $^1$H NMR (400 MHz, DMSO-d$^6$) δ 13.41 (br s, 1H), 10.80 (s, 1H), 7.85 (d, J=7.6 Hz, 1H), 7.46 (td, J=1.2 Hz, J=7.2 Hz, 1H), 7.37 (dt, J=1.2 Hz, J=7.2 Hz, 1H), 7.30 (t, J=7.6 Hz, 2H), 7.08 (d, J=2.0 Hz, 1H), 7.02 (t, J=7.2 Hz, 1H), 6.95 (d, J=8.0 Hz, 1H), 6.90 (dt, J=0.8 Hz, J=7.2 Hz, 1H), 6.60 (s, 1H), 3.90-3.82 (mult, 1H), 3.00-2.85 (mult, 2H), 2.80-2.72 (mult, 1H), 2.42 (s, 3H).

Methyl 2-hydroxy-4-vinylbenzoate (1616-07a). Compound 1616-07a was prepared via Procedure B from methyl 2-hydroxy-4-iodobenzoate (1.0 g, 3.6 mmol) to yield a clear oil (0.51 g, 80%).

Methyl 4-formyl-2-hydroxybenzoate (1616-07b). Compound 1616-07b was prepared via Procedure C from 1616-07a (0.49 g, 2.8 mmol) to afford a white solid (0.30 g, 60%).

1-(2-(1H-Indol-3-yl)ethyl)-4-acetyl-3-hydroxy-5-(4-nitrophenyl)-1H-pyrrol-2(5H)-one (1616-08). Compound 1616-08 was prepared via the general procedure A from 4-nitrobenzaldehyde (0.50 g, 3.3 mmol), tryptamine (0.53 g, 3.3 mmol) and methyl acetopyruvate (0.48 g, 3.3 mmol) to yield a pale yellow solid (1.0 g, 75%). $^1$H NMR (400 MHz, DMSO-d$^6$) δ 12.62 (br s, 1H), 10.82 (s, 1H), 8.10 (d, J=8.8 Hz, 2H), 7.37 (d, J=8.8 Hz, 2H), 7.31 (d, J=8.4 Hz, 2H), 7.09 (d, J=1.6 Hz, 1H), 7.04 (t, J=8.0 Hz, 1H), 6.91 (t, J=7.6 Hz, 1H), 5.26 (s, 1H), 3.85-3.78 (mult, 1H), 2.97-2.84 (mult, 2H), 2.80-2.77 (mult, 1H), 2.27 (s, 3H); $^{13}$C NMR (150 MHz, DMSO-d$^6$) δ 191.6, 165.2, 154.7, 147.1, 144.9, 136.2, 129.0, 126.8, 123.5, 122.9, 121.0, 118.2, 118.0, 111.4, 110.7, 59.4, 41.0, 29.8, 23.5 (Note: Carbon 3 is absent); mp 142-150° C.; HRMS (APCI) Calcd for C$_{22}$H$_{19}$N$_3$O$_5$ 406.1398. found 406.1395 [M+H]$^+$.

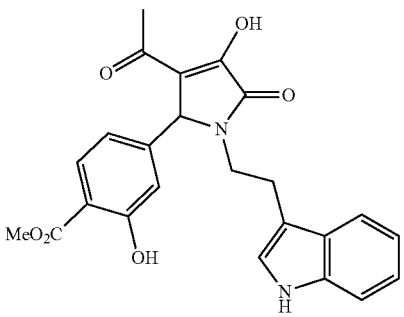 [SMILES: COC(=O)c1ccc(C2C(C(C)=O)=C(O)C(=O)N2CCc2c[nH]c3ccccc23)cc1O]

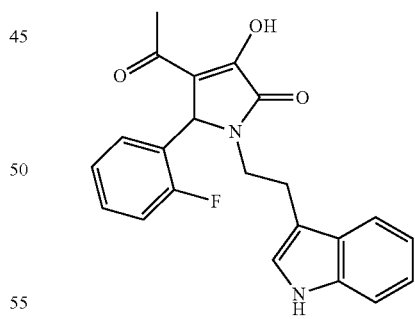

Methyl 4-(1-(2-(1H-indol-3-yl)ethyl)-3-acetyl-4-hydroxy-5-oxo-2,5-dihydro-1H-pyrrol-2-yl)-2-hydroxybenzoate (1616-07). Compound 1616-07 was prepared via the general procedure A from methyl 4-formyl-2-hydroxybenzoate (0.15 g, 0.83 mmol), tryptamine (0.13 g, 0.83 mmol) and methyl acetopyruvate (0.12 g, 0.83 mmol) to yield a 1-(2-(1H-Indol-3-yl)ethyl)-4-acetyl-5-(2-fluorophenyl)-3-hydroxy-1H-pyrrol-2(5H)-one (1616-09). Compound 1616-09 was prepared via the general procedure A from 2-fluorobenzaldehyde (0.42 mL, 4.0 mmol), tryptamine (0.65 g, 4.0 mmol) and methyl acetopyruvate (0.58 g, 4.0 mmol) to yield a cream colored solid (1.0 g, 67%). $^1$H NMR (400 MHz, DMSO-d$^6$) δ 12.40 (br s, 1H), 10.83 (s, 1H), 7.38-7.27 (mult, 3H), 7.22-7.03 (mult, 5H), 6.92 (t, J=6.8 Hz, 1H), 5.41 (s, 1H), 3.83-3.76 (mult, 1H), 2.98-2.86 (mult, 2H), 2.85-2.67 (mult, 1H), 2.29 (s, 3H).

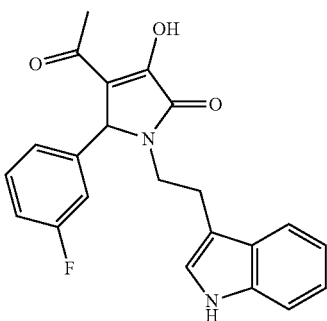 [SMILES: CC(=O)C1=C(O)C(=O)N(CCc2c[nH]c3ccccc23)C1c1cccc(F)c1]

1-(2-(1H-Indol-3-yl)ethyl)-4-acetyl-5-(3-fluorophenyl)-3-hydroxy-1H-pyrrol-2(5H)-one (1616-10). Compound 1616-10 was prepared via the general procedure A from 3-fluorobenzaldehyde (0.43 mL, 4.0 mmol), tryptamine (0.65 g, 4.0 mmol) and methyl acetopyruvate (0.58 g, 4.0 mmol) to yield a light brown solid (0.87 g, 57%). $^1$H NMR (400 MHz, DMSO-d$^6$) δ 12.42 (br s, 1H), 10.83 (s, 1H), 7.37-7.31 (mult, 3H), 7.13-7.04 (mult, 3H), 6.98-6.91 (mult, 3H), 5.13 (s, 1H), 3.84-3.77 (mult, 1H), 2.98-2.82 (mult, 2H), 2.75-2.71 (mult, 1H), 2.28 (s, 3H).

Methyl 4-formyl-2-methoxybenzoate (1616-11a). Compound 1616-11a was prepared via Procedure E from methyl 2-methoxy-4-methylbenzoate (0.50 g, 2.8 mmol) to yield a yellow oil (0.21 g, 38%).

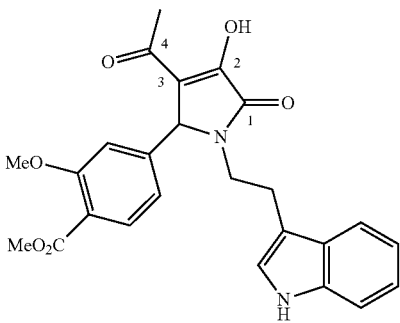 [SMILES: COC(=O)c1ccc(C2C(C(C)=O)=C(O)C(=O)N2CCc2c[nH]c3ccccc23)cc1OC]

Methyl 4-(1-(2-(1H-indol-3-yl)ethyl)-3-acetyl-4-hydroxy-5-oxo-2,5-dihydro-1H-pyrrol-2-yl)-2-methoxybenzoate (1616-11). Compound 1616-11 was prepared via the general procedure A from methyl 4-formyl-2-methoxybenzoate (0.1 g, 0.52 mmol), tryptamine (0.083 g, 0.52 mmol) and methyl acetopyruvate (0.074 g, 0.52 mmol) to yield a cream colored solid (0.17 g, 74%). $^1$H NMR (600 MHz, DMSO-d$^6$) δ 10.83 (s, 1H), 7.55 (d, J=8.0 Hz, 1H), 7.34-7.31 (mult, 2H), 7.11 (s, 1H), 7.06 (t, J=6.8 Hz, 1H), 6.94-6.91 (mult, 2H), 6.70 (d, J=8.0 Hz, 1H), 5.14 (s, 1H), 3.83-3.76 (mult, 7H), 2.99-2.84 (mult, 2H), 2.75-2.69 (mult, 1H), 2.28 (s, 3H).

Methyl 3-hydroxy-4-vinylbenzoate (1616-12a). Compound 1616-12a was prepared via Procedure B from methyl 3-hydroxy-4-iodobenzoate (0.5 g, 1.8 mmol) to yield a pale yellow solid (0.22 g, 68%).

Methyl 4-formyl-3-hydroxybenzoate (1616-12b). Compound 1616-12b was prepared via Procedure C from 1616-12a (0.22 g, 1.2 mmol) to afford a pale yellow solid (0.19 g, 87%).

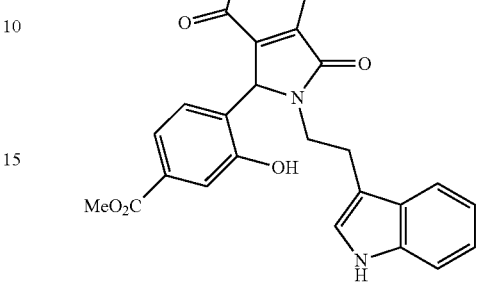

Methyl 4-(1-(2-(1H-indol-3-yl)ethyl)-3-acetyl-4-hydroxy-5-oxo-2,5-dihydro-1H-pyrrol-2-yl)-3-hydroxybenzoate (1616-12). Compound 1616-12 was prepared via the general procedure A from methyl 4-formyl-3-hydroxybenzoate (0.1 g, 0.56 mmol), tryptamine (0.089 g, 0.52 mmol) and methyl acetopyruvate (0.080 g, 0.56 mmol) to yield an off-white solid (0.020 g, 8%). $^1$H NMR (400 MHz, DMSO-d$^6$) δ 10.68 (s, 1H), 10.07 (br s, 1H), 7.47 (s, 1H), 7.35-7.29 (mult, 3H), 7.05-7.02 (mult, 3H), 6.91 (t, J=10.8 Hz, 1H), 5.58 (s, 1H), 3.83 (s, 3H), 3.80-3.74 (mult, 1H), 3.02-2.88 (mult, 2H), 2.76-2.68 (mult, 1H), 2.27 (s, 3H).

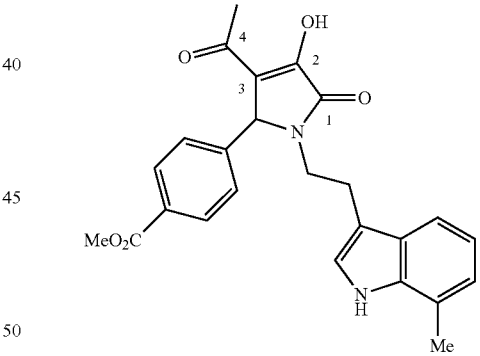

Methyl 4-(3-acetyl-4-hydroxy-1-(2-(7-methyl-1H-indol-3-yl)ethyl)-5-oxo-2,5-dihydro-1H-pyrrol-2-yl)benzoate (1616-13). Compound 1616-13 was prepared via the general procedure A from methyl 4-formylbenzoate (0.094 g, 0.57 mmol), 2-(7-methyl-1H-indol-3-yl) ethanamine (0.10 g, 0.57 mmol) and methyl acetopyruvate (0.083 g, 0.57 mmol) to yield a white solid (0.16 g, 66%). $^1$H NMR (400 MHz, DMSO-d$^6$) δ 12.50 (br s, 1H), 10.78 (s, 1H), 7.88 (d, J=8.0 Hz, 2H), 7.26 (d, J=8.4 Hz, 2H), 7.12-7.07 (mult, 2H), 6.83-6.82 (mult, 2H), 5.20 (s, 1H), 3.83-3.76 (mult, 4H), 2.98-2.80 (mult, 2H), 2.80-2.66 (mult, 1H), 2.41 (s, 3H), 2.26 (s, 3H).

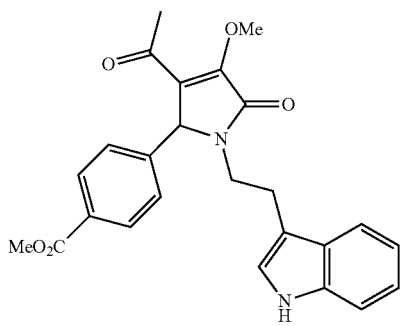

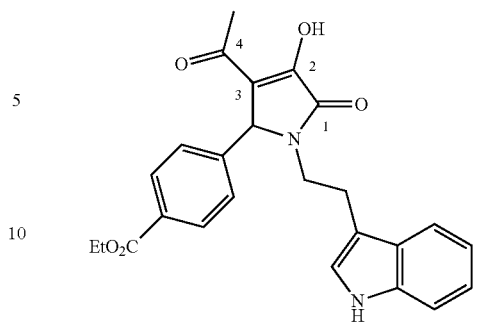

Methyl 4-(1-(2-(1H-indol-3-yl)ethyl)-3-acetyl-4-methoxy-5-oxo-2,5-dihydro-1H-pyrrol-2-yl)benzoate (1616-14). To a solution of 1616 (0.50 g, 1.2 mmol) in DCM:MeOH (1:1, 0.13M) was added (diazomethyl)trimethylsilane (0.72 ml, 1.4 mmol). The reaction mixture continued to stir at rt for 5 hrs before being concentrated in vacuo. The crude residue was then purified using flash column chromatography on $SiO_2$ (3% MeOH/DCM) to yield a pale yellow solid (0.24 g, 46%). $^1$H NMR (400 MHz, DMSO-d$^6$) δ 10.82 (s, 1H), 7.88 (dd, J=1.6 Hz, J=8.0 Hz, 2H), 7.33-7.24 (mult, 4H), 7.09-7.03 (mult, 2H), 6.92 (t, J=7.6 Hz, 1H), 5.20 (s, 1H), 4.36 (s, 3H), 3.84 (s, 3H), 3.80-3.71 (mult, 1H), 2.96-2.89 (mult, 1H), 2.84-2.77 (mult, 1H), 2.72-2.63 (mult, 1H), 2.25 (s, 3H).

Isopropyl 4-formylbenzoate (1616-15a). Compound 1616-15a was prepared via Procedure D from 4-formylbenzoic acid (1.0 g, 6.7 mmol) and 2-iodopropane (1.7 ml, 17 mmol, 2.5 equiv) to yield a white solid (0.30 g, 24%).

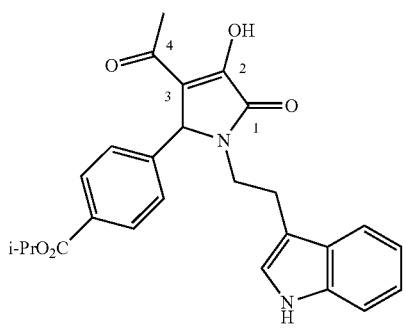

Isopropyl 4-(1-(2-(1H-indol-3-yl)ethyl)-3-acetyl-4-hydroxy-5-oxo-2,5-dihydro-1H-pyrrol-2-yl)benzoate (1616-15). Compound 1616-15 was prepared via the general procedure A from isopropyl 4-formylbenzoate (0.20 g, 1.0 mmol), tryptamine (0.17 g, 1.0 mmol) and methyl acetopyruvate (0.15 g, 1.0 mmol) to yield an orange solid (0.028 g, 6%). $^1$H NMR (400 MHz, DMSO-d$^6$) δ 10.70 (s, 1H), 7.86 (d, J=8.4 Hz, 2H), 7.33-7.23 (mult, 3H), 7.11-7.00 (mult, 3H), 6.91 (t, J=7.6 Hz, 1H), 5.16-5.11 (mult, 2H), 3.82-3.77 (mult, 1H), 3.02-2.85 (mult, 2H), 2.76-2.71 (mult, 1H), 2.26 (s, 3H), 1.32 (s, 3H), 1.31 (s, 3H).

Ethyl 4-formylbenzoate (1616-16a). Compound 1616-16a was prepared via Procedure D from 4-formylbenzoic acid (1.0 g, 6.7 mmol) and iodoethane (1.3 ml, 17 mmol, 2.5 equiv) to yield a yellow oil (1.0 g, 87%).

Ethyl 4-(1-(2-(1H-indol-3-yl)ethyl)-3-acetyl-4-hydroxy-5-oxo-2,5-dihydro-1H-pyrrol-2-yl)benzoate (1616-16). Compound 1616-16 was prepared via the general procedure A from ethyl 4-formylbenzoate (0.20 g, 1.1 mmol), tryptamine (0.18 g, 1.1 mmol) and methyl acetopyruvate (0.16 g, 1.1 mmol) to yield a pale pink solid (0.20 g, 42%). $^1$H NMR (400 MHz, DMSO-d$^6$) δ 12.48 (br s, 1H), 10.82 (s, 1H), 7.87 (d, J=8.4 Hz, 2H), 7.33-7.24 (mult, 4H), 7.09 (d, J=2.4 Hz, 1H), 7.05 (t, J=7.2 Hz, 1H), 6.91 (t, J=7.6 Hz, 1H), 5.18 (s, 1H), 4.30 (q, J=7.2 Hz, 2H), 3.83-3.76 (mult, 1H), 2.97-2.89 (mult, 1H), 2.87-2.80 (mult, 1H), 2.74-2.67 (mult, 1H), 2.26 (s, 3H), 1.30 (t, J=7.2 Hz, 3H).

Methyl 3-chloro-4-formylbenzoate (1616-17a). Compound 1616-17a was prepared via Procedure E from methyl 3-chloro-4-methylbenzoate (1.0 g, 5.4 mmol) to yield a white solid (0.61 g, 63%).

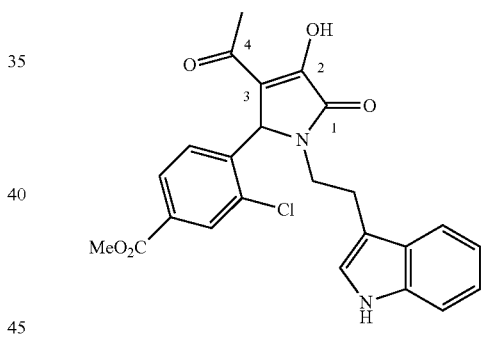

Methyl 4-(1-(2-(1H-indol-3-yl)ethyl)-3-acetyl-4-hydroxy-5-oxo-2,5-dihydro-1H-pyrrol-2-yl)-3-chlorobenzoate (1616-17). Compound 1616-17 was prepared via the general procedure A from methyl 3-chloro-4-formylbenzoate (0.10 g, 0.50 mmol), tryptamine (0.081 g, 0.50 mmol) and methyl acetopyruvate (0.073 g, 0.50 mmol) to yield a pale yellow solid (0.080 g, 35%). $^1$H NMR (400 MHz, DMSO-d$^6$) δ 12.50 (br s, 1H), 10.81 (s, 1H), 7.95 (d, J=1.6 Hz, 1H), 7.76 (dd, J=1.2 Hz, J=8.0 Hz, 1H), 7.29 (d, J=8.4 Hz, 2H), 7.09-7.01 (mult, 3H), 6.91 (t, J=7.6 Hz, 1H), 5.68 (s, 1H), 3.85 (s, 3H), 3.80-3.73 (mult, 1H), 2.97-2.84 (mult, 2H), 2.77-2.72 (mult, 1H), 2.28 (s, 3H).

Methyl 4-formyl-3-methylbenzoate (1616-18a). To a solution of methyl 4-iodo-3-methylbenzoate (1.0 g, 3.6 mmol) in THF (24 mL, 0.15 M) at −15° C. was added isopropylmagnesium chloride (7.2 ml, 14.5 mmol, 4.0 equiv). The reaction mixture was allowed to continue stirring at −15° C. for 2 hrs before N,N-dimethylformamide (1.4 ml, 18 mmol, 5.0 equiv) was added. The mixture was warmed to room temperature over a period of 1 hr. At this time the reaction was quenched with HCl and extracted with EtOAc (3×). The combined organic layers were washed with brine and dried over MgSO4, filtered and concentrated in vacuo.

Purification was achieved using flash column chromatography on SiO2 (Hexanes/EtOAc: 6/1) to yield a white solid (0.45 g, 70%) which was taken on without further purification.

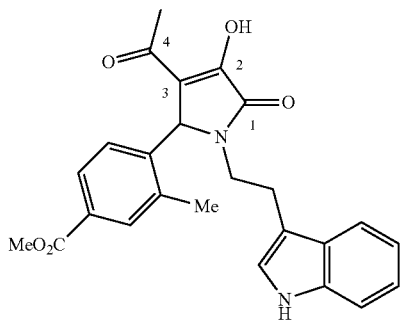 [SMILES: COC(=O)c1ccc(C2C(C(C)=O)=C(O)C(=O)N2CCc2c[nH]c3ccccc23)c(C)c1]

Methyl 4-(1-(2-(1H-indol-3-yl)ethyl)-3-acetyl-4-hydroxy-5-oxo-2,5-dihydro-1H-pyrrol-2-yl)-3-methylbenzoate (1616-18). Compound 1616-18 was prepared via the general procedure A from methyl 4-formyl-3-methylbenzoate (0.10 g, 0.56 mmol), tryptamine (0.090 g, 0.56 mmol) and methyl acetopyruvate (0.081 g, 0.56 mmol) to yield an orange solid (0.12 g, 50%). $^1$H NMR (600 MHz, DMSO-d$^6$) δ 10.83 (s, 1H), 7.75 (s, 1H), 7.66 (d, J=8.4 Hz, 1H), 7.31 (d, J=8.4 Hz, 1H), 7.22 (d, J=8.4 Hz, 1H), 7.09 (d, J=1.8 Hz, 1H), 7.04 (t, J=7.2 Hz, 1H), 6.90 (t, J=7.8 Hz, 1H), 6.84 (d, J=8.4 Hz, 1H), 5.27 (s, 1H), 3.81 (s, 3H), 3.75 (dt, J=8.4 Hz, J=13.8 Hz, 1H), 2.94-2.89 (mult, 1H), 2.76-2.69 (mult, 2H), 2.31 (s, 3H), 2.25 (s, 3H).

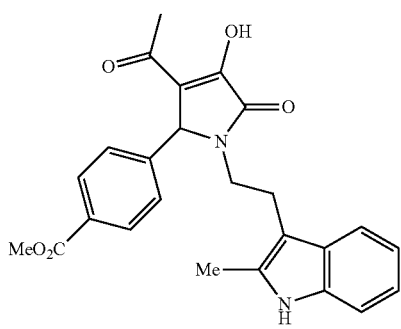 [SMILES: COC(=O)c1ccc(C2C(C(C)=O)=C(O)C(=O)N2CCc2c(C)[nH]c3ccccc23)cc1]

Methyl 4-(3-acetyl-4-hydroxy-1-(2-(2-methyl-1H-indol-3-yl)ethyl)-5-oxo-2,5-dihydro-1H-pyrrol-2-yl)benzoate (1616-19). Compound 1616-19 was prepared via the general procedure A from methyl 4-formylbenzoate (0.094 g, 0.57 mmol), 2-(2-methyl-1H-indol-3-yl)ethanamine (0.10 g, 0.57 mmol) and methyl acetopyruvate (0.083 g, 0.57 mmol) to yield a cream colored solid (0.18 g, 73%). $^1$H NMR (600 MHz, DMSO-d$^6$) δ 10.73 (s, 1H), 7.85 (d, J=9.0 Hz, 2H), 7.21 (d, J=7.8 Hz, 1H), 7.18-7.15 (mult, 3H), 6.97 (t, J=7.8 Hz, 1H), 6.86 (t, J=7.8 Hz, 1H), 5.03 (s, 1H), 3.83 (s, 3H), 3.64-3.59 (mult, 1H), 2.92-2.87 (mult, 1H), 2.77-2.72 (mult, 1H), 2.60-2.56 (mult, 1H), 2.26 (s, 3H), 2.17 (s, 3H).

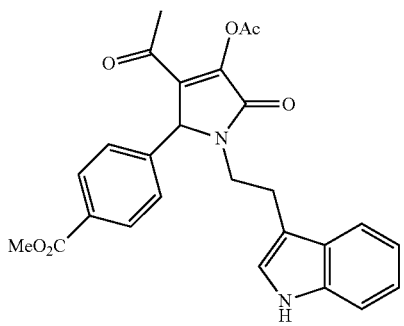 [SMILES: COC(=O)c1ccc(C2C(C(C)=O)=C(OC(C)=O)C(=O)N2CCc2c[nH]c3ccccc23)cc1]

Methyl 4-(1-(2-(1H-indol-3-yl)ethyl)-4-acetoxy-3-acetyl-5-oxo-2,5-dihydro-1H-pyrrol-2-yl)benzoate (1616-20). To a solution of 1616 (0.50 g, 1.2 mmol) in DCM (11 ml, 0.11 M) was added acetic anhydride (0.14 ml, 1.4 mmol, 1.2 equiv) and pyridine (0.14 ml, 1.8 mmol, 1.5 equiv). The reaction mixture was stirred at rt for 6½ hrs before being concentrated in vacuo. The crude material was then purified by flash column chromatography on SiO$_2$ (3% MeOH/DCM). Additional purification was achieved using HPLC (ACN/Water: 3/1, isocratic) to give a yellow oil (0.038 g, 7%). $^1$H NMR (400 MHz, CDCl$_3$) δ 8.06 (s, 1H), 7.94-7.92 (mult, 2H), 7.38 (d, J=8.4 Hz, 2H), 7.21 (t, J=8.0 Hz, 1H), 7.10-7.05 (mult, 3H), 6.98 (d, J=2.0 Hz, 1H), 4.93 (s, 1H), 4.07-4.00 (mult, 1H), 3.91 (s, 3H), 3.08-2.89 (mult, 3H), 2.47 (s, 3H), 2.26 (s, 3H).

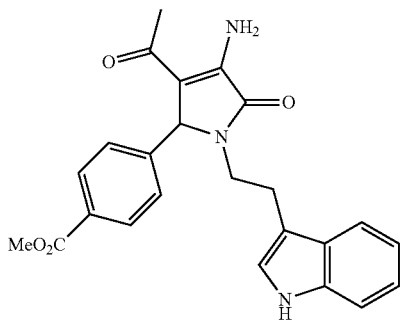 [SMILES: COC(=O)c1ccc(C2C(C(C)=O)=C(N)C(=O)N2CCc2c[nH]c3ccccc23)cc1]

Methyl 4-(1-(2-(1H-indol-3-yl)ethyl)-3-acetyl-4-amino-5-oxo-2,5-dihydro-1H-pyrrol-2-yl)benzoate (1616-21). To a solution of 1616-00 (0.50 g, 1.2 mmol) in 2-methoxyethanol (8.36 ml, 0.14 M) was added ammonium formate (0.11 ml, 2.2 mmol, 1.8 equiv). The reaction mixture was refluxed for 3 hrs before being concentrated in vacuo, ground with a mortar and pestle and triturated with Et$_2$O. Further purification was achieved via flash column chromatography on SiO$_2$ (MeOH/DCM: 1/6) to yield a pale yellow solid (0.070 g, 14%). $^1$H NMR (400 MHz, CDCl$_3$, 56° C.) δ 10.02 (br s, 1H), 8.36 (br s, 1H), 7.92 (d, J=8.0 Hz, 2H), 7.39-7.34 (mult, 2H), 7.17 (t, J=7.6 Hz, 1H), 7.08-7.02 (mult, 3H), 6.97 (s, 1H), 6.44 (br s, 1H), 4.77 (s, 1H), 4.04-3.97 (mult, 1H), 3.91 (s, 3H), 3.09-2.99 (mult, 2H), 2.92-2.85 (mult, 1H), 1.56 (s, 3H).

Methyl 4-formyl-2-methylbenzoate (1616-23b). Compound 1616-23b was prepared via Procedure G from 1616-23a (1.0 g, 4.4 mmol) to yield a clear oil (0.15 g, 19%) which was taken on without further purification.

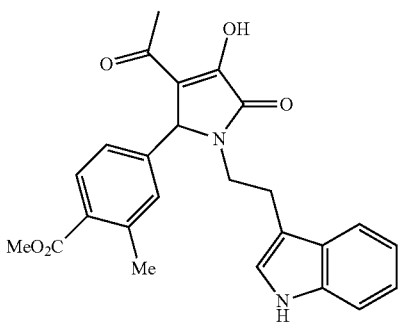 [SMILES: COC(=O)c1ccc(C2C(C(C)=O)=C(O)C(=O)N2CCc2c[nH]c3ccccc23)cc1C]

Methyl 4-(1-(2-(1H-indol-3-yl)ethyl)-3-acetyl-4-hydroxy-5-oxo-2,5-dihydro-1H-pyrrol-2-yl)-2-methylbenzoate (1616-23). Compound 1616-23 was prepared via the general procedure from methyl 4-formyl-2-methylbenzoate (0.10 g, 0.56 mmol), tryptamine (0.090 g, 0.56 mmol) and methyl acetopyruvate (0.081 g, 0.56 mmol) to yield a pale orange solid (0.13 g, 53%). $^1$H NMR (400 MHz, CDCl$_3$) δ 8.14 (s, 1H), 7.83 (d, J=8.4 Hz, 1H), 7.40-7.36 (mult, 2H), 7.23 (t, J=7.6 Hz, 1H), 7.11 (t, J=7.6 Hz, 1H), 7.00 (s, 1H), 6.83 (d, J=7.6 Hz, 1H), 6.74 (s, 1H), 4.76 (s, 1H), 4.07-4.02 (mult, 1H), 3.90 (s, 3H), 3.11-2.93 (mult, 3H), 2.51 (s, 3H), 1.98 (s, 3H).

Methyl 4-bromo-2-chlorobenzoate (1616-24a). Compound 1616-24a was prepared via Procedure H from 4-bromo-2-chlorobenzoic acid (2.0 g, 8.5 mmol) to give an orange oil (2.1 g, 99%).

Methyl 2-chloro-4-formylbenzoate (1616-24b). Compound 1616-24b was prepared via Procedure G from 1616-24a (1.0 g, 4.0 mmol) to yield a yellow oil (0.19 g, 24%) which was taken on without further purification.

Methyl 4-(1-(2-(1H-indol-3-yl)ethyl)-3-acetyl-4-hydroxy-5-oxo-2,5-dihydro-1H-pyrrol-2-yl)-2-chlorobenzoate (1616-24). Compound 1616-24 was prepared via the general procedure A from methyl 2-chloro-4-formylbenzoate (0.09 g, 0.45 mmol), tryptamine (0.073 g, 0.45 mmol) and methyl acetopyruvate (0.065 g, 0.45 mmol) to yield a pale orange residue (0.14 g, 68%). $^1$H NMR (400 MHz, DMSO-d$^6$) δ 10.85 (s, 1H), 7.71 (d, J=8.0 Hz, 1H), 7.40-7.23 (mult, 4H), 7.14-7.03 (mult, 2H), 6.93 (t, J=7.6 Hz, 1H), 5.13 (s, 1H), 3.83-3.78 (mult, 4H), 2.98-2.82 (mult, 2H), 2.75-2.68 (mult, 1H), 2.27 (s, 3H).

Methyl 2-fluoro-4-formylbenzoate (1616-25b). Compound 1616-25b was prepared via Procedure G from 1616-25a (0.91 g, 3.9 mmol) to yield a white solid (0.080 g, 11%) which was taken on without further purification.

Methyl 4-bromo-2-fluorobenzoate (1616-25a). Compound 1616-25a was prepared via Procedure H from 4-bromo-2-fluorobenzoic acid (1.0 g, 4.6 mmol) to give an off white solid (0.93 g, 88%).

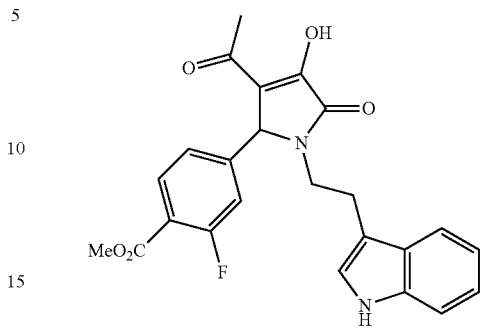

Methyl 4-(1-(2-(1H-indol-3-yl)ethyl)-3-acetyl-4-hydroxy-5-oxo-2,5-dihydro-1H-pyrrol-2-yl)-2-fluorobenzoate (1616-25). Compound 1616-25 was prepared via the general procedure A from methyl 2-fluoro-4-formylbenzoate (0.08 g, 0.44 mmol), tryptamine (0.070 g, 0.44 mmol) and methyl acetopyruvate (0.063 g, 0.44 mmol) to yield a pale orange solid (0.096 g, 50%). $^1$H NMR (400 MHz, CDCl$_3$) δ 8.42 (s, 1H), 7.81 (t, J=7.6 Hz, 1H), 7.40-7.27 (mult, 2H), 7.20 (t, J=7.2 Hz, 1H), 7.14-7.06 (mult, 1H), 6.95 (d, J=1.2 Hz, 1H), 6.78 (dd, J=1.2 Hz, J=7.6 Hz, 1H), 6.70 (dd, J=1.2 Hz, J=10.8 Hz, 1H), 4.80 (s, 1H), 4.09-4.03 (mult, 1H), 3.92 (s, 3H), 3.10-2.96 (mult, 3H), 2.19 (s, 3H).

Methyl 4-bromo-3-fluorobenzoate (1616-26a). Compound 1616-26a was prepared via Procedure H from 4-bromo-3-fluorobenzoic acid (2.0 g, 9.1 mmol) to give a yellow oil (2.1 g, 99%).

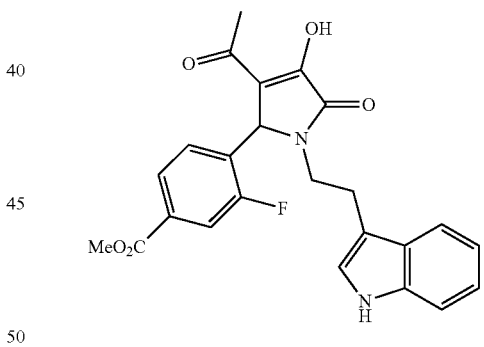

Methyl 4-(1-(2-(1H-indol-3-yl)ethyl)-3-acetyl-4-hydroxy-5-oxo-2,5-dihydro-1H-pyrrol-2-yl)-3-fluorobenzoate (1616-26). Methyl 3-fluoro-4-formylbenzoate was combined with tryptamine (0.11 g, 0.67 mmol) and methyl acetopyruvate (0.097 g, 0.67 mmol) and carried on through the general procedure to yield an orange solid (0.033 g, 11%). $^1$H NMR (400 MHz, CDCl$_3$) δ 8.58 (s, 1H), 7.65 (d, J=8.8 Hz, 2H), 7.42 (d, J=7.6 Hz, 1H), 7.31-7.27 (mult, 2H), 7.11 (t, J=7.2 Hz, 1H), 7.20 (t, J=7.6 Hz, 1H), 6.93 (s, 1H), 5.52 (s, 1H), 4.02-3.97 (mult, 1H), 3.88 (s, 3H), 3.02-2.87 (mult, 3H), 2.35 (s, 3H).

(Z)-Methyl 4-(furan-2-yl)-2-hydroxy-4-oxobut-2-enoate (1616-27a). Compound 1616-27a was prepared via Procedure H from 1-(furan-2-yl)ethanone (1.0 g, 9.1 mmol) in MeOH (4.1 mL, 2.2 M) to yield a yellow solid (1.1 g, 61%).

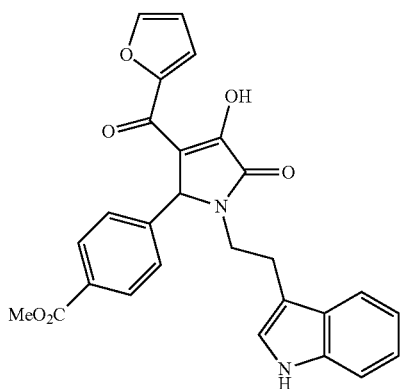 [SMILES: COC(=O)c1ccc(C2C(C(=O)c3ccco3)=C(O)C(=O)N2CCc2c[nH]c3ccccc23)cc1]

Methyl 4-(1-(2-(1H-indol-3-yl)ethyl)-3-(furan-2-carbonyl)-4-hydroxy-5-oxo-2,5-dihydro-1H-pyrrol-2-yl)benzoate (1616-27). Compound 1616-27 was prepared via the general procedure A from methyl 4-formylbenzoate (0.42 g, 2.6 mmol), tryptamine (0.41 g, 2.6 mmol) and (Z)-Methyl 4-(furan-2-yl)-2-hydroxy-4-oxobut-2-enoate (0.50 g, 2.6 mmol) to yield an orange solid (0.079 g, 7%). $^1$H NMR (600 MHz, CDCl$_3$) δ 8.32 (s, 1H), 8.05 (s, 1H), 7.88 (d, J=8.4 Hz, 2H), 7.43-7.41 (mult, 2H), 7.32 (d, J=8.4 Hz, 1H), 7.25 (d, J=8.4 Hz, 2H), 7.16 (t, J=7.2 Hz, 1H), 7.06 (t, J=7.2 Hz, 1H), 6.94 (s, 1H), 6.39 (dd, J=1.8 Hz, J=3.6 Hz, 1H), 5.39 (s, 1H), 4.04-3.99 (mult, 1H), 3.88 (s, 3H), 3.07-2.96 (mult, 2H), 2.93-2.89 (mult, 1H).

(Z)-ethyl 2-hydroxy-4-oxo-4-(pyridin-3-yl)but-2-enoate (1616-28a). Compound 1616-28a was prepared via Procedure H from 1-(pyridin-3-yl)ethanone (9.0 ml, 83 mmol) to yield a pale yellow solid (7.3 g, 40%).

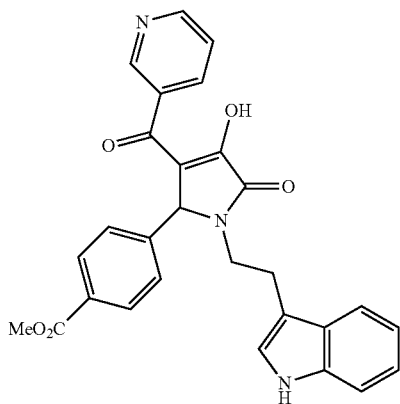 [SMILES: COC(=O)c1ccc(C2C(C(=O)c3cccnc3)=C(O)C(=O)N2CCc2c[nH]c3ccccc23)cc1]

Methyl 4-(1-(2-(1H-indol-3-yl)ethyl)-4-hydroxy-3-nicotinoyl-5-oxo-2,5-dihydro-1H-pyrrol-2-yl)benzoate (1616-28). Compound 1616-28 was prepared via the general procedure A from methyl 4-formylbenzoate (0.079 g, 0.48 mmol), tryptamine (0.077 g, 0.45 mmol) and (Z)-ethyl 2-hydroxy-4-oxo-4-(pyridin-3-yl)but-2-enoate (0.10 g, 0.48 mmol) to yield a yellow solid (0.11 g, 49%). $^1$H NMR (400 MHz, DMSO-d$^6$) δ 10.89 (s, 1H), 8.80 (s, 1H), 8.69 (d, J=4.4 Hz, 1H), 8.00 (d, J=7.6 Hz, 1H), 7.88 (d, J=7.2 Hz, 2H), 7.43-7.42 (mult, 2H), 7.34-7.29 (mult, 2H), 7.14 (d, J=8.0 Hz, 2H), 7.06 (t, J=6.8 Hz, 1H), 6.92 (t, J=7.2 Hz, 1H), 5.42 (s, 1H), 3.87-3.82 (mult, 4H), 3.02-2.89 (mult, 2H), 2.79-2.74 (mult, 1H).

(Z)-ethyl 2-hydroxy-4-oxohex-2-enoate (1616-29a). Compound 1616-29a was prepared via Procedure H from butan-2-one (1.2 ml, 14 mmol) to yield a yellow oil (0.58 g, 24%).

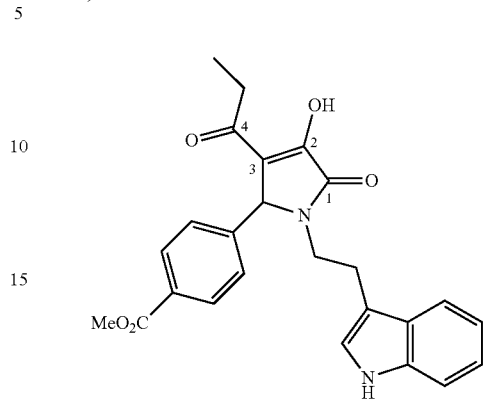

Methyl 4-(1-(2-(1H-indol-3-yl)ethyl)-4-hydroxy-5-oxo-3-propionyl-2,5-dihydro-1H-pyrrol-2-yl)benzoate (1616-29). Compound 1616-29 was prepared via the general procedure A from methyl 4-formylbenzoate (0.095 g, 0.58 mmol), tryptamine (0.93 g, 0.58 mmol) and (Z)-ethyl 2-hydroxy-4-oxohex-2-enoate (0.10 g, 0.58 mmol) to yield a cream colored solid (0.16 g, 64%). $^1$H NMR (400 MHz, DMSO-d$^6$) δ 10.84 (s, 1H), 7.87 (d, J=8.4 Hz, 2H), 7.33-7.23 (mult, 4H), 7.09 (d, J=2.4 Hz, 1H), 7.05 (t, J=8.0 Hz, 1H), 6.91 (t, J=6.8 Hz, 1H), 5.17 (s, 1H), 3.83-3.76 (mult, 4H), 2.96-2.89 (mult, 1H), 2.86-2.79 (mult, 1H), 2.75-2.57 (mult, 3H), 0.85 (t, J=7.6 Hz, 3H).

(Z)-ethyl 2-hydroxy-4-oxo-4-(pyridin-2-yl)but-2-enoate (1616-30a). Compound 1616-30a was prepared via Procedure H from 1-(pyridin-2-yl)ethanone to yield a dark red solid (0.61 g, 33%).

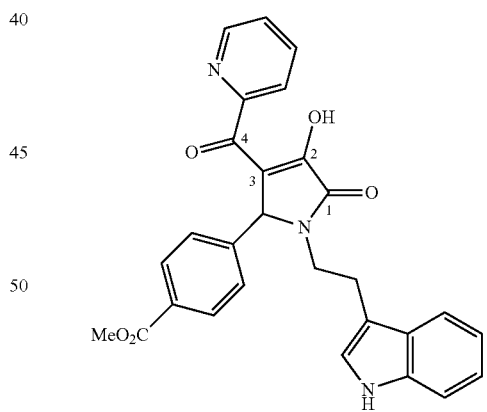

Methyl 4-(1-(2-(1H-indol-3-yl)ethyl)-4-hydroxy-5-oxo-3-picolinoyl-2,5-dihydro-1H-pyrrol-2-yl)benzoate (1616-30). Compound 1616-30 was prepared via the general procedure from methyl 4-formylbenzoate (0.074 g, 0.45 mmol), tryptamine (0.072 g, 0.45 mmol) and (Z)-ethyl 2-hydroxy-4-oxo-4-(pyridin-2-yl)but-2-enoate (0.10 g, 0.45 mmol) to yield a yellow residue (0.037 g, 17%). $^1$H NMR (600 MHz, CDCl$_3$) δ 8.66 (d, J=4.2 Hz, 1H), 8.21 (s, 1H), 8.14 (d, J=7.8 Hz, 1H), 8.07 (dt, J=1.2 Hz, J=7.8 Hz, 1H), 7.94 (d, J=8.4 Hz, 2H), 7.71 (dt, J=0.6 Hz, J=6.0 Hz, 1H), 7.39 (d, J=7.2 Hz, 1H), 7.36 (d, J=7.8 Hz, 1H), 7.21-7.17 (mult, 3H), 7.07

(t, J=8.4 Hz, 1H), 7.01 (d, J=1.8 Hz, 1H), 5.14 (s, 1H), 4.15-4.10 (mult, 1H), 3.89 (s, 3H), 3.11-2.95 (mult, 3H).

(Z)-ethyl 2-hydroxy-4-(5-methylfuran-2-yl)-4-oxobut-2-enoate (1616-31a). Compound 1616-31a was prepared via Procedure H from 1-(5-methylfuran-2-yl)ethanone (1.0 g, 8.1 mmol) to yield a black solid (0.53 g, 29%).

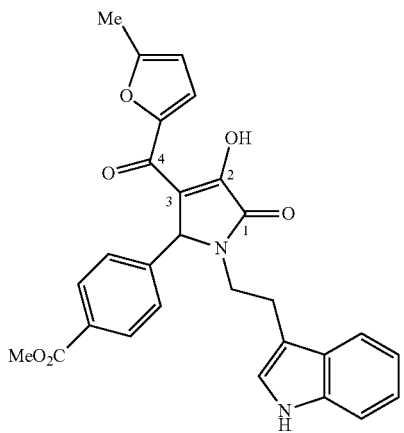 [SMILES: COC(=O)c1ccc(C2C(C(=O)c3ccc(C)o3)=C(O)C(=O)N2CCc2c[nH]c3ccccc23)cc1]

Methyl 4-(1-(2-(1H-indol-3-yl)ethyl)-4-hydroxy-3-(5-methylfuran-2-carbonyl)-5-oxo-2,5-dihydro-1H-pyrrol-2-yl)benzoate (1616-31). Compound 1616-31 was prepared via the general procedure A from methyl 4-formylbenzoate (0.073 g, 0.45 mmol), tryptamine (0.071 g, 0.45 mmol) and (Z)-ethyl 2-hydroxy-4-(5-methylfuran-2-yl)-4-oxobut-2-enoate (0.10 g, 0.45 mmol) to yield a yellow solid (0.081 g, 38%). $^1$H NMR (400 MHz, CDCl$_3$) δ 8.12 (s, 1H), 7.88 (d, J=8.0 Hz, 2H), 7.50 (d, J=8.0 Hz, 1H), 7.40 (d, J=8.4 Hz, 1H), 7.24 (t, J=7.6 Hz, 1H), 7.16 (t, J=7.6 Hz, 1H), 7.12 (d, J=3.2 Hz, 1H), 7.02 (s, 1H), 6.99 (d, J=8.4 Hz, 2H), 6.06 (d, J=3.2 Hz, 1H), 5.14 (s, 1H), 4.07-4.01 (mult, 1H), 3.89 (s, 3H), 3.17-3.10 (mult, 1H), 3.07-2.93 (mult, 2H), 2.15 (s, 3H).

(Z)-ethyl 2-hydroxy-5-methyl-4-oxohex-2-enoate (1616-32a). Compound 1616-32a was prepared via Procedure H from 3-methylbutan-2-one (1.0 g, 12 mmol) to yield a black oil (1.8 g, 83%).

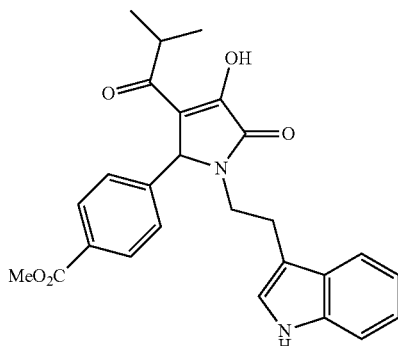

Methyl 4-(1-(2-(1H-indol-3-yl)ethyl)-4-hydroxy-3-isobutyryl-5-oxo-2,5-dihydro-1H-pyrrol-2-yl)benzoate (1616-32). Compound 1616-32 was prepared via the general procedure A from methyl 4-formylbenzoate (0.088 g, 0.54 mmol), tryptamine (0.086 g, 0.54 mmol) and (Z)-ethyl 2-hydroxy-5-methyl-4-oxohex-2-enoate (0.10 g, 0.54 mmol) to yield a light brown residue (0.067 g, 28%). $^1$H NMR (600 MHz, DMSO-d$^6$, 70° C.) δ 10.65 (s, 1H), 7.84 (d, J=7.8 Hz, 2H), 7.32 (d, J=7.8 Hz, 2H), 7.28 (d, J=7.8 Hz, 2H), 7.06-7.03 (mult, 2H), 6.92 (t, J=8.4 Hz, 1H), 5.18 (s, 1H), 3.83 (s, 3H), 3.79-3.75 (mult, 1H), 3.40-3.20 (mult, 2H), 2.98-2.93 (mult, 1H), 2.91-2.86 (mult, 1H), 2.72-2.67 (mult, 1H), 0.86 (d, J=4.8 Hz, 6H).

(Z)-ethyl 2-hydroxy-5,5-dimethyl-4-oxohex-2-enoate (1616-33a). Compound 1616-33a was prepared via Procedure J from 3,3-dimethylbutan-2-one (1.0 g, 10 mmol) to yield a yellow oil (0.62 g, 31%).

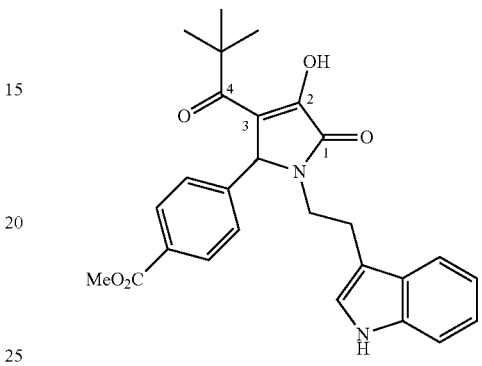

Methyl 4-(1-(2-(1H-indol-3-yl)ethyl)-4-hydroxy-5-oxo-3-pivaloyl-2,5-dihydro-1H-pyrrol-2-yl)benzoate (1616-33). Compound 1616-33 was prepared via the general procedure from methyl 4-formylbenzoate (0.082 g, 0.50 mmol), tryptamine (0.080 g, 0.50 mmol) and (Z)-ethyl 2-hydroxy-5,5-dimethyl-4-oxohex-2-enoate (0.10 g, 0.50 mmol) to yield an orange oil (0.092 g, 40%). $^1$H NMR (600 MHz, CDCl$_3$) δ 8.17 (br s, 1H), 7.93 (d, J=7.8 Hz, 2H), 7.40-7.35 (mult, 2H), 7.20 (t, J=7.2 Hz, 1H), 7.09 (t, J=7.2 Hz, 1H), 7.04 (dd, J=1.2 Hz, J=7.8 Hz, 2H), 6.96 (s, 1H), 5.04 (s, 1H), 4.02-3.99 (mult, 1H), 3.91 (s, 3H), 3.09-3.00 (mult, 2H), 2.95-2.91 (mult, 1H), 1.06 (s, 9H).

Methyl 4-(1-(2-(1H-indol-3-yl)ethyl)-4-hydroxy-5-oxo-3-pivaloyl-2,5-dihydro-1H-pyrrol-2-yl)benzoate (1616-33). Compound 1616-33 was prepared via Procedure A from methyl 4-formylbenzoate (0.082 g, 0.50 mmol), tryptamine (0.080 g, 0.50 mmol) and 1616-33a (0.10 g, 0.50 mmol) to yield an orange oil (0.092 g, 40%).

(Z)-ethyl 2-hydroxy-4-(3-methoxyphenyl)-4-oxobut-2-enoate (1616-34a). Compound 1616-34a was prepared via Procedure H from 1-(3-methoxyphenyl)ethanone (1.0 g, 6.7 mmol) to yield a brown-yellow oil (0.96 g, 58%).

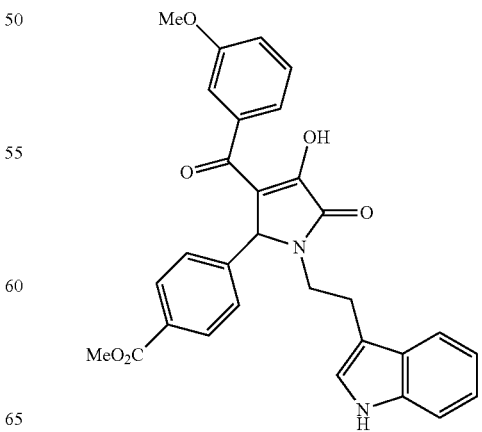

Methyl 4-(1-(2-(1H-indol-3-yl)ethyl)-4-hydroxy-3-(3-methoxybenzoyl)-5-oxo-2,5-dihydro-1H-pyrrol-2-yl)benzoate (1616-34). Compound 1616-34 was prepared via the general procedure from methyl 4-formylbenzoate (0.066 g, 0.40 mmol), tryptamine (0.064 g, 0.40 mmol) (Z)-ethyl 2-hydroxy-4-(3-methoxyphenyl)-4-oxobut-2-enoate (0.10 g, 0.40 mmol) to yield a pale yellow residue (0.046 g, 23%). $^1$H NMR (600 MHz, DMSO-d$^6$, 80° C.) δ 10.64 (s, 1H), 7.89-7.82 (mult, 3H), 7.35-7.22 (mult, 6H), 7.07-7.05 (mult, 2H), 6.98-6.91 (mult, 2H), 5.34 (s, 1H), 4.26 (mult, 1H), 3.82 (s, 3H), 3.74 (s, 3H), 3.01-2.90 (mult, 2H), 2.78-2.75 (mult, 1H).

(Z)-ethyl 4-(3-fluorophenyl)-2-hydroxy-4-oxobut-2-enoate (1616-35a). Compound 1616-35a was prepared via Procedure H from 1-(3-fluorophenyl)ethanone (1.0 g, 7.2 mmol) to yield a light brown solid (1.1 g, 61%).

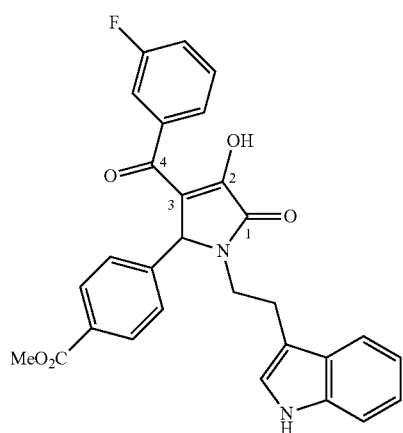 [SMILES: COC(=O)c1ccc(C2C(C(=O)c3cccc(F)c3)=C(O)C(=O)N2CCc2c[nH]c3ccccc23)cc1]

Methyl 4-(1-(2-(1H-indol-3-yl)ethyl)-3-(3-fluorobenzoyl)-4-hydroxy-5-oxo-2,5-dihydro-1H-pyrrol-2-yl)benzoate (1616-35). Compound 1616-35 was prepared via the general procedure A from methyl 4-formylbenzoate (0.069 g, 0.42 mmol), tryptamine (0.067 g, 0.42 mmol) and (Z)-ethyl 4-(3-fluorophenyl)-2-hydroxy-4-oxobut-2-enoate (0.10 g, 0.42 mmol) to yield a yellow residue (0.028 g, 14%). $^1$H NMR (600 MHz, DMSO-d$^6$, 80° C.) δ 10.66 (s, 1H), 7.79 (d, J=8.4 Hz, 2H), 7.53-7.45 (mult, 2H), 7.34 (dd, J=3.0 Hz, J=8.4 Hz, 2H), 7.29-7.26 (mult, 1H), 7.22 (d, J=7.8 Hz, 2H), 7.13-7.10 (mult, 1H), 7.07-7.04 (mult, 2H), 6.93 (t, J=7.8 Hz, 1H), 5.32 (s, 1H), 3.84-3.79 (mult, 4H), 3.01-2.96 (mult, 1H), 2.92-2.88 (mult, 1H), 2.76-2.71 (mult, 1H).

(Z)-ethyl 4-(3-chlorophenyl)-2-hydroxy-4-oxobut-2-enoate (1616-36a). Compound 1616-36a was prepared via Procedure J from 1-(3-chlorophenyl)ethanone (1.0 g, 6.5 mmol) to yield a brown-green solid (1.1 g, 65%).

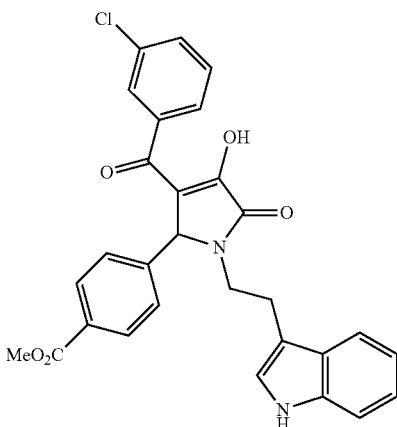

Methyl 4-(1-(2-(1H-indol-3-yl)ethyl)-3-(3-chlorobenzoyl)-4-hydroxy-5-oxo-2,5-dihydro-1H-pyrrol-2-yl)benzoate (1616-36). Compound 1616-36 was prepared via the general procedure A from methyl 4-formylbenzoate (0.064 g, 0.39 mmol), tryptamine (0.063 g, 0.39 mmol) and (Z)-ethyl 4-(3-chlorophenyl)-2-hydroxy-4-oxobut-2-enoate (0.10 g, 0.39 mmol) to yield a pale yellow residue (0.045 g, 22%). $^1$H NMR (600 MHz, DMSO-d$^6$, 80° C.) δ 10.69 (s, 1H), 7.82 (d, J=8.4 Hz, 2H), 7.69 (s, 1H), 7.58 (d, J=6.0 Hz, 1H), 7.35-7.32 (mult, 3H), 7.29-7.26 (mult, 3H), 7.07-7.05 (mult, 2H), 6.93 (t, J=7.2 Hz, 1H), 5.28 (s, 1H), 3.82-3.79 (mult, 4H), 2.98-2.94 (mult, 1H), 2.88-2.84 (mult, 1H), 2.74-2.68 (mult, 1H).

(Z)-ethyl 2-hydroxy-4-oxo-4-(thiophen-2-yl)but-2-enoate (1616-37a). Compound 1616-37a was prepared via Procedure H from 1-(thiophen-2-yl)ethanone (0.89 mL, 7.9 mmol) to yield a yellow oil (0.71 g, 40%).

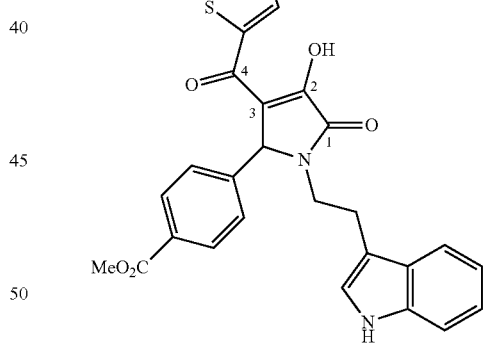

Methyl 4-(1-(2-(1H-indol-3-yl)ethyl)-4-hydroxy-5-oxo-3-(thiophene-2-carbonyl)-2,5-dihydro-1H-pyrrol-2-yl)benzoate (1616-37). Compound 1616-37 was prepared via the general procedure A from methyl 4-formylbenzoate (0.073 g, 0.44 mmol), tryptamine (0.071 g, 0.44 mmol) and (Z)-ethyl 2-hydroxy-4-oxo-4-(thiophen-2-yl)but-2-enoate (0.10 g, 0.44 mmol) to yield a yellow residue (0.043 g, 20%). $^1$H NMR (400 MHz, DMSO-d$^6$) δ 10.80 (s, 1H), 7.83 (d, J=8.4 Hz, 2H), 7.55 (d, J=4.0 Hz, 1H), 7.34-7.29 (mult, 4H), 7.06-7.02 (mult, 3H), 6.92 (t, J=7.2 Hz, 1H), 5.80-5.70 (mult, 1H), 5.28 (s, 1H), 3.86-3.74 (mult, 4H), 3.00-2.89 (mult, 1H), 2.85-2.78 (mult, 1H), 2.73-2.67 (mult, 1H).

(Z)-ethyl 2-hydroxy-4-oxo-4-(m-tolyl)but-2-enoate (1616-38a). Compound 1616-38a was prepared via Procedure H from 1-m-tolylethanone (1.0 mL, 7.5 mmol) to yield a brown-yellow oil (0.26 g, 15%).

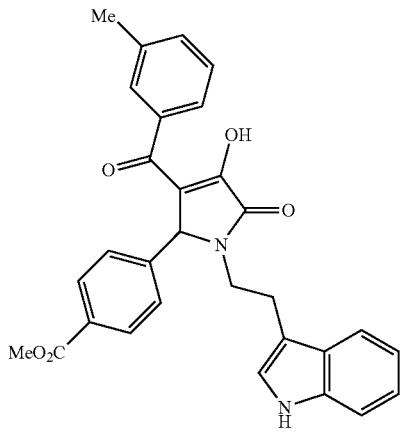 [SMILES: COC(=O)c1ccc(C2C(C(=O)c3cccc(C)c3)=C(O)C(=O)N2CCc2c[nH]c3ccccc23)cc1]

Methyl 4-(1-(2-(1H-indol-3-yl)ethyl)-4-hydroxy-3-(3-methylbenzoyl)-5-oxo-2,5-dihydro-1H-pyrrol-2-yl)benzoate (1616-38). Compound 1616-38 was prepared via the general procedure A from methyl 4-formylbenzoate (0.17 g, 1.0 mmol), tryptamine (0.17 g, 1.0 mmol) and (Z)-ethyl 2-hydroxy-4-oxo-4-(m-tolyl)but-2-enoate (0.24 g, 1.0 mmol) to yield a pale yellow residue (0.029 g, 6%). $^1$H NMR (600 MHz, DMSO-d$^6$, 80° C.) δ 10.67 (s, 1H), 7.72 (mult, 2H), 7.36-7.33 (mult, 2H), 7.28-7.21 (mult, 2H), 7.11-7.04 (mult, 6H), 6.93 (t, J=7.2 Hz, 1H), 5.29 (s, 1H), 3.86-3.78 (mult, 4H), 3.01-2.96 (mult, 1H), 2.91-2.86 (mult, 1H), 2.76-2.72 (mult, 1H), 2.23 (s, 3H).

(Z)-ethyl 2-hydroxy-4-oxo-4-(o-tolyl)but-2-enoate (1616-39a). Compound 1616-39a was prepared via Procedure H from 1-o-tolylethanone (0.98 mL, 7.5 mmol) to yield an orange oil (1.8 g, >99%).

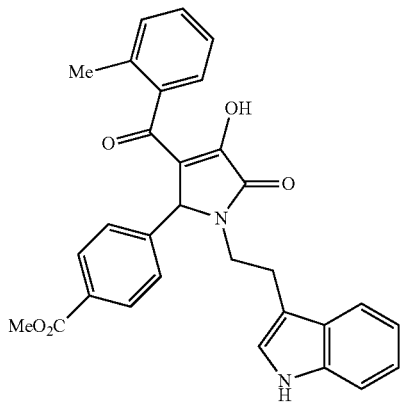 [SMILES: COC(=O)c1ccc(C2C(C(=O)c3ccccc3C)=C(O)C(=O)N2CCc2c[nH]c3ccccc23)cc1]

Methyl 4-(1-(2-(1H-indol-3-yl)ethyl)-4-hydroxy-3-(2-methylbenzoyl)-5-oxo-2,5-dihydro-1H-pyrrol-2-yl)benzoate (1616-39). Compound 1616-39 was prepared via the general procedure A from methyl 4-formylbenzoate (0.14 g, 0.85 mmol), tryptamine (0.14 g, 0.85 mmol) and (Z)-ethyl 2-hydroxy-4-oxo-4-(o-tolyl)but-2-enoate (0.20 g, 0.85 mmol) to yield a pale yellow residue (0.040 g, 9%). $^1$H NMR (600 MHz, DMSO-d$^6$, 70° C.) δ 10.71 (br s, 1H), 7.67 (d, J=7.2 Hz, 2H), 7.37 (d, J=9.0 Hz, 1H), 7.30 (d, J=7.8 Hz, 1H), 7.13-6.99 (mult, 4H), 6.94-6.91 (mult, 2H), 6.84-6.74 (mult, 3H), 4.96 (s, 1H), 3.82-3.76 (mult, 4H), 2.97-2.92 (mult, 1H), 2.82-2.71 (mult, 2H), 1.78 (s, 3H).

(Z)-ethyl 2-hydroxy-4-(2-methoxyphenyl)-4-oxobut-2-enoate (1616-40a). Compound 1616-40a was prepared via Procedure H from 1-(2-methoxyphenyl)ethanone (1.0 g, 6.7 mmol) to yield a yellow solid (0.89 g, 53%).

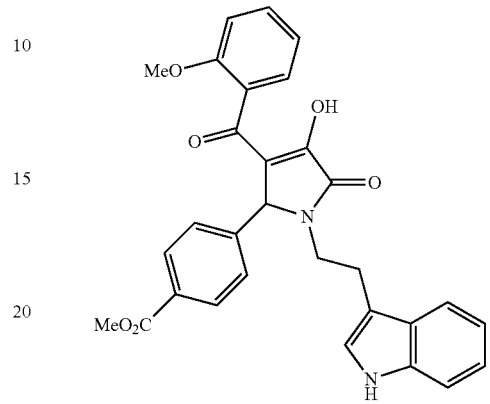

Methyl 4-(1-(2-(1H-indol-3-yl)ethyl)-4-hydroxy-3-(2-methoxybenzoyl)-5-oxo-2,5-dihydro-1H-pyrrol-2-yl)benzoate (1616-40). Compound 1616-40 was prepared via the general procedure A from methyl 4-formylbenzoate (0.13 g, 0.80 mmol), tryptamine (0.13 g, 0.80 mmol) and (Z)-ethyl 2-hydroxy-4-(2-methoxyphenyl)-4-oxobut-2-enoate (0.20 g, 0.80 mmol) to yield a pink residue (0.028 g, 7%). $^1$H NMR (600 MHz, DMSO-d$^6$) δ 10.83 (s, 1H), 7.89 (s, 1H), 7.50 (d, J=6.0 Hz, 1H), 7.34-7.18 (mult, 5H), 7.09-7.04 (mult, 3H), 6.96-6.88 (mult, 3H), 5.27 (s, 1H), 3.83-3.74 (mult, 6H), 2.99-2.87 (mult, 2H), 2.73-2.65 (mult, 2H).

(Z)-ethyl 4-(2-fluorophenyl)-2-hydroxy-4-oxobut-2-enoate (1616-41a). Compound 1616-41a was prepared via Procedure H from 1-(2-fluorophenyl)ethanone (0.88 mL, 6.7 mmol) to yield a yellow solid (0.48 g, 29%).

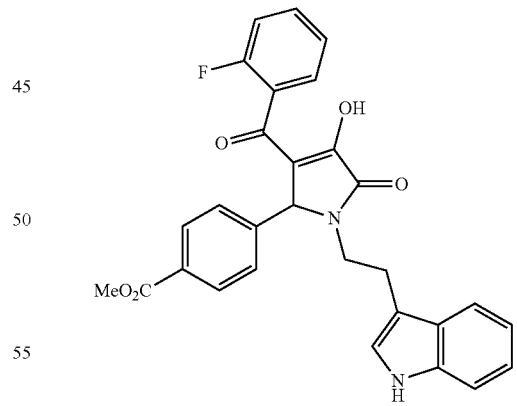

Methyl 4-(1-(2-(1H-indol-3-yl)ethyl)-3-(2-fluorobenzoyl)-4-hydroxy-5-oxo-2,5-dihydro-1H-pyrrol-2-yl)benzoate (1616-41). Compound 1616-41 was prepared via the general procedure A from methyl 4-formylbenzoate (0.19 g, 0.84 mmol), tryptamine (0.14 g, 0.84 mmol) and (Z)-ethyl 4-(2-fluorophenyl)-2-hydroxy-4-oxobut-2-enoate (0.20 g, 0.84 mmol) to yield a brown solid (0.070 g, 17%). $^1$H NMR (600 MHz, DMSO-d$^6$, 70° C.) δ 10.68 (s, 1H), 7.80-7.54 (mult, 2H), 7.35-7.30 (mult, 4H), 7.11-6.78 (mult, 7H), 5.07

(s, 1H), 3.81-3.74 (mult, 4H), 2.97-2.92 (mult, 1H), 2.87-2.82 (mult, 1H), 2.72-2.67 (mult, 1H).

(Z)-ethyl 4-(2-chlorophenyl)-2-hydroxy-4-oxobut-2-enoate (1616-42a). Compound 1616-42a was prepared via Procedure H from 1-(2-chlorophenyl)ethanone (1.0 g, 6.5 mmol) to yield a yellow oil (0.58 g, 35%).

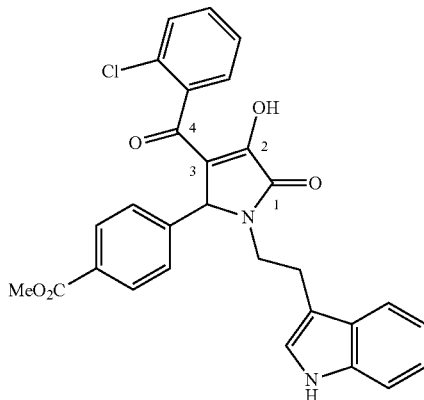 [SMILES: COC(=O)c1ccc(C2C(C(=O)c3ccccc3F)=C(O)C(=O)N2CCc2c[nH]c3ccccc23)cc1]

Methyl 4-(1-(2-(1H-indol-3-yl)ethyl)-3-(2-chlorobenzoyl)-4-hydroxy-5-oxo-2,5-dihydro-1H-pyrrol-2-yl)benzoate (1616-42). Compound 1616-42 was prepared via the general procedure from methyl 4-formylbenzoate (0.13 g, 0.79 mmol), tryptamine (0.13 g, 0.79 mmol) and (Z)-ethyl 4-(2-chlorophenyl)-2-hydroxy-4-oxobut-2-enoate (0.20 g, 0.79 mmol) to yield a cream colored solid (0.27 g, 66%). $^1$H NMR (600 MHz, DMSO-d$^6$, 80° C.) δ 10.64 (s, 1H), 7.67 (mult, 2H), 7.35 (d, J=8.4 Hz, 1H), 7.30 (d, J=7.8 Hz, 1H), 7.24-7.18 (mult, 2H), 7.10-7.03 (mult, 4H), 6.92 (t, J=7.2 Hz, 2H), 6.78 (mult, 1H), 5.04 (s, 1H), 3.86-3.75 (mult, 4H), 2.97-2.92 (mult, 1H), 2.85-2.83 (mult, 1H), 2.73-2.68 (mult, 1H).

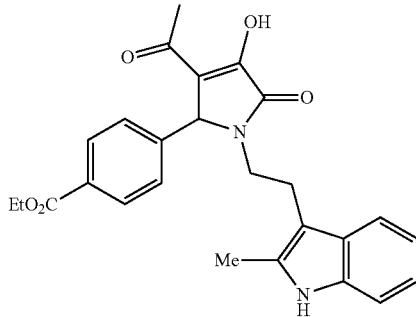 [SMILES: CCOC(=O)c1ccc(C2C(C(C)=O)=C(O)C(=O)N2CCc2c(C)[nH]c3ccccc23)cc1]

Ethyl 4-(3-acetyl-4-hydroxy-1-(2-(2-methyl-1H-indol-3-yl)ethyl)-5-oxo-2,5-dihydro-1H-pyrrol-2-yl)benzoate (1616-43). Compound 1616-43/was prepared via the general procedure from 1616-16a (0.15 g, 0.84 mmol), 2-(2-methyl-1H-indol-3-yl)ethanamine (0.15 g, 0.84 mmol) and methyl acetopyruvate (0.12 g, 0.84 mmol) to yield a cream colored solid (0.078 g, 21%). $^1$H NMR (600 MHz, DMSO-d$^6$, 80° C.) δ 10.5 (br s, 1H), 7.83 (d, J=7.2 Hz, 2H), 7.23-7.18 (mult, 4H), 6.95 (t, J=7.2 Hz, 1H), 6.86 (t, J=7.2 Hz, 1H), 5.09 (s, 1H), 4.30 (q, J=7.2 Hz, 2H), 3.61-3.56 (mult, 1H), 2.92-2.87 (mult, 1H), 2.80-2.75 (mult, 1H), 2.57-2.53 (mult, 1H), 2.19 (s, 3H), 2.05 (s, 3H), 1.30 (t, J=7.2 Hz, 3H).

Ethyl 4-formyl-3-hydroxybenzoate (1616-44a). To a solution of 4-formyl-3-hydroxybenzoic acid (0.43 g, 2.6 mmol) in DMF (0.52 mL, 5.0 M) was added cesium fluoride (0.59 g, 3.9 mmol) and iodoethane (0.23 mL, 2.9 mmol, 1.1 equiv). The reaction mixture stirred at rt for 6 days before being concentrated in vacuo, diluted with water and extracted with DCM (2×). The combined organic layers were dried over MgSO$_4$, filtered and concentrated in vacuo. Purification was achieved via flash column chromatography on SiO$_2$ (Hexanes/EtOAc: 1/1) to afford a white solid (0.19 g, 39%).

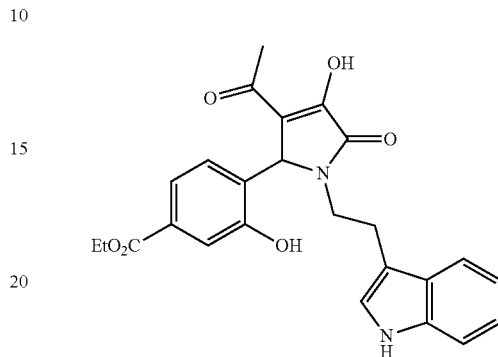

Ethyl 4-(1-(2-(1H-indol-3-yl)ethyl)-3-acetyl-4-hydroxy-5-oxo-2,5-dihydro-1H-pyrrol-2-yl)-3-hydroxybenzoate (1616-44). Compound 1616-44 was prepared via the general procedure A from ethyl 4-formyl-3-hydroxybenzoate (0.15 g, 0.77 mmol), tryptamine (0.12 g, 0.77 mmol) and methyl acetopyruvate (0.11 g, 0.77 mmol) to yield a cream colored solid (0.20 g, 57%). $^1$H NMR (400 MHz, DMSO-d$^6$) δ 10.81 (s, 1H), 10.42 (s, 1H), 7.59-7.46 (mult, 1H), 7.34-7.23 (mult, 3H), 7.12-7.02 (mult, 2H), 6.97-6.89 (mult, 2H), 5.76 (s, 1H), 4.28 (q, J=7.2 Hz, 2H), 3.78-3.74 (mult, 1H), 2.98-2.85 (mult, 2H), 2.73-2.68 (mult, 1H), 2.28 (s, 3H), 1.29 (t, J=7.2 Hz, 3H).

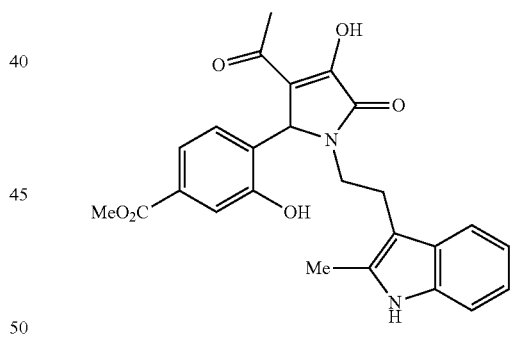

Methyl 4-(3-acetyl-4-hydroxy-1-(2-(2-methyl-1H-indol-3-yl)ethyl)-5-oxo-2,5-dihydro-1H-pyrrol-2-yl)-3-hydroxybenzoate (1616-45). Compound 1616-45 was prepared via the general procedure A from 1616-12b (0.19 g, 1.0 mmol), 2-(2-methyl-1H-indol-3-yl)ethanamine (0.18 g, 1.0 mmol) and methyl acetopyruvate (0.15 g, 1.0 mmol) to yield a red solid (0.085 g, 18%). $^1$H NMR (600 MHz, DMSO-d$^6$, 80° C.) δ 10.62 (br s, 1H), 7.49 (d, J=7.8 Hz, 1H), 7.37 (d, J=6.6 Hz, 1H), 7.18 (d, J=7.2 Hz, 2H), 6.93 (t, J=6.6 Hz, 1H), 6.85-6.82 (mult, 2H), 5.73 (s, 1H), 3.82 (s, 3H), 3.73-3.67 (mult, 1H), 2.89-2.85 (mult, 1H), 2.75-2.69 (mult, 1H), 2.65-58 (mult, 1H), 2.20 (s, 3H), 2.06 (s, 3H).

(Z)-ethyl 2-hydroxy-4-oxo-4-phenylbut-2-enoate (1616-46a). Compound 1616-46a was prepared via Procedure H from acetophenone (1.0 g, 8.3 mmol) to yield an orange oil (0.80 g, 44%).

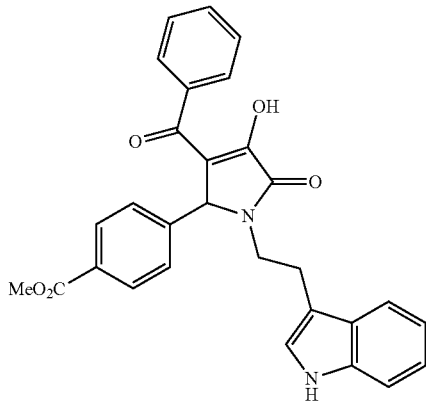 [SMILES: COC(=O)c1ccc(C2C(C(=O)c3ccccc3)=C(O)C(=O)N2CCc2c[nH]c3ccccc23)cc1]

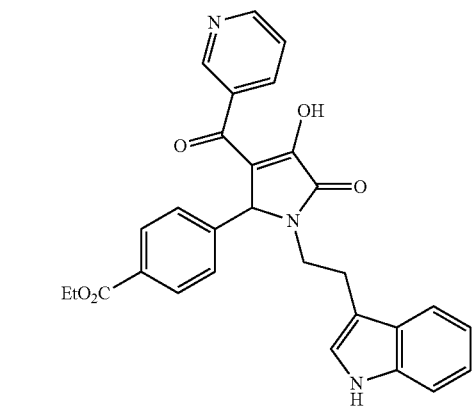

Methyl 4-(1-(2-(1H-indol-3-yl)ethyl)-3-benzoyl-4-hydroxy-5-oxo-2,5-dihydro-1H-pyrrol-2-yl)benzoate (1616-46). Compound 1616-46 was prepared via the general procedure A from (Z)-ethyl 2-hydroxy-4-oxo-4-phenylbut-2-enoate (0.15 g, 0.68 mmol), tryptamine (0.11 g, 0.68 mmol) and methyl 4-formylbenzoate (0.11 g, 0.68 mmol) to yield a cream colored solid (0.031 g, 9%). $^1$H NMR (400 MHz, DMSO-d$^6$) δ 10.83 (s, 1H), 7.79 (d, J=7.2 Hz, 2H), 7.59-7.48 (mult, 2H), 7.40-7.28 (mult, 3H), 7.24-7.21 (mult, 3H), 7.11-7.04 (mult, 2H), 6.92 (t, J=7.6 Hz, 1H), 6.74 (s, 1H), 5.25 (s, 1H), 3.80-3.74 (mult, 4H), 3.00-2.90 (mult, 1H), 2.82-2.67 (mult, 2H).

Ethyl 4-(1-(2-(1H-indol-3-yl)ethyl)-4-hydroxy-3-nicotinoyl-5-oxo-2,5-dihydro-1H-pyrrol-2-yl)benzoate (1616-48). Compound 1616-48 was prepared via the general procedure A from 1616-28a (0.15 g, 0.68 mmol), tryptamine (0.11 g, 0.68 mmol) and 1616-16a (0.12 g, 0.68 mmol) to yield a yellow solid (0.027 g, 8%). $^1$H NMR (400 MHz, DMSO-d$^6$) δ 10.84 (s, 1H), 8.75 (s, 1H), 8.48 (d, J=3.2 Hz, 1H), 7.94 (d, J=7.2 Hz, 1H), 7.83 (d, J=8.0 Hz, 2H), 7.34-7.27 (mult, 5H), 7.08-7.04 (mult, 2H), 6.92 (t, J=7.2 Hz, 1H), 5.33 (s, 1H), 4.28 (q, J=7.6 Hz, 2H), 3.84-3.77 (mult, 1H), 3.00-2.93 (mult, 1H), 2.87-2.80 (mult, 1H), 2.73-2.66 (mult, 1H), 1.28 (t, J=6.8 Hz, 3H).

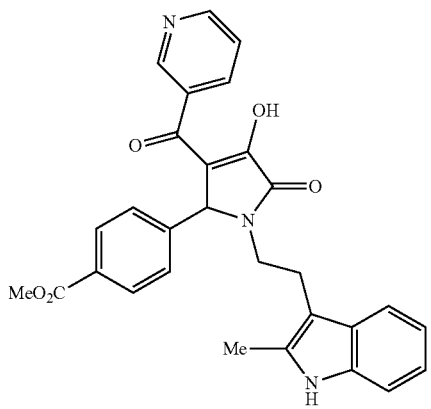 [SMILES: COC(=O)c1ccc(C2C(C(=O)c3cccnc3)=C(O)C(=O)N2CCc2c(C)[nH]c3ccccc23)cc1]

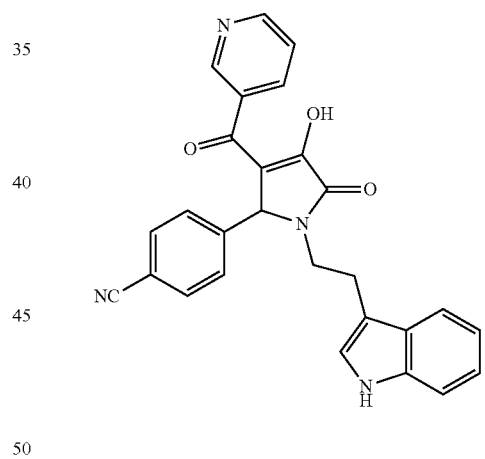

Methyl 4-(4-hydroxy-1-(2-(2-methyl-1H-indol-3-yl)ethyl)-3-nicotinoyl-5-oxo-2,5-dihydro-1H-pyrrol-2-yl)benzoate (1616-47). Compound 1616-47 was prepared via the general procedure from 1616-28a (0.15 g, 0.68 mmol), 2-(2-methyl-1H-indol-3-yl)ethanamine (0.12 g, 0.68 mmol) and methyl 4-formylbenzoate (0.11 g, 0.68 mmol) to yield an orange solid (0.046 g, 14%). $^1$H NMR (400 MHz, DMSO-d$^6$) δ 10.75 (s, 1H), 8.73 (s, 1H), 8.48 (d, J=4.4 Hz, 1H), 7.93 (s, 1H), 7.82 (d, J=8.4 Hz, 2H), 7.30-7.17 (mult, 5H), 6.97 (t, J=6.4 Hz, 1H), 6.86 (t, J=7.2 Hz, 1H), 5.23 (s, 1H), 3.81 (s, 3H), 3.63-3.56 (mult, 1H), 2.96-2.88 (mult, 1H), 2.76-2.69 (mult, 1H), 2.57-2.50 (mult, 1H), 2.18 (s, 3H).

4-(1-(2-(1H-Indol-3-yl)ethyl)-4-hydroxy-3-nicotinoyl-5-oxo-2,5-dihydro-1H-pyrrol-2-yl)benzonitrile (1616-49). Compound 1616-49 was prepared via the general procedure A from 4-formylbenzonitrile (0.15 g, 1.1 mmol), tryptamine (0.18 g, 1.1 mmol) and 1616-28a (0.25 g, 1.1 mmol) to yield a yellow solid (0.084 g, 17%). $^1$H NMR (600 MHz, DMSO-d$^6$) δ 10.84 (s, 1H), 8.81 (s, 1H), 8.69 (d, J=3.6 Hz, 1H), 8.01 (d, J=7.8 Hz, 1H), 7.75 (d, J=7.8 Hz, 2H), 7.50-7.47 (mult, 3H), 7.33 (d, J=8.4 Hz, 1H), 7.31 (d, J=7.8 Hz, 1H), 7.13 (s, 1H), 7.07 (t, J=7.8 Hz, 1H), 6.94 (t, J=7.2 Hz, 1H), 5.44 (s, 1H), 3.88-3.83 (mult, 1H), 3.01-2.90 (mult, 2H), 2.79-2.75 (mult, 1H).

(Z)-ethyl 2-hydroxy-4-oxo-4-(pyridin-4-yl)but-2-enoate (1616-50a). Compound 1616-50a was prepared via Procedure H from 1-(pyridine-4-yl)ethanone (0.55 mL, 8.3 mmol) to yield an orange solid (0.29 g, 16%).

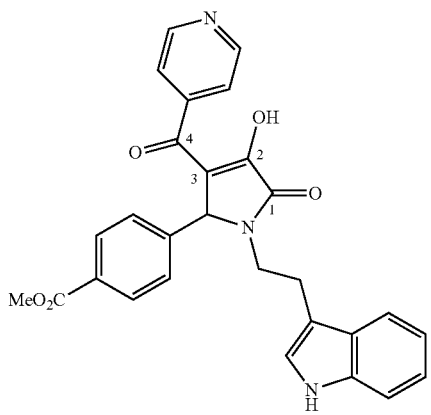 [SMILES: COC(=O)c1ccc(C2C(C(=O)c3ccncc3)=C(O)C(=O)N2CCc2c[nH]c3ccccc23)cc1]

Methyl 4-(1-(2-(1H-indol-3-yl)ethyl)-4-hydroxy-3-isonicotinoyl-5-oxo-2,5-dihydro-1H-pyrrol-2-yl)benzoate (1616-50). Compound 1616-50 was prepared via the general procedure A from methyl 4-formylbenzoate (0.15 g, 0.9 mmol), tryptamine (0.15 g, 0.9 mmol) and (Z)-ethyl 2-hydroxy-4-oxo-4-(pyridin-4-yl)but-2-enoate (0.20 g, 0.9 mmol) to yield a yellow solid (0.13 g, 30%). $^1$H NMR (600 MHz, DMSO-d$^6$, 80° C.) δ 10.63 (s, 1H), 8.47 (d, J=2.8 Hz, 1H), 7.76-6.92 (mult, 12H), 5.27 (s, 1H), 3.82-3.78 (mult, 4H), 3.00-2.95 (mult, 1H), 2.91-2.86 (mult, 1H), 2.74-2.72 (mult, 1H).

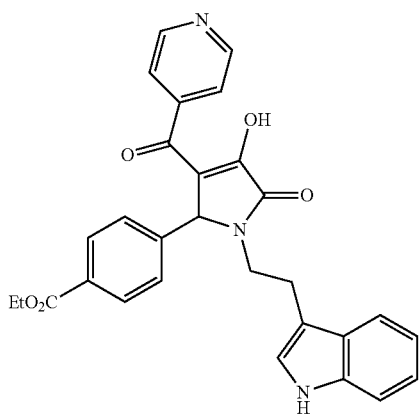 [SMILES: CCOC(=O)c1ccc(C2C(C(=O)c3ccncc3)=C(O)C(=O)N2CCc2c[nH]c3ccccc23)cc1]

Ethyl 4-(1-(2-(1H-indol-3-yl)ethyl)-4-hydroxy-3-isonicotinoyl-5-oxo-2,5-dihydro-1H-pyrrol-2-yl)benzoate (1616-51). Compound 1616-51 was prepared via the general procedure A from 1616-16a (0.40 g, 2.3 mmol), tryptamine (0.36 g, 2.3 mmol) and 1616-50a (0.50 g, 2.3 mmol) to yield a yellow solid (0.019 g, 2%). $^1$H NMR (600 MHz, DMSO-d$^6$) δ 10.84 (s, 1H), 8.68 (d, J=5.4 Hz, 2H), 7.88 (d, J=8.4 Hz, 2H), 7.51 (d, J=5.4 Hz, 2H), 7.40 (d, J=8.4 Hz, 2H), 7.34 (d, J=8.4 Hz, 1H), 7.30 (d, J=8.4 Hz, 1H), 7.12 (d, J=1.8 Hz, 1H), 7.06 (t, J=7.8 Hz, 1H), 6.92 (t, J=7.2 Hz, 1H), 5.40 (s, 1H), 4.29 (q, J=7.2 Hz, 2H), 3.88-3.82 (mult, 1H), 3.00-2.90 (mult, 2H), 2.78-2.73 (mult, 1H), 1.29 (7.2 Hz, 3H).

4-Formyl-N-methylbenzamide (1616-52a). Compound 1616-52a was prepared via Procedure I from methanamine (3.3 mL, 2.0 M in MeOH, 6.7 mmol) to yield a white solid (0.14 g, 13%).

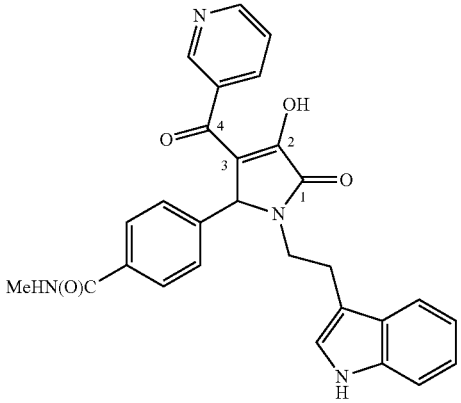

4-(1-(2-(1H-Indol-3-yl)ethyl)-4-hydroxy-3-nicotinoyl-5-oxo-2,5-dihydro-1H-pyrrol-2-yl)-N-methylbenzamide (1616-52). Compound 1616-52 was prepared via the general procedure A from 1616-52a (0.15 g, 0.93 mmol), tryptamine (0.15 g, 0.93 mmol) and 4-formyl-N-methylbenzamide (0.21 g, 0.93 mmol) to yield a yellow solid (0.33 g, 73%). $^1$H NMR (600 MHz, DMSO-d$^6$) δ 10.72 (s, 1H), 8.79 (s, 1H), 8.67 (d, J=4.8 Hz, 1H), 8.24 (d, J=3.6 Hz, 1H), 7.99 (d, J=7.8 Hz, 1H), 7.75 (d, J=7.8 Hz, 2H), 7.45 (t, J=5.4 Hz, 1H), 7.39-7.34 (mult, 4H), 7.11-7.05 (mult, 2H), 6.94 (t, J=7.2 Hz, 1H), 5.38 (s, 1H), 3.88-3.84 (mult, 1H), 3.11-3.09 (mult, 1H), 3.02-2.94 (mult, 2H), 2.76 (d, J=4.8 Hz, 3H).

4-Formyl-N,N-dimethylbenzamide (1616-53a). Compound 1616-53a was prepared via Procedure I from dimethylamine (6.7 mL, 2.0 M in THF, 13 mmol) to yield an opaque oil (1.2 g, 51%).

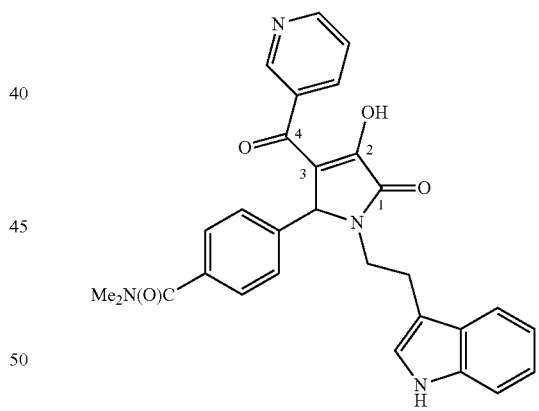

4-(1-(2-(1H-Indol-3-yl)ethyl)-4-hydroxy-3-nicotinoyl-5-oxo-2,5-dihydro-1H-pyrrol-2-yl)-N,N-dimethylbenzamide (1616-53). Compound 1616-52 was prepared via the general procedure from 1616-52a (0.38 g, 1.7 mmol), tryptamine (0.27 g, 1.7 mmol) and 4-formyl-N,N-dimethylbenzamide (0.30 g, 1.7 mmol) to yield a yellow solid (0.33 g, 39%). $^1$H NMR (600 MHz, DMSO-d$^6$) δ 10.85 (s, 1H), 8.81 (s, 1H), 8.69 (d, J=4.8 Hz, 1H), 8.01 (d, J=7.8 Hz, 1H), 7.49-7.47 (mult, 2H), 7.36-7.29 (mult, 4H), 7.14-7.10 (mult, 2H), 7.06 (t, J=7.8 Hz, 1H), 6.92 (t, J=7.2 Hz, 1H), 5.42 (s, 1H), 3.88-3.82 (mult, 1H), 3.02-2.95 (mult, 5H), 2.84 (s, 3H), 2.77-2.71 (mult, 1H).

(Z)-ethyl 2-hydroxy-4-oxo-4-(thiophen-3-yl)but-2-enoate (1616-54a). Compound 1616-54a was prepared via Procedure H from 1-(thiophen-3-yl)ethanone (1.0 g, 7.9 mmol) to yield a cream colored solid (1.2 g, 68%).

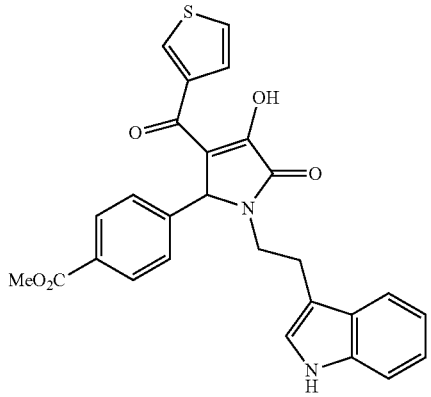 [SMILES: COC(=O)c1ccc(C2C(C(=O)c3ccsc3)=C(O)C(=O)N2CCc2c[nH]c3ccccc23)cc1]

Methyl 4-(1-(2-(1H-indol-3-yl)ethyl)-4-hydroxy-5-oxo-3-(thiophene-3-carbonyl)-2,5-dihydro-1H-pyrrol-2-yl)benzoate (1616-54). Compound 1616-54 was prepared via the general procedure A from methyl 4-formylbenzoate (0.36 g, 2.2 mmol), tryptamine (0.35 g, 2.2 mmol) and (Z)-ethyl 2-hydroxy-4-oxo-4-(thiophen-3-yl)but-2-enoate (0.50 g, 2.2 mmol) to yield a cream colored solid (0.70 g, 65%). $^1$H NMR (400 MHz, DMSO-d$^6$) δ 10.86 (s, 1H), 8.38 (d, J=2.8 Hz, 1H), 7.85 (d, J=7.6 Hz, 2H), 7.49 (t, J=4.0 Hz, 1H), 7.37-7.31 (mult, 4H), 7.13 (s, 1H), 7.07 (t, J=7.6 Hz, 1H), 6.93 (t, J=6.8 Hz, 1H), 5.76 (d, J=1.2 Hz, 1H), 5.44 (s, 1H), 3.89-3.81 (mult, 4H), 3.02-2.90 (mult, 2H), 2.80-2.74 (mult, 1H).

50a (0.38 g, 1.7 mmol) to yield an orange solid (0.78 g, 98%). $^1$H NMR (400 MHz, DMSO-d$^6$) δ 11.08 (s, 1H), 8.66 (d, J=5.6 Hz, 2H), 7.92 (d, J=8.0 Hz, 2H), 7.51-7.37 (mult, 6H), 7.13-7.08 (mult, 2H), 6.97 (t, J=7.2 Hz, 1H), 5.11-5.07 (mult, 2H), 3.84 (s, 3H), 3.80 (d, J=14.8 Hz, 1H).

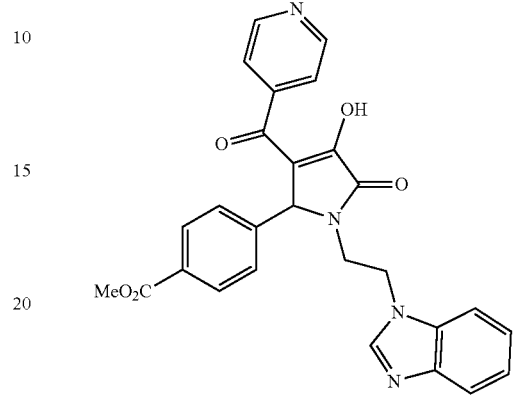

Methyl 4-(1-(2-(1H-benzo[d]imidazol-1-yl)ethyl)-4-hydroxy-3-isonicotinoyl-5-oxo-2,5-dihydro-1H-pyrrol-2-yl)benzoate (1616-56). Compound 1616-56 was prepared via the general procedure A from methyl 4-formylbenzoate (0.19 g, 1.1 mmol), 2-(1H-benzo[d]imidazol-1-yl)ethanamine (0.18 g, 1.1 mmol) and (Z)-ethyl 2-hydroxy-4-oxo-4-(pyridin-4-yl)but-2-enoate (0.25 g, 1.1 mmol) to yield a yellow solid (0.40 g, 73%). $^1$H NMR (400 MHz, DMSO-d$^6$) δ 8.66 (d, J=1.3 Hz, 2H), 8.59 (s, 1H), 7.80 (d, J=8.4 Hz, 2H), 7.67 (t, J=5.2 Hz, 1H), 7.61 (t, J=5.2 Hz, 1H), 7.52 (d, J=5.6 Hz, 2H), 7.33-7.29 (mult, 4H), 5.37 (s, 1H), 4.61-4.54 (mult, 1H), 4.48-4.44 (mult, 1H), 4.03-3.98 (mult, 1H), 3.82 (s, 3H), 3.08-3.04 (mult, 1H).

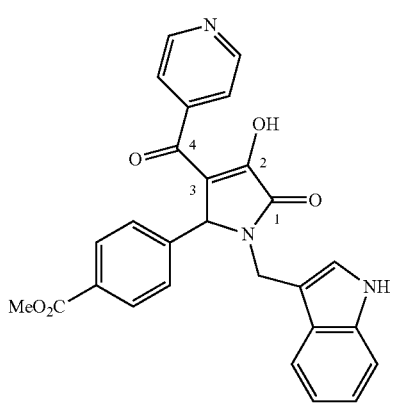 [SMILES: COC(=O)c1ccc(C2C(C(=O)c3ccncc3)=C(O)C(=O)N2Cc2c[nH]c3ccccc23)cc1]

Methyl 4-(1-((1H-indol-3-yl)methyl)-4-hydroxy-3-isonicotinoyl-5-oxo-2,5-dihydro-1H-pyrrol-2-yl)benzoate (1616-55). Compound 1616-55 was prepared via the general procedure A from methyl 4-formylbenzoate (0.28 g, 1.7 mmol), (1H-indol-3-yl)methanamine (0.25 g, 1.7 mmol) and 1616-

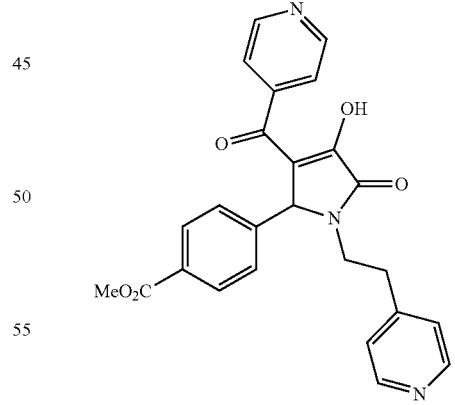

Methyl 4-(4-hydroxy-3-isonicotinoyl-5-oxo-1-(2-(pyridin-4-yl)ethyl)-2,5-dihydro-1H-pyrrol-2-yl)benzoate (1616-57). Compound 1616-57 was prepared via the general procedure A from methyl 4-formylbenzoate (0.19 g, 1.1 mmol), 2-(pyridin-4-yl)ethanamine (0.14 g, 1.1 mmol) and (Z)-ethyl 2-hydroxy-4-oxo-4-(pyridin-4-yl)but-2-enoate (0.25 g, 1.1 mmol) to yield a yellow solid (0.47 g, 95%).

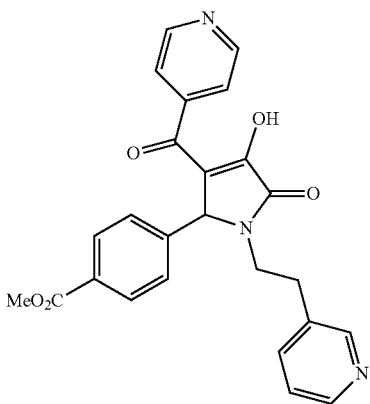 [SMILES: COC(=O)c1ccc(C2C(C(=O)c3ccncc3)=C(O)C(=O)N2CCc2cccnc2)cc1]

Methyl 4-(4-hydroxy-3-isonicotinoyl-5-oxo-1-(2-(pyridin-3-yl)ethyl)-2,5-dihydro-1H-pyrrol-2-yl)benzoate (1616-58). Compound 1616-58 was prepared via the general procedure A from methyl 4-formylbenzoate (0.19 g, 1.1 mmol), 2-(pyridin-3-yl)ethanamine (0.14 g, 1.1 mmol) and (Z)-ethyl 2-hydroxy-4-oxo-4-(pyridin-4-yl)but-2-enoate (0.25 g, 1.1 mmol) to yield a yellow solid (0.47 g, 93%).

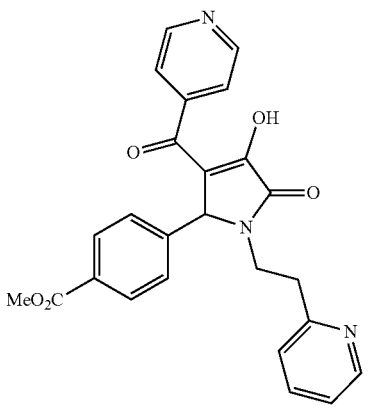 [SMILES: COC(=O)c1ccc(C2C(C(=O)c3ccncc3)=C(O)C(=O)N2CCc2ccccn2)cc1]

Methyl 4-(4-hydroxy-3-isonicotinoyl-5-oxo-1-(2-(pyridin-2-yl)ethyl)-2,5-dihydro-1H-pyrrol-2-yl)benzoate (1616-59). Compound 1616-59 was prepared via the general procedure A from methyl 4-formylbenzoate (0.19 g, 1.1 mmol), 2-(pyridin-2-yl)ethanamine (0.14 g, 1.1 mmol) and (Z)-ethyl 2-hydroxy-4-oxo-4-(pyridin-4-yl)but-2-enoate (0.25 g, 1.1 mmol) to yield a yellow solid (0.50 g, >99%).

((Triisopropylsilyl)oxy)phenyl)ethanone (1616-62a). Compound 1616-62a was prepared via Procedure J from 1-(3-hydroxyphenyl)ethanone (3.0 g, 22 mmol) to yield a yellow oil (6.4 g, >99%).

(Z)-Ethyl 2-hydroxy-4-oxo-4-(3-((triisopropylsilyl)oxy)phenyl)but-2-enoate (1616-62b). Compound 1616-62b was prepared via Procedure H from 1616-62a (8.8 g, 30 mmol) to yield a yellow oil which was taken on without further attempts at purification.

(Z)-Ethyl 2-hydroxy-4-(3-hydroxyphenyl)-4-oxobut-2-enoate (1616-62c). Compound 1616-62c was prepared via Procedure K from 1616-62b (3.3 g, 8.5 mmol) to yield a pale yellow solid (0.86 g, 43%).

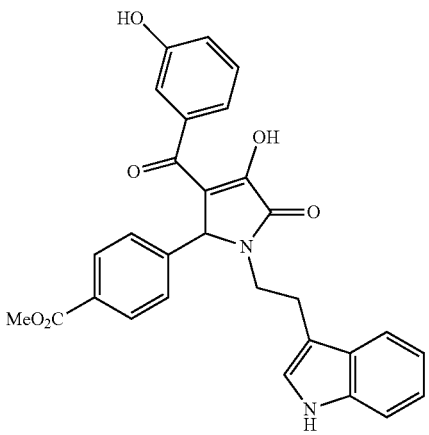 [SMILES: COC(=O)c1ccc(C2C(C(=O)c3cccc(O)c3)=C(O)C(=O)N2CCc2c[nH]c3ccccc23)cc1]

Methyl 4-(1-(2-(1H-indol-3-yl)ethyl)-4-hydroxy-3-(3-hydroxybenzoyl)-5-oxo-2,5-dihydro-1H-pyrrol-2-yl)benzoate (1616-62). Compound 1616-62 was prepared via the general procedure A from methyl 4-formylbenzoate (0.35 g, 2.1 mmol), tryptamine (0.34 g, 2.1 mmol) and (Z)-ethyl 2-hydroxy-4-(3-hydroxyphenyl)-4-oxobut-2-enoate (0.50 g, 2.1 mmol) to yield a cream colored solid (1.0 g, 96%). $^1$H NMR (600 MHz, DMSO-d$^6$) δ 10.77 (s, 1H), 7.83 (d, J=7.8 Hz, 2H), 7.37-7.29 (mult, 6H), 7.13-7.12 (mult, 1H), 7.07-7.03 (mult, 3H), 6.91 (t, J=7.8 Hz, 1H), 5.36 (s, 1H), 3.87-3.81 (mult, 4H), 3.00-2.93 (mult, 2H), 2.78-2.73 (mult, 1H).

2-(Naphthalen-1-yl)ethanamine (1616-63a). 2-(Naphthalen-1-yl)acetonitrile (0.89 mL, 6.0 mmol) in diethyl ether (5.0 mL, 1.2 M) was added dropwise to a solution of lithium aluminum hydride (12 mL, 12 mmol, 2.0 equiv) in diethyl ether (20 mL, 0.30 M). The suspension was then allowed to stir at rt for 12 hrs. Water was added dropwise until no more gas was given off, at which point 1.0 M NaOH was added to pH=9. The mixture was extracted with Et$_2$O (2×) and washed with brine. The combined organic layers were dried over MgSO$_4$, filtered and concentrated in vacuo. Purification was achieved via flash column chromatography on SiO$_2$ (10% MeOH/DCM) to yield a yellow oil (0.41 g, 40%).

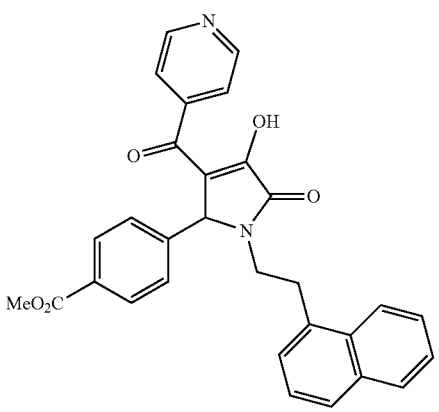 [SMILES: COC(=O)c1ccc(C2C(C(=O)c3ccncc3)=C(O)C(=O)N2CCc2cccc3ccccc23)cc1]

Methyl 4-(4-hydroxy-3-isonicotinoyl-1-(2-(naphthalen-1-yl)ethyl)-5-oxo-2,5-dihydro-1H-pyrrol-2-yl)benzoate (1616-63). Compound 1616-63 was prepared via the general procedure A from methyl 4-formylbenzoate (0.40 g, 2.4 mmol), 2-(naphthalen-1-yl)ethanamine (0.41 g, 2.4 mmol) and (Z)-ethyl 2-hydroxy-4-oxo-4-(pyridin-4-yl)but-2-enoate (0.53 g, 2.4 mmol) to yield a yellow solid (0.67 g, 56%). $^1$H NMR (600 MHz, DMSO-d⁶) δ 8.70 (d, J=3.6 Hz, 2H), 7.93-7.84 (mult, 4H), 7.81 (d, J=7.8 Hz, 1H), 7.57-7.40 (mult, 7H), 7.30 (d, J=6.6 Hz, 1H), 5.40 (s, 1H), 3.84-3.80 (mult, 4H), 3.37-3.34 (mult, 1H), 3.13-3.08 (mult, 1H), 3.03-3.00 (mult, 1H).

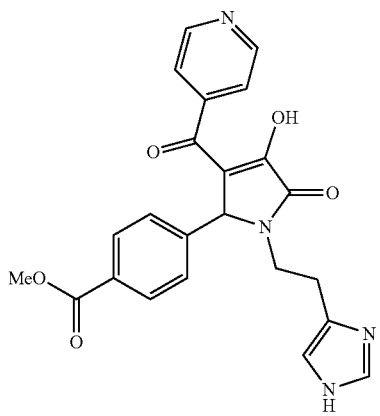 [SMILES: COC(=O)c1ccc(C2C(C(=O)c3ccncc3)=C(O)C(=O)N2CCc2c[nH]cn2)cc1]

Methyl 4-(1-(2-(1H-imidazol-4-yl)ethyl)-4-hydroxy-3-isonicotinoyl-5-oxo-2,5-dihydro-1H-pyrrol-2-yl)benzoate (1616-64). Compound 1616-64 was prepared via the general procedure A from methyl 4-formylbenzoate (0.37 g, 2.3 mmol), 2-(1H-imidazol-4-yl)ethanamine (0.25 g, 2.3 mmol) and (Z)-ethyl 2-hydroxy-4-oxo-4-(pyridin-4-yl)but-2-enoate (0.50 g, 2.3 mmol) to yield an orange solid (0.031 g, 3%).

N-(2-(1H-indol-3-yl)ethyl)-2,2,2-trifluoroacetamide (1616-65a). To a solution of 2-(1H-indol-3-yl)ethanamine (2.0 g, 12 mmol) in DCM (112 mL, 0.11 M) at 0° C. was added pyridine (11 mL, 140 mmol, 11 equiv). 2,2,2-Trifluoroacetic anhydride (1.9 mL, 13 mmol, 1.1 equiv) was added dropwise and the reaction continued to stir at 0° C. for 5 min before being warmed to rt and stirred for 2 hrs. The resulting mixture was diluted with DCM and washed with saturated sodium bicarbonate, brine and water. The combined organic layers were dried over MgSO₄, filtered and concentrated in vacuo. Purification was achieved via flash column chromatography on SiO₂ (Hexanes/EtOAc: 3/1) to yield a pale yellow solid (2.5 g, 79%).

tert-Butyl 3-(2-(2,2,2-trifluoroacetamido)ethyl)-1H-indole-1-carboxylate (1616-65b). To a solution of 1616-65a (2.5 g, 9.8 mmol) in THF (98 mL, 0.10 M) was added di-tert-butyl dicarbonate (2.7 mL, 12 mmol, 1.2 equiv) and N,N-dimethylpyridin-4-amine (0.060 g, 0.49 mmol). The resulting mixture was warmed to 40° C. and stirred for 1 hr. The reaction was diluted with DCM and washed with water before being dried over MgSO₄, filtered and concentrated in vacuo. Purification was achieved via flash column chromatography on SiO₂ (Hexanes/EtOAc: 10/1) to yield a yellow residue (2.7 g, 76%) which was carried on without further attempts at purification.

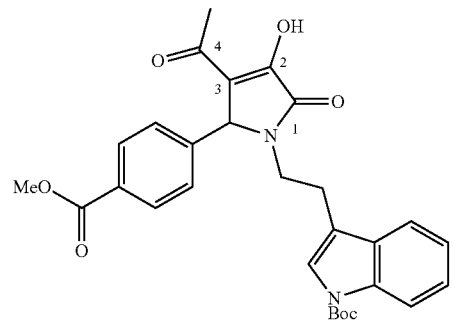 [SMILES: COC(=O)c1ccc(C2C(C(C)=O)=C(O)C(=O)N2CCc2cn(C(=O)OC(C)(C)C)c3ccccc23)cc1]

tert-Butyl-3-(2-(3-acetyl-4-hydroxy-2-(4-(methoxycarbonyl)phenyl)-5-oxo-2,5-dihydro-1H-pyrrol-1-yl)ethyl)-1H-indole-1-carboxylate (1616-65). To a solution of tert-butyl 3-(2-(2,2,2-trifluoroacetamido)ethyl)-1H-indole-1-carboxylate (2.7 g, 7.5 mmol) in MeOH:Water (2:1, 0.10 M) was added finely ground potassium carbonate (3.7 g, 27 mmol). The resulting mixture was stirred at rt for 48 hrs before being diluted with water and extracted with DCM (2×). The combined organic layers were dried over MgSO₄, filtered and concentrated in vacuo to yield an orange oil which was taken on without further purification. The crude material was then combined with methyl 4-formylbenzoate (1.1 g, 6.9 mmol) and methyl acetopyruvate (1.0 g, 6.9 mmol) and carried on through the general procedure A to yield a cream colored solid (2.2 g, 60%). ¹H NMR (400 MHz, DMSO-d⁶) δ 8.15 (d, J=8.4 Hz, 1H), 8.03 (d, J=8.4 Hz, 1H), 7.87 (d, J=8.4 Hz, 2H), 7.39 (s, 1H), 7.33-7.27 (mult, 3H), 7.17 (t, J=7.6 Hz, 1H), 5.35 (s, 1H), 3.88-3.76 (mult, 4H), 2.93-2.87 (mult, 2H), 2.80-2.73 (mult, 1H), 2.28 (s, 3H), 1.60 (s, 9H).

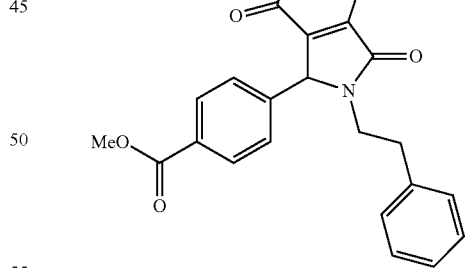

Methyl 4-(3-acetyl-4-hydroxy-5-oxo-1-phenethyl-2,5-dihydro-1H-pyrrol-2-yl)benzoate (1616-66). Compound 1616-66 was prepared via the general procedure A from methyl 4-formylbenzoate (0.34 g, 2.1 mmol), ethyl acetopyruvate (0.33 g, 2.1 mmol) and 2-phenylethanamine (0.25 g, 2.1 mmol) to yield a white solid (0.73 g, 93

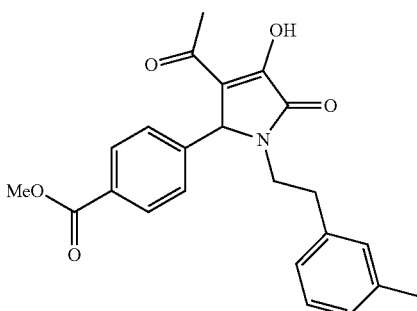

Methyl 4-(3-acetyl-4-hydroxy-1-(3-methylphenethyl)-5-oxo-2,5-dihydro-1H-pyrrol-2-yl)benzoate (1616-67). Compound 1616-67 was prepared via the general procedure A from methyl 4-formylbenzoate (0.30 g, 1.8 mmol), ethyl acetopyruvate (0.29 g, 1.8 mmol) and 2-(m-tolyl)ethanamine (0.25 g, 1.8 mmol) to yield a white solid (0.56 g, 76%).

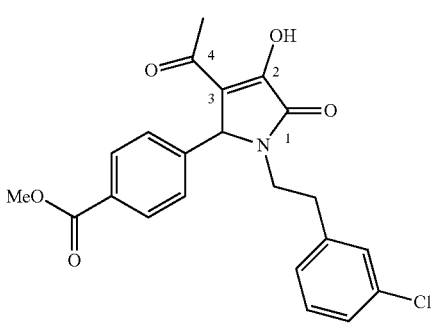 [SMILES: COC(=O)c1ccc(C2C(C(C)=O)=C(O)C(=O)N2CCc2cccc(Cl)c2)cc1]

Methyl 4-(3-acetyl-1-(3-chlorophenethyl)-4-hydroxy-5-oxo-2,5-dihydro-1H-pyrrol-2-yl)benzoate (1616-68). Compound 1616-68 was prepared via the general procedure A from methyl 4-formylbenzoate (0.26 g, 1.6 mmol), ethyl acetopyruvate (0.25 g, 1.6 mmol) and 2-(3-chlorophenyl)ethanamine (0.25 g, 1.6 mmol) to yield a pale yellow solid (0.50 g, 76%).

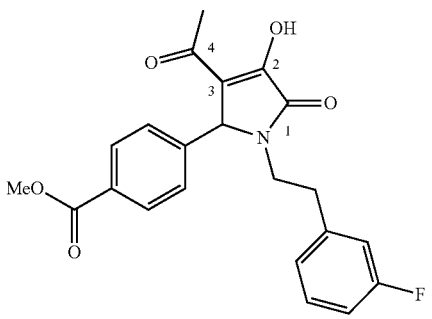 [SMILES: COC(=O)c1ccc(C2C(C(C)=O)=C(O)C(=O)N2CCc2cccc(F)c2)cc1]

Methyl 4-(3-acetyl-1-(3-fluorophenethyl)-4-hydroxy-5-oxo-2,5-dihydro-1H-pyrrol-2-yl)benzoate (1616-69). Compound 1616-69 was prepared via the general procedure A from methyl 4-formylbenzoate (0.30 g, 1.8 mmol), ethyl acetopyruvate (0.28 g, 1.8 mmol) and 2-(3-fluorophenyl)ethanamine (0.25 g, 1.8 mmol) to yield an off-white solid (0.57 g, 79%).

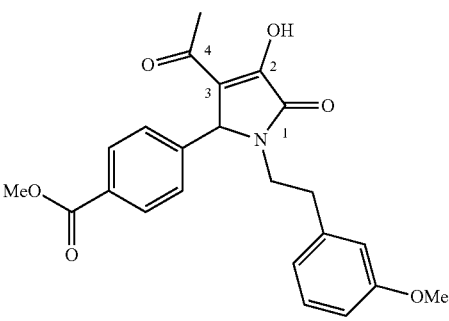 [SMILES: COC(=O)c1ccc(C2C(C(C)=O)=C(O)C(=O)N2CCc2cccc(OC)c2)cc1]

Methyl 4-(3-acetyl-4-hydroxy-1-(3-methoxyphenethyl)-5-oxo-2,5-dihydro-1H-pyrrol-2-yl)benzoate (1616-70). Compound 1616-70 was prepared via the general procedure A from methyl 4-formylbenzoate (0.27 g, 1.7 mmol), ethyl acetopyruvate (0.26 g, 1.7 mmol) and 2-(3-methoxyphenyl)ethanamine (0.25 g, 1.7 mmol) to yield an off-white solid (0.52 g, 76%).

3-(2-aminoethyl)phenol (1616-71a). To a solution of 2-(3-methoxyphenyl)ethanamine (1.0 g, 6.6 mmol) in acetic acid (3.97 mL, 1.7 M) was added 48% 48% hydrogen bromide solution (4.0 mL, 35 mmol, 5.3 equiv). The resulting mixture was brought to reflux and stirred for 4 hrs. The mixture was then cooled to rt and concentrated in vacuo. The residue was dissolved in MeOH and concentrated down 4 times to afford a brown crystalline solid. The solid was dissolved in minimal DCM and triethylamine (2.8 mL, 20 mmol, 3.0 equiv) was added. After stirring for 2 hrs the mixture was washed with water and brine, dried over $MgSO_4$, filtered and concentrated in vacuo to afford an orange oil (0.46 g, 51%).

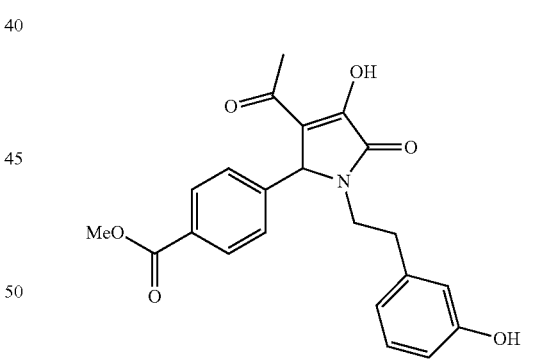

Methyl 4-(3-acetyl-4-hydroxy-1-(3-hydroxyphenethyl)-5-oxo-2,5-dihydro-1H-pyrrol-2-yl)benzoate (1616-71). Compound 1616-71 was prepared via the general procedure A from methyl 4-formylbenzoate (0.55 g, 3.4 mmol), ethyl acetopyruvate (0.53 g, 3.4 mmol) and 3-(2-aminoethyl)phenol (0.46 g, 3.4 mmol) to yield a cream colored solid (1.0 g, 78%). $^1$H NMR (400 MHz, DMSO-d$^6$) δ 9.34 (br s, 1H), 7.93 (d, J=8.8 Hz, 2H), 7.33 (d, J=8.8 Hz, 2H), 7.08 (t, J=7.6 Hz, 1H), 6.61 (dt, J=1.6 Hz, J=6.8 Hz, 1H), 6.54-6.52 (mult, 2H), 5.16 (s, 1H), 3.87-3.83 (mult, 4H), 2.74-2.69 (mult, 2H), 2.56-2.52 (mult, 1H), 2.30 (s, 3H).

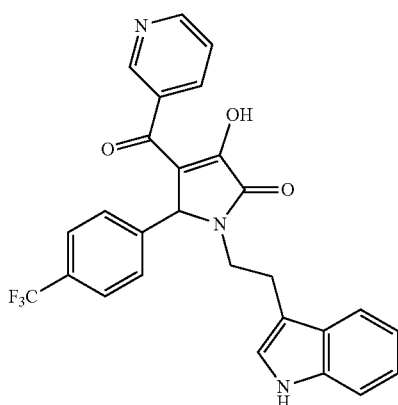

1-(2-(1H-indol-3-yl)ethyl)-3-hydroxy-4-nicotinoyl-5-(4-(trifluoromethyl)phenyl)-1H-pyrrol-2(5H)-one (1616-72). Compound 1616-72 was prepared via Procedure A from 4-(trifluoromethyl)benzaldehyde (0.17 g, 1.0 mmol), 1616-28a (0.22 g, 1.0 mmol) and tryptamine (0.16 g, 1.0 mmol) to yield a yellow solid (0.24 g, 49%). $^1$H NMR (600 MHz, DMSO-$d_6$) δ 10.94 (s, 1H), 8.83 (d, J=1.2 Hz, 1H), 8.70 (dd, J=1.8 Hz, J=4.8 Hz, 1H), 8.20 (br s, 1H), 8.04 (d, J=8.4 Hz, 1H), 7.66 (d, J=7.8 Hz, 2H), 7.54-7.48 (mult, 3H), 7.34 (d, J=8.4 Hz, 1H), 7.24 (d, J=7.8 Hz, 1H), 7.13 (s, 1H), 7.05 (t, J=7.8 Hz, 1H), 6.91 (t, J=7.2 Hz, 1H), 5.46 (s, 1H), 3.88-3.83 (mult, 1H), 3.02-2.92 (mult, 2H), 2.78-2.73 (mult, 1H).

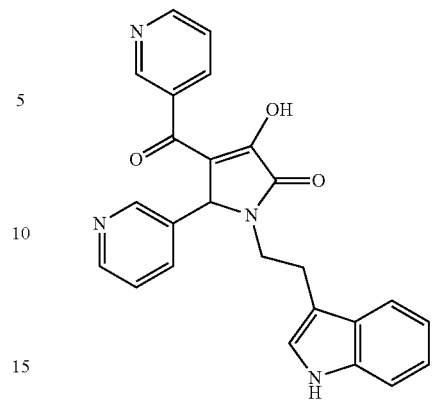

1-(2-(1H-indol-3-yl)ethyl)-3-hydroxy-4-nicotinoyl-5-(pyridine-3-yl)-1H-pyrrol-2(5H)-one (1616-74). Compound 1616-74 was prepared via Procedure A from nicotinaldehyde (0.11 g, 1.0 mmol), 1616-28a (0.22 g, 1.0 mmol) and tryptamine (0.16 g, 1.0 mmol) to yield an orange solid (0.29 g, 67%). $^1$H NMR (600 MHz, DMSO-$d_6$) δ 10.90 (s, 1H), 8.83 (d, J=2.4 Hz, 1H), 8.68 (dd, J=1.8 Hz, J=4.8 Hz, 1H), 8.57 (d, J=1.8 Hz, 1H), 8.49 (dd, J=2.4 Hz, J=4.8 Hz, 1H), 8.04 (dt, J=1.8 Hz, J=7.8 Hz, 1H), 7.74 (d, J=8.4 Hz, 1H), 7.49-7.47 (mult, 1H), 7.36-7.32 (mult, 3H), 7.24 (s, 1H), 7.13 (d, J=1.8 Hz, 1H), 7.06 (t, J=7.8 Hz, 1H), 6.94 (t, J=8.4 Hz, 1H), 5.39 (s, 1H), 3.89-3.85 (mult, 1H), 3.02-2.93 (mult, 2H), 2.79-2.75 (mult, 1H).

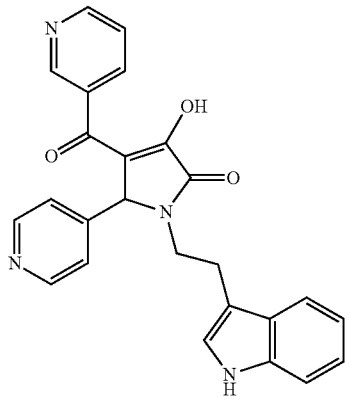 [SMILES: O=C(C1=C(O)C(=O)N(CCc2c[nH]c3ccccc23)C1c1ccncc1)c1cccnc1]

1-(2-(1H-indol-3-yl(ethyl)-3-hydroxy-4-nicotinoyl-5-(pyridine-4-yl)-1H-pyrrol-2(5H)-one (1616-73). Compound 1616-73 was prepared via Procedure A from isonicotinaldehyde (0.11 g, 1.0 mmol), 1616-28a (0.22 g, 1.0 mmol) and tryptamine (0.16 g, 1.0 mmol) to yield a mustard-colored solid (0.32 g, 76%). $^1$H NMR (600 MHz, DMSO-$d_6$) δ 10.93 (s, 1H), 8.84 (d, J=1.8 Hz, 1H), 8.67 (dd, J=1.8 Hz, J=4.8 Hz, 1H), 8.53 (d, J=5.4 Hz, 2H), 8.05 (dt, J=2.4 Hz, J=8.4 Hz, 1H), 7.49-7.47 (mult, 2H), 7.42-7.34 (mult, 3H), 7.30 (br s, 1H), 7.13 (d, J=1.8 Hz, 1H), 7.06 (t, J=7.8 Hz, 1H), 6.94 (t, J=8.4 Hz, 1H), 5.34 (s, 1H), 3.92-3.87 (mult, 1H), 3.02-2.91 (mult, 2H), 2.82-2.77 (mult, 1H).

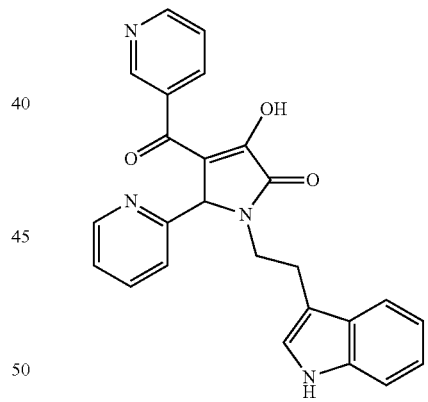

1-(2-(1H-indol-3-yl)ethyl)-3-hydroxy-4-nicotinoyl-5-(pyridine-2-yl)-1H-pyrrol-2(5H)-one (1616-75). Compound 1616-75 was prepared via Procedure A from picolinaldehyde (0.11 g, 1.0 mmol), 1616-28a (0.22 g, 1.0 mmol) and tryptamine (0.16 g, 1.0 mmol) to yield a yellow solid (0.30 g, 71%). $^1$H NMR (600 MHz, DMSO-$d_6$) δ 10.91 (s, 1H), 8.80 (d, J=1.2 Hz, 1H), 8.69 (dd, J=1.2 Hz, J=4.8 Hz, 8.55 (d, J=4.2 Hz, 1H), 8.00 (d, J=7.2 Hz, 1H), 7.77 (td, J=1.2 Hz, J=7.2 Hz, 1H), 7.50-7.46 (mult, 2H), 7.38-7.30 (mult, 4H), 7.12 (d, J=1.8 Hz, 1H), 7.05 (t, J=7.8 Hz, 1H), 6.95 (t, J=7.8 Hz, 1H), 5.54 (s, 1H), 3.87-3.82 (mult, 1H), 3.01-2.91 (mult, 2H), 2.72-2.67 (mult, 1H).

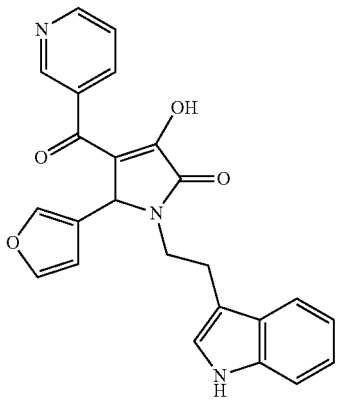
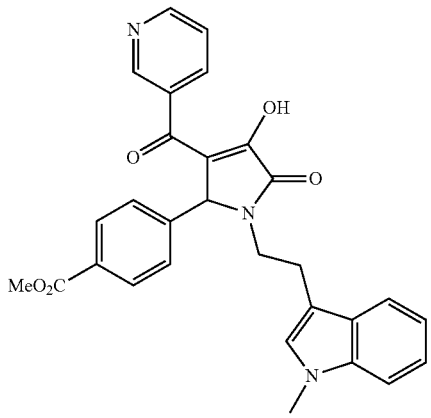

1-(2-(1H-indol-3-yl)ethyl)-5-(furan-3-yl)-3-hydroxy-4-nicotinoyl-1H-pyrrol-2(5H)-one (1616-76). Compound 1616-76 was prepared via Procedure A from furan-3-carbaldehyde (0.10 g, 1.0 mmol), 1616-28a (0.22 g, 1.0 mmol) and tryptamine (0.16 g, 1.0 mmol) to yield an orange solid (0.12 g, 28%). $^1$H NMR (600 MHz, DMSO-d$_6$) δ 10.86 (s, 1H), 8.85 (d, J=1.8 Hz, 1H), 8.71 (dd, J=1.2 Hz, J=4.8 Hz, 1H), 8.05 (dt, J=1.8 Hz, J=7.8 Hz, 1H), 7.74 (s, 1H), 7.50-7.48 (mult, 1H), 7.45 (d, J=7.8 Hz, 1H), 7.34 (d, J=7.8 Hz, 1H), 7.18 (s, 1H), 7.15 (d, J=1.8 Hz, 1H), 7.10 (s, 1H), 7.07 (t, J=7.2 Hz, 1H), 6.98 (t, J=7.8 Hz, 1H), 6.48 (d, J=1.2 Hz, 1H), 5.40 (s, 1H), 3.89-3.84 (mult, 1H), 3.12-3.00 (mult, 2H), 2.84-2.80 (mult, 1H).

Methyl 4-(4-hydroxy-1-(2-(1-methyl-1H-indol-3-yl)ethyl)-3-nicotinoyl-5-oxo-2,5-dihydro-1H-pyrrol-2-yl)benzoate (1616-79). Compound 1616-79 was prepared from methyl 4-formylbenzoate (0.16 g, 1.0 mmol), 1616-28a (0.22 g, 1.0 mmol) and 2-(1-methyl-1H-indol-3-yl)ethanamine (0.17 g, 1.0 mmol) to yield cream colored solid (0.21 g, 43%). $^1$H NMR (600 MHz, DMSO-d$_6$) δ 8.81 (d, J=1.8 Hz, 1H), 8.70 (dd, J=1.8 Hz, J=4.8, 1H), 8.01 (dt, J=1.8 Hz, 8.4 Hz, 1H), 7.88 (d, J=8.4 Hz, 2H), 7.50-7.46 (mult, 3H), 7.36 (d, J=9.0 Hz, 1H), 7.32 (d, J=8.4 Hz, 1H), 7.14-7.10 (mult, 2H), 6.96 (t, J=7.8 Hz, 1H), 5.50 (s, 1H), 3.85-3.80 (mult, 4H), 3.70 (s, 3H), 3.00-2.92 (mult, 2H), 2.76-2.72 (mult, 1H).

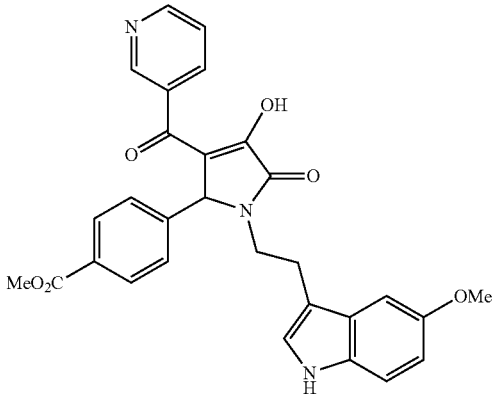 [SMILES: COC(=O)c1ccc(C2C(C(=O)c3cccnc3)=C(O)C(=O)N2CCc2c[nH]c3ccc(OC)cc23)cc1]
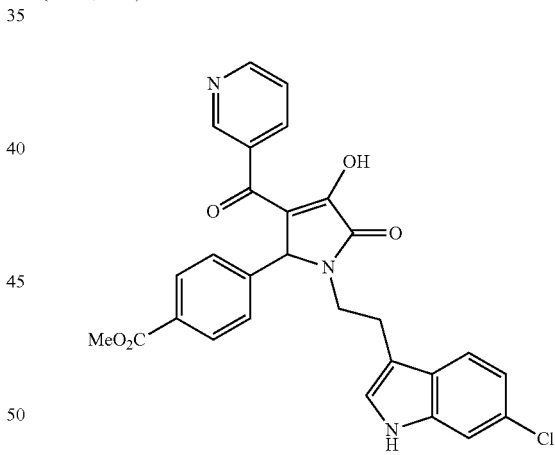

Methyl 4-(4-hydroxy-1-(2-(5-methoxy-1H-indol-3-yl)ethyl)-3-nicotinoyl-5-oxo-2,5-dihydro-1H-pyrrol-2-yl)benzoate (1616-77). Compound 1616-77 was prepared via Procedure A from methyl 4-formylbenzoate (0.16 g, 1.0 mmol), 1616-28a (0.22 g, 1.0 mmol) and 2-(5-methoxy-1H-indol-3-yl)ethanamine (0.19 g, 1.0 mmol) to yield a yellow solid (0.35 g, 68%). $^1$H NMR (600 MHz, DMSO-d$_6$) δ 10.72 (s, 1H), 8.79 (d, J=1.8 Hz, 1H), 8.68 (dd, J=1.8 Hz, J=4.8 Hz, 1H), 7.99 (dt, J=1.8 Hz, J=7.8 Hz, 1H), 7.88 (d, J=8.4 Hz, 2H), 7.48-7.46 (mult, 1H), 7.44 (d, J=7.8 Hz, 2H), 7.22-7.21 (mult, 2H), 7.09 (d, J=2.4 Hz, 1H), 6.75 (d, J=2.4 Hz, 1H), 6.70 (dd, J=2.4 Hz, J=9.0 Hz, 1H), 5.44 (s, H), 3.85-3.80 (mult, 4H), 2.68 (s, 3H), 2.98-2.89 (mult, 2H), 2.73-2.70 (mult, 1H).

Methyl 4-(1-(2-(6-chloro-1H-indol-3-yl)ethyl)-4-hydroxy-3-nicotinoyl-5-oxo-2,5-dihydro-1H-pyrrol-2-yl)benzoate (1616-80). Compound 1616-80 was prepared from methyl 4-formylbenzoate (0.16 g, 1.0 mmol), 1616-28a (0.22 g, 1.0 mmol) and 2-(6-chloro-1H-indol-3-yl)ethanamine (0.20 g, 1.0 mmol) to yield a yellow solid (0.44 g, 85%). $^1$H NMR (600 MHz, DMSO-d$_6$) δ 11.00 (s, 1H), 8.80 (s, 1H), 8.68 (d, J=3.6 Hz, 1H), 8.00 (d, J=8.4 Hz, 1H), 7.87 (d, J=7.8 Hz, 2H), 7.77 (br s, 1H), 7.48-7.41 (mult, 3H), 7.37 (d, J=1.2 Hz, 1H), 7.33 (d, J=8.4 Hz, 1H), 7.17 (s, 1H), 6.94 (dd, J=1.2 Hz, J=8.4 Hz, 1H), 3.87-3.82 (mult, 4H), 2.97-2.89 (mult, 2H), 2.79-2.76 (mult, 1H).

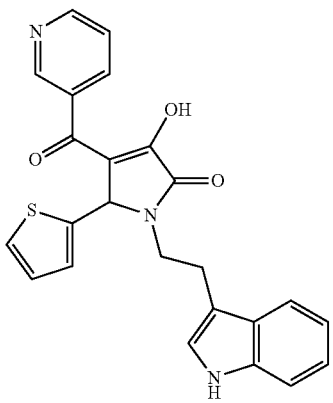 [SMILES: O=C(C1=C(O)C(=O)N(CCc2c[nH]c3ccccc23)C1c1cccs1)c1cccnc1]

1-(2-(1H-indol-3-yl)ethyl)-3-hydroxy-4-nicotinoyl-5-(thiophen-2-yl)-1H-pyrrol-2(5H)-one (1616-81). Compound 1616-81 was prepared from thiophene-2-carbaldehyde (0.11 g, 1.0 mmol), 1616-28a (0.22 g, 1.0 mmol) and tryptamine (0.16 g, 1.0 mmol) to yield an orange solid (0.07 g, 16%). $^1$H NMR (600 MHz, DMSO-$d_6$) δ 10.87 (s, 1H), 8.81 (s, 1H), 8.72 (d, J=4.8 Hz, 1H), 8.02 (dd, J=1.8 Hz, J=6.0 Hz, 1H), 7.53-7.51 (mult, 1H), 7.48-7.44 (mult, 2H), 7.34 (d, J=7.8 Hz, 1H), 7.20 (d, J=3.0 Hz, 1H), 7.15 (d, J=1.8 Hz, 1H), 7.07 (t, J=7.8 Hz, 2H), 7.00-6.96 (mult, 2H), 5.76 (s, 1H), 3.87-3.83 (mult, 1H), 3.14-3.09 (mult, 1H), 3.05-3.00 (mult, 1H), 2.77-2.72 (mult, 1H).

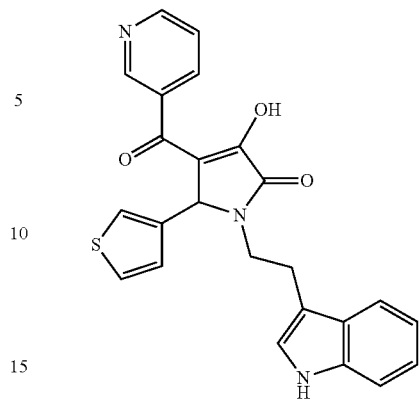

1-(2-(1H-indol-3-yl)ethyl)-3-hydroxy-4-nicotinoyl-5-(thiophen-3-yl)-1H-pyrrol-2(5H)-one (1616-83). Compound 1616-83 was prepared from thiophene-3-carbaldehyde (0.11 g, 1.0 mmol), 1616-28a (0.22 g, 1.0 mmol) and tryptamine (0.16 g, 1.0 mmol) to yield a yellow solid (0.11 g, 25%). $^1$H NMR (600 MHz, DMSO-$d_6$) δ 10.87 (s, 1H), 8.86 (s, 1H), 8.71 (d, J=4.8 Hz, 1H), 8.06 (d, J=7.8 Hz, 1H), 7.70 (d, J=1.8 Hz, 1H), 7.50-7.47 (mult, 2H), 7.40 (d, J=7.8 Hz, 1H), 7.34 (d, J=7.8 Hz, 1H), 7.25 (s, 1H), 7.14 (s, 1H), 7.08-7.06 (mult, 2H), 6.96 (t, J=7.8 Hz, 1H), 5.55 (s, 1H), 3.86-3.80 (mult, 1H), 3.06-2.98 (mult, 2H), 2.76-2.70 (mult, 1H).

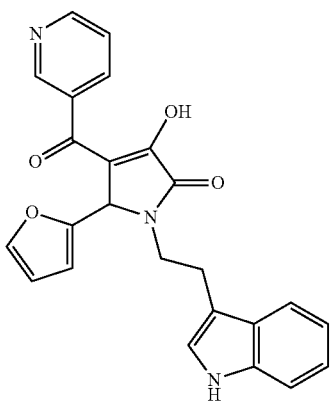 [SMILES: O=C(C1=C(O)C(=O)N(CCc2c[nH]c3ccccc23)C1c1ccco1)c1cccnc1]

1-(2-(1H-indol-3-yl)ethyl)-5-(furan-2-yl)-3-hydroxy-4-nicotinoyl-1H-pyrrol-2(5H)-one (1616-82). Compound 1616-82 was prepared from furfural (0.10 g, 1.0 mmol), 1616-28a (0.22 g, 1.0 mmol) and tryptamine (0.16 g, 1.0 mmol) to yield a mustard colored solid (0.06 g, 14%). $^1$H NMR (600 MHz, DMSO-$d_6$) δ 10.87 (s, 1H), 8.82 (d, J=1.2 Hz, 1H), 8.72 (dd, J=1.8 Hz, J=4.8 Hz, 1H), 8.03 (dt, J=1.8 Hz, J=5.4 Hz, 1H), 7.62 (t, J=0.6 Hz, 1H), 7.53-7.52 (mult, 1H), 7.48 (d, J=7.8 Hz, 1H), 7.34 (d, J=7.8 Hz, 1H), 7.18 (s, 1H), 7.15 (d, J=2.4 Hz, 1H), 7.10-7.06 (mult, 2H), 6.99 (t, J=6.6 Hz, 1H), 6.52 (d, J=3.0 Hz, 1H), 6.433-6.425 (mult, 1H), 3.82-3.77 (mult, 1H), 3.19-3.14 (mult, 1H), 3.00-2.95 (mult, 1H), 2.66-2.61 (mult, 1H).

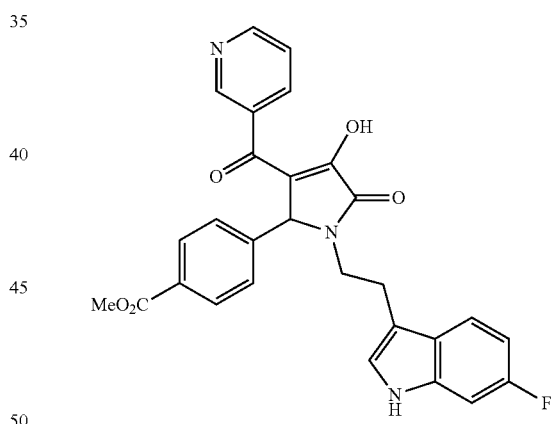

Methyl 4-(1-(2-(6-fluoro-1H-indol-3-yl)ethyl)-4-hydroxy-3-nicotinoyl-5-oxo-2,5-dihydro-1H-pyrrol-2-yl)benzoate (1616-84). Compound 1616-84 was prepared from methyl 4-formylbenzoate (0.16 g, 1.0 mmol), 1616-28a (0.22 g, 1.0 mmol) and 3-(6-fluoro-1H-indol-3-yl)ethanamine (0.18 g, 1.0 mmol) to yield a pale orange solid (0.44 g, 87%). $^1$H NMR (600 MHz, DMSO-$d_6$) δ 10.94 (s, 1H), 8.82 (d, J=0.6 Hz, 1H), 8.69 (d, J=4.8 Hz, 1H), 8.01 (d, J=7.8 Hz, 1H), 7.88 (d, J=8.4 Hz, 2H), 7.80 (br s, 1H), 7.49-7.47 (mult, 1H), 7.43 (d, J=7.8 Hz, 2H), 7.33-7.30 (mult, 1H), 7.31-7.10 (mult, 2H), 6.79 (td, J=9.6 Hz, J=1.8 Hz, 1H), 5.44 (s, 1H), 3.89-3.82 (mult, 4H), 2.98-2.91 (mult, 2H), 2.80-2.76 (mult, 1H).

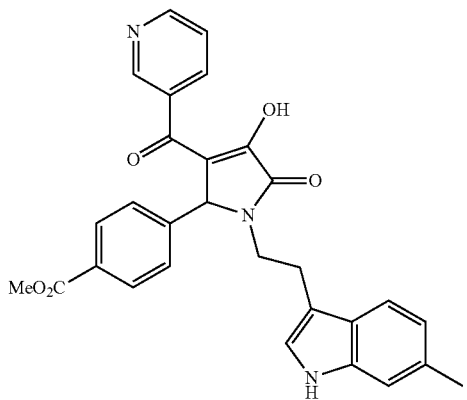 [SMILES: COC(=O)c1ccc(C2C(C(=O)c3cccnc3)=C(O)C(=O)N2CCc2c[nH]c3cc(C)ccc23)cc1]

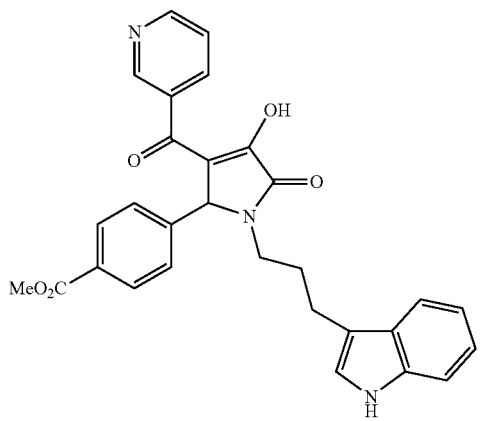

Methyl 4-(4-hydroxy-1-(2-(6-methyl-1H-indol-3-yl)ethyl)-3-nicotinoyl-5-oxo-2,5-dihydro-1H-pyrrol-2-yl)benzoate (1616-85). Compound 1616-85 was prepared from methyl 4-formylbenzoate (0.16 g, 1.0 mmol), 1616-28a (0.22 g, 1.0 mmol) and 2-(6-methyl-1H-indol-3-yl)ethanamine (0.17 g, 1.0 mmol) to yield a cream colored solid (0.10 g, 20%). $^1$H NMR (600 MHz, DMSO-$d_6$) δ 10.71 (s, 1H), 8.79 (s, 1H), 8.68 (d, J=3.6 Hz, 1H), 7.99 (d, J=6.6 Hz, 1H), 7.87 (d, J=7.8 Hz, 2H), 7.47 (t, J=6.0 Hz, 1H), 7.42 (d, J=7.8 Hz, 2H), 7.17 (d, J=7.8 Hz, 1H), 7.11 (s, 1H), 7.02 (s, 1H), 6.75 (d, J=7.8 Hz, 1H), 5.40 (s, 1H), 3.90-3.82 (mult, 4H), 2.99-2.89 (mult, 2H), 2.74-2.71 (mult, 1H), 2.37 (s, 3H).

Methyl 4-(1-(3-(1H-indol-3-yl)propyl)-4-hydroxy-3-nicotinoyl-5-oxo-2,5-dihydro-1H-pyrrol-2-yl)benzoate (1616-87). Compound 1616-87 was prepared from methyl 4-formylbenzoate (0.16 g, 1.0 mmol), 1616-28a (0.22 g, 1.0 mmol) and 3-(1H-indol-3-yl)propan-1-amine (0.17 g, 1.0 mmol) to yield a yellow solid (0.35 g, 71%). $^1$H NMR (600 MHz, DMSO-$d_6$) δ 10.75 (s, 1H), 8.82 (s, 1H), 8.69 (d, J=4.8 Hz, 1H), 8.02 (d, J=7.8 Hz, 1H), 7.87 (d, J=8.4 Hz, 2H), 7.49-7.47 (mult, 3H), 7.37 (d, J=7.8 Hz, 1H), 7.31 (d, J=8.4 Hz, 1H), 7.06-7.03 (mult, 2H), 6.92 (t, J=7.2 Hz, 1H), 5.54 (s, 1H), 3.62-3.55 (mult, 4H), 2.83-2.79 (mult, 1H), 2.62-2.55 (mult, 2H), 1.84-1.80 (mult, 1H), 1.73-1.69 (mult, 1H).

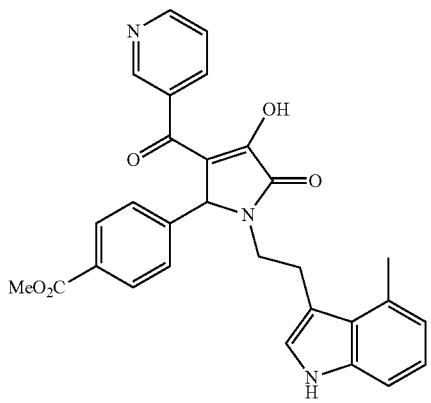 [SMILES: COC(=O)c1ccc(C2C(C(=O)c3cccnc3)=C(O)C(=O)N2CCc2c[nH]c3cccc(C)c23)cc1]

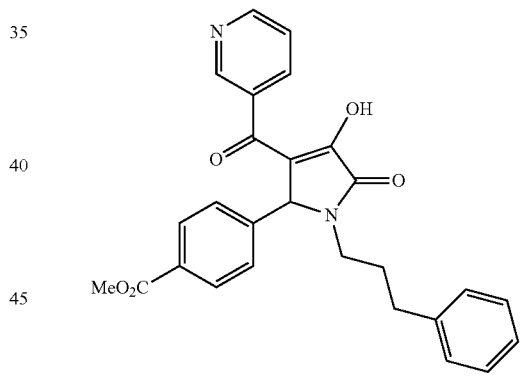

Methyl 4-(4-hydroxy-1-(2-(4-methyl-1H-indol-3-yl)ethyl)-3-nicotinoyl-5-oxo-2,5-dihydro-1H-pyrrol-2-yl)benzoate (1616-86). Compound 1616-86 was prepared from methyl 4-formylbenzoate (0.16 g, 1.0 mmol), 1616-28a (0.22 g, 1.0 mmol) and 2-(4-methyl-1H-indol-3-yl)ethanamine (0.17 g, 1.0 mmol) to yield a pale yellow solid (0.05 g, 11%). $^1$H NMR (600 MHz, DMSO-$d_6$) δ 10.84 (d, J=1.8 Hz, 1H), 8.82 (d, J=1.8 Hz, 1H), 8.70 (dd, J=1.8 Hz, J=4.8 Hz, 1H), 8.01 (dt, J=1.8 Hz, J=8.4 Hz, 1H), 7.88 (d, J=8.4 Hz, 2H), 7.49-7.44 (mult, 3H), 7.15 (d, J=8.4 Hz, 1H), 7.04 (d, J=2.4 Hz, 1H), 6.92 (t, J=6.6 Hz, 1H), 6.67 (d, J=7.2 Hz, 1H), 5.48 (s, 1H), 3.89-3.81 (mult, 4H), 3.14-3.09 (mult, 1H), 2.98-2.87 (mult, 2H), 2.44 (s, 3H).

Methyl 4-(4-hydroxy-3-nicotinoyl-5-oxo-1-(3-phenylpropyl)-2,5-dihydro-1H-pyrrol-2-yl)benzoate (1616-88). Compound 1616-88 was prepared from methyl 4-formylbenzoate (0.16 g, 1.0 mmol), 1616-28a (0.22 g, 1.0 mmol) and 3-phenylpropan-1-amine (0.14 g, 1.0 mmol) to yield a pale yellow solid (0.07 g, 16%). $^1$H NMR (600 MHz, DMSO-$d_6$) δ 8.81 (s, 1H), 8.68 (d, J=3.6 Hz, 1H), 8.02 (d, J=7.8 Hz, 1H), 7.89 (d, J=7.8 Hz, 2H), 7.52 (d, J=7.8 Hz, 2H), 7.47 (dd, J=4.8 Hz, J=7.8 Hz, 1H), 7.22 (d, J=7.2 Hz, 2H), 7.16-7.12 (mult, 3H), 5.54 (s, 1H), 3.82 (s, 3H), 3.59-3.54 (mult, 2H), 2.73-2.69 (mult, 2H), 1.74-1.65 (mult, 2H).

Oocyte NMDA Inhibition Assay

Two-electrode voltage-clamp recordings were made from *Xenopus laevis* oocytes expressing recombinant rat GluN1/GluN2A, GluN1/GluN2B, GluN1/GluN2C, GluN1/GluN2D, GluA1, or GluK2 receptors following injection of 5-10 ng of cRNA synthesized according to manufacturers' protocols (Ambin, mMessage, mMachine). cDNAs used were rat GluN1-1a (GenBank accession numbers U11418 and U08261; hereafter GluN1), GluN2A (D13211), GluN2B (U11419), GluN2C (M91563), GluN2D (L31611), GluA1 (X17184), GluK2 (Z11548). The current under voltage-clamp was recorded during perfusion with recording solution containing (in mM) 90 NaCl, 1.0 KCl, 0.5 $BaCl_2$, 0.005 EDTA, and 10 HEPES at pH 7.4 (23° C.). Glass micropipettes had resistances of 0.3-1.0 MS2 and were filled with 3.0 M KCl. The membrane potential was clamped at −40 mV during the experiment. Recordings were digitized at 10 Hz and analyzed off line. 20 mM stock solutions of test compounds in 100% DMSO were made and diluted to obtain the final concentration; final DMSO content was 0.05-0.5% (vol/vol). Oocytes expressing GluK2 homomeric receptors were first treated with 10 μM concanavalin A (10 minutes). NMDA receptor responses were obtained by challenging oocytes with 100 μM glutamate plus 30 μM glycine; GluA1 and GluK2 receptors responses were recorded during application of 100 μM glutamate. We recorded the response to 5-7 concentrations of test drug co-applied with glutamate and glycine in 5 or more oocytes obtained from two different frogs. We determined the $EC_{50}$ (half-maximally effective concentration of potentiator) by fitting the equation $$\text{Response} = (100 - \text{maximum})/(1 + (EC_{50}/[\text{concentration}])^N) + \text{maximum}$$

to the concentration-response data averaged across cells and normalized to the current in the absence of potentiator (100%). N is the Hill slope and maximum is the response predicted for saturating concentration of potentiator.

TABLE 1

Examples of determined activities via the assay described above.

| Compound | NR2A | NR2B | NR2C $IC_{50}$ (μM) | NR2D |
|---|---|---|---|---|
| (structure 1) | 91% response at 100 uM | 66% response at 100 uM | 4 | 64% response at 100 uM |
| (structure 2) | 74% response at 100 uM | 61% response at 100 uM | 7 | 69% response at 100 uM |
| (structure 3) | 99% response at 100 uM | 77% response at 100 uM | 9 | 73% response at 100 uM |

TABLE 1-continued

Examples of determined activities via the assay described above.

| Compound | NR2A | NR2B | NR2C IC$_{50}$ (μM) | NR2D |
|---|---|---|---|---|
| (structure: 4-pyridyl ketone pyrrolinone with 4-MeO₂C-phenyl and indolylethyl) | 78% response at 100 uM | 72% response at 100 uM | 8 | 72% response at 100 uM |
| (structure: acetyl pyrrolinone with 4-EtO₂C-phenyl and indolylethyl) | 96% response at 100 uM | 75% response at 100 uM | 15 | 79% response at 100 uM |
| (structure: acetyl pyrrolinone with 4-EtO₂C-phenyl and 2-methyl-indolylethyl) | 89% response at 100 uM | 79% response at 100 uM | 12 | 73% response at 100 uM |
| (structure: acetyl pyrrolinone with 4-MeO₂C-2-OMe-phenyl and indolylethyl) | 99% response at 100 uM | 79% response at 100 uM | 20 | 99% response at 100 uM |
| (structure: acetyl pyrrolinone with 4-MeO₂C-2-OH-phenyl and indolylethyl) | 102% response at 100 uM | 77% response at 100 uM | 15 | 79% response at 100 uM |

TABLE 1-continued

Examples of determined activities via the assay described above.

| Compound | NR2A | NR2B | NR2C IC$_{50}$ (μM) | NR2D |
|---|---|---|---|---|
| (acetyl-hydroxypyrrolone with methyl benzoate and tryptamine) | 105% response at 100 uM | 76% response at 100 uM | 24 | 73% response at 100 uM |
| (pyridyl ketone hydroxypyrrolone with methyl benzoate and 6-fluorotryptamine) | 80% response at 100 uM | 37% response at 100 uM | 14 | 64% response at 100 uM |
| (pyridyl ketone hydroxypyrrolone with methyl benzoate and 6-chlorotryptamine) | 83% response at 100 uM | 43% response at 100 uM | 4 | 61% response at 100 uM |
| (2-chlorobenzoyl hydroxypyrrolone with methyl benzoate and tryptamine) | 68% response at 100 uM | 72% response at 100 uM | 26 | 115% response at 100 uM |

TABLE 1-continued

Examples of determined activities via the assay described above.

| Compound | NR2A | NR2B | NR2C IC$_{50}$ (μM) | NR2D |
|---|---|---|---|---|
| (structure) | 76% response at 100 uM | IC$_{50}$ 56 | 5 | IC$_{50}$ 52 |
| (structure) | IC$_{50}$ 18 | IC$_{50}$ 7.2 | 11 | IC$_{50}$ 6 |
| (structure) | 43% response at 100 uM | 71% response at 100 uM | 12 | 73% response at 100 uM |
| (structure) | 97% response at 100 uM | 91% response at 100 uM | 84% response at 100 uM | 90% response at 100 uM |

TABLE 1-continued

Examples of determined activities via the assay described above.

| Compound | NR2A | NR2B | NR2C IC$_{50}$ (μM) | NR2D |
|---|---|---|---|---|
| 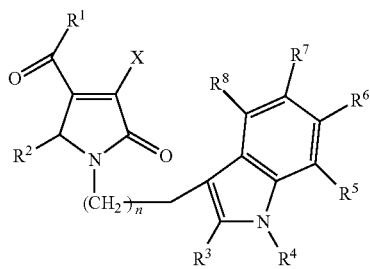 | 103% response at 100 uM | 94% response at 100 uM | 97% response at 100 uM | 95% response at 100 uM |

The invention claimed is:

1. A compound having Formula IA:

Formula IA or salts thereof, wherein

X is OH;

n is 2;

$R^1$ is pyridinyl;

$R^2$ is phenyl, wherein phenyl is substituted with hydroxyl, cyano, trifluoromethyl, or formyl wherein formyl is further substituted with alkoxy, alkylamino, or (alkyl)$_2$ amino; and $R^3$, $R^4$, $R^5$, $R^6$, $R^7$, and $R^8$ are each, the same or different hydrogen, alkyl, halogen or alkoxy.

2. A compound of claim 1, wherein $R^2$ is para-carbomethoxyphenyl or para-carboethoxyphenyl.

3. The compound of claim 1 selected from:
methyl 4-(1-(2-(6-chloro-1H-indol-3-yl)ethyl)-4-hydroxy-3-nicotinoyl-5-oxo-2,5-dihydro-1H-pyrrol-2-yl)benzoate;
methyl 4-(1-(2-(6-fluoro-1H-indol-3-yl)ethyl)-4-hydroxy-3-nicotinoyl-5-oxo-2,5-dihydro-1H-pyrrol-2-yl)benzoate;
methyl 4-(4-hydroxy-1-(2-(6-methyl-1H-indol-3-yl)ethyl)-3-nicotinoyl-5-oxo-2,5-dihydro-1H-pyrrol-2-yl)benzoate;
ethyl 4-(4-hydroxy-1-(2-(6-methyl-1H-indol-3-yl)ethyl)-3-nicotinoyl-5-oxo-2,5-dihydro-1H-pyrrol-2-yl)benzoate;
methyl 4-(1-((1H-indol-3-yl)methyl)-4-hydroxy-3-isonicotinoyl-5-oxo-2,5-dihydro-1H-pyrrol-2-yl)benzoate; and
methyl 4-(4-hydroxy-1-(2-(2-methyl-1H-indol-3-yl)ethyl)-3-nicotinoyl-5-oxo-2,5-dihydro-1H-pyrrol-2-yl)benzoate.

4. A pharmaceutical composition comprising of a therapeutically effective amount of a compound of claim 1 or a pharmaceutically acceptable salt thereof and a pharmaceutically acceptable excipient.

5. A compound methyl 4-(1-((1H-indol-3-yl)methyl)-4-hydroxy-3-isonicotinoyl-5-oxo-2,5-dihydro-1H-pyrrol-2-yl)benzoate or salts thereof.

6. A pharmaceutical composition comprising of a therapeutically effective amount of a compound of claim 5 or a pharmaceutically acceptable salt thereof and a pharmaceutically acceptable excipient.

* * * * *